United States Patent
Kawaguchi et al.

(10) Patent No.: US 10,005,762 B2
(45) Date of Patent: Jun. 26, 2018

(54) PYRIDINE DERIVATIVES

(71) Applicants: Astellas Pharma Inc., Chuo-ku (JP); KOTOBUKI PHARMACEUTICAL CO., LTD., Hanishina-gun (JP)

(72) Inventors: Kenichi Kawaguchi, Tokyo (JP); Akihiro Ishihata, Tokyo (JP); Akira Kanai, Tokyo (JP); Kazuyuki Tsuchiya, Tokyo (JP); Yusuke Inagaki, Tokyo (JP); Junichi Kazami, Saitama (JP); Hiroshi Morikawa, Tokyo (JP); Masashi Hiramoto, Tokyo (JP); Kentaro Enjo, Ibaraki (JP); Hajime Takamatsu, Tokyo (JP)

(73) Assignees: Astellas Pharma Inc., Chuo-ku (JP); KOTOBUKI PHARMACEUTICAL CO., LTD., Hanishina-gun (JP)

( * ) Notice: Subject to any disclaimer, the term of this patent is extended or adjusted under 35 U.S.C. 154(b) by 0 days. days.

(21) Appl. No.: 15/532,772

(22) PCT Filed: Dec. 4, 2015

(86) PCT No.: PCT/JP2015/084098
§ 371 (c)(1),
(2) Date: Jun. 2, 2017

(87) PCT Pub. No.: WO2016/088864
PCT Pub. Date: Jun. 9, 2016

(65) Prior Publication Data
US 2017/0362209 A1    Dec. 21, 2017

(30) Foreign Application Priority Data
Dec. 5, 2014  (JP) ................................ 2014-246463

(51) Int. Cl.
| | | |
|---|---|---|
| *A01N 43/42* | (2006.01) | |
| *A61K 31/44* | (2006.01) | |
| *C07D 405/04* | (2006.01) | |
| *C07D 217/16* | (2006.01) | |
| *C07D 213/55* | (2006.01) | |
| *C07D 221/04* | (2006.01) | |
| *C07D 221/20* | (2006.01) | |
| *C07D 401/04* | (2006.01) | |
| *C07D 217/24* | (2006.01) | |
| *A61K 31/435* | (2006.01) | |

(52) U.S. Cl.
CPC .......... *C07D 405/04* (2013.01); *A61K 31/435* (2013.01); *C07D 213/55* (2013.01); *C07D 217/16* (2013.01); *C07D 217/24* (2013.01); *C07D 221/04* (2013.01); *C07D 221/20* (2013.01); *C07D 401/04* (2013.01)

(58) Field of Classification Search
CPC ............................ C07D 471/04; A61K 31/435
USPC ........................................... 514/299; 546/112
See application file for complete search history.

(56) References Cited

U.S. PATENT DOCUMENTS

| 2016/0002218 A1 | 1/2016 | Takahashi et al. |
| 2017/0190715 A1 | 7/2017 | Kawaguchi et al. |

FOREIGN PATENT DOCUMENTS

| WO | WO 2004/096141 A2 | 11/2004 |
| WO | WO 2004/096141 A3 | 11/2004 |
| WO | WO 2007/072782 A1 | 6/2007 |
| WO | WO 2011/136307 A1 | 11/2011 |
| WO | WO 2014/133056 A1 | 9/2014 |
| WO | WO 2015/182686 A1 | 12/2015 |

OTHER PUBLICATIONS

International Search Report dated Feb. 16, 2016 in PCT/JP2015/084098.
Anthony L. Albiston, et al., "Phenylalanine-544 Plays a Key Role in Substrate and Inhibitor Binding by Providing a Hydrophobic Packing Point at the Active Site of Insulin-Regulated Aminopeptidase", Molecular Pharmacology, vol. 78 No. 4, 2010, pp. 600-607.
Brigitte Bauvois, et al., "Aminopeptidase-N/CD13 (EC 3.4.11.2) Inhibitors: Chemistry, Biological Evaluations, and Therapeutic Prospects", Medicinal Research Reviews, vol. 26 No. 1, 2006, pp. 88-130.
Extended European Search Report dated Mar. 22, 2018 in Patent Application No. 15865019.2, 9 pages.
Konstanze Diefenbach, et al. "Randomised, Double-Blind Study of the Effects of Oxybutynin, Tolterodine, Trospium Chloride and Placebo on Sleep in Healthy Young Volunteers", Clinical Drug Investigation, ADIS International, vol. 23, No. 6, XP002998057, 2003, pp. 395-404.

*Primary Examiner* — Jeffrey H Murray
(74) *Attorney, Agent, or Firm* — Oblon, McClelland, Maier & Neustadt, L.L.P.

(57) ABSTRACT

The problem to be solved by the present invention is to provide a compound suitable for a pharmaceutical composition, specifically an agent for treating nocturia.
The inventors have assumed that inhibition of nocturnal activity of placental leucine aminopeptidase (P-LAP), i.e. aminopeptidase that cleaves AVP, would maintain and/or increase an endogenous AVP level to enhance the antidiuretic effect, which would contribute to a decreased number of nocturnal voids, and have extensively studied compounds which inhibit P-LAP. As a result, the inventors have found that (2R)-3-amino-2-(pyridylmethyl)-2-hydroxy-propanoic acid derivatives have excellent P-LAP inhibitory activity. The inventors have evaluated antidiuretic effects in water-loaded rats and have found that the compounds increase endogenous AVP levels by inhibiting P-LAP and consequently reduce urine production. The present invention therefore provides compounds expected to be used as an agent for treating nocturia based on P-LAP inhibition.

11 Claims, No Drawings

PYRIDINE DERIVATIVES

TECHNICAL FIELD

The present invention relates to a novel pyridine derivative or a salt thereof which is expected as a pharmaceutical, specifically a pharmaceutical for treating nocturia, and to a pharmaceutical containing such a compound as an active ingredient.

BACKGROUND ART

Nocturia is a lower urinary tract symptom defined as "the complaint that the individual has to wake at night one or more times to void" (Neurourol Urodyn 2002; 21: 167-178). Nocturia prevalence increases with age (J Urol 2010; 184: 440-446), and major patients with nocturia are older adults. It impairs quality of life (QOL) in that it disrupts sleep (Eur Urol 2010; 57: 488-498) and increases risk of fracture. Causes of nocturia are global polyuria, nocturnal polyuria, reduced bladder capacity, and sleep disorders, but in many patients nocturia is considered to be multifactorial (Eur Urol 2012; 62: 877-890). Nocturnal polyuria is defined as nocturnal urine volume greater than 33% of the 24-hour urine volume and is present in about 80% of the patients with nocturia (J Urol 2011; 186: 1358-1363).

Arginine-vasopressin (hereinafter, abbreviated as AVP) is an antidiuretic hormone that is a peptide consisting of nine amino acids, and is biosynthesized and secreted in the hypothalamic-pituitary gland axis. AVP receptors are classified into three subtypes: V1a, V1b, and V2. Known major pharmacological actions of AVP in the periphery are vasoconstriction through the V1a receptor, and antidiuresis through the V2 receptor. AVP acts on the renal tubules to promote renal water reabsorption, decreasing the urine volume. For this reason, decreased nocturnal AVP secretion with age is assumed to be a cause of increased nocturnal urine volume (J Int Med 1991; 229: 131-134, BJU Int 2004; 94: 571-575).

Stimulation of the V2 receptor is expected to improve nocturia. Desmopressin (hereinafter, abbreviated as dDAVP) is a selective V2 receptor agonist used for treating patients with nocturia, and is reported to decrease nocturnal urine volume and the number of nocturnal voids, resulting in an increased duration of initial undisturbed sleep (J Urol 2013; 190: 958-964, and J Urol 2013; 190: 965-972). Unfortunately, V2 receptor agonists theoretically induce fluid retention and increase risks of hyponatremia. It is reported that V2 receptor agonists should be administered with caution and monitoring of serum sodium level to older adults who are the majority of patients with nocturia (Neurourol Urodyn 2004; 23: 302-305).

Placental leucine aminopeptidase (hereinafter, abbreviated as P-LAP) is an enzyme that degrades L-leucine-β-naphthylamide, oxytocin and AVP (Arch Biochem Biophys 1992; 292: 388-392), and was cloned as an aminopeptidase by Rogi et al. in year 1996 (J Biol Chem 1996; 271: 56-61). The insulin-regulated aminopeptidase (hereinafter, abbreviated as IRAP) cloned by Keller et al. from rat epididymal fat pads has homology of 87% to human P-LAP. The IRAP is subsequently suggested to be an aminopeptidase that cleaves AVP and reported to be a rat homolog of human P-LAP (J Biol Chem 1995; 270: 23612-23618, Am J Physiol Endocrinol Metab 2007; 293: E1092-E1102). Angiotensin IV (AT$_4$) receptor isolated from bovine adrenal is also suggested to be an IRAP as a result of biochemical and pharmacological studies (J Biol Chem 2001; 276: 48623-48626).

Experiments using P-LAP knockout mice indicate that administration of AVP in wild type mice and P-LAP knockout mice results in much reduction of 24-h urine volume in P-LAP knockout mice, although no significant difference is observed in the 24-h urine volume between the wild type and P-LAP knockout mice. It suggests the possible involvement of P-LAP in regulation of the urine volume through degradation of AVP (NPL 1).

Compounds represented by Formula (A) below are reported to be IRAP inhibitors useful as a therapeutic agent for dementia and diabetes, and the like (PTLs 1 and 2).

[Chemical Formula 1]

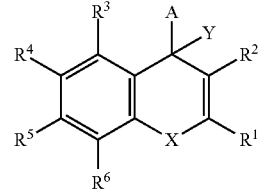

(A)

wherein X is O, NR' or S, and other symbols are defined as in PTLs 1 and 2.

Tripeptide analogs of AT$_4$ with 13- to 14-membered ring structure exhibits excellent TRAP inhibitory activity (NPL 2).

However, no antidiuretic agent or therapeutic agents for nocturia based on a mechanism mediated by P-LAP (or IRAP) has been reported.

Under such circumstances, there exists need for a safe antidiuretic agent that is suitable for treating nocturia.

CITATION LIST

Patent Literature

[PTL 1] WO 2006/026832
[PTL 2] WO 2009/065169

Non Patent Literature

[NPL 1] Life Sciences 84 (2009) 668-672
[NPL 2] J Med Chem 2011; 54; 3779-3792

SUMMARY OF INVENTION

Technical Problem

The present invention provides a compound useful as an active ingredient of a pharmaceutical composition, specifically a pharmaceutical composition for treating nocturia.

Means for Solving Problem

The inventors have assumed that inhibition of nocturnal activity of P-LAP, i.e. aminopeptidase that cleaves AVP, would maintain and/or increase an endogenous AVP level to enhance the antidiuretic effect, which would contribute to a decreased number of nocturnal voids, and have extensively studied compounds which inhibit P-LAP (including rat IRAP, a homolog of human P-LAP).

As a result, the inventors have found that a compound represented by Formula (I) below has excellent P-LAP inhibitory activity. The inventors have evaluated antidiuretic effects in water-loaded rats and have found that the compound represented by Formula (I) increases endogenous AVP levels by inhibiting P-LAP and consequently reduces urine production. Based on such findings, the inventors have accomplished the present invention.

The present invention relates to a compound represented by Formula (I) or a salt thereof, and a pharmaceutical composition comprising the compound represented by Formula (I) or a salt thereof and an excipient:

[Chemical Formula 2]

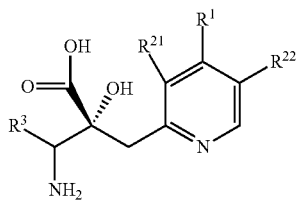

(I)

wherein, $R^1$ is $C_{1-10}$ alkyl optionally having 1 to 5 substituents selected from group $G^1$; $C_{2-10}$ alkenyl optionally having 1 to 5 substituents selected from group $G^1$; $C_{2-10}$ alkynyl optionally having 1 to 5 substituents selected from group $G^1$; -lower alkylene-X-(lower alkyl optionally having 1 to 5 substituents selected from group $G^1$); $R^4$; 5- or 6-membered heterocyclic group optionally having 1 to 5 substituents selected from group $G^3$; -lower alkylene-$R^4$; -lower alkenylene-$R^4$; -lower alkylene-X—$R^4$; or -lower alkylene-X-lower alkylene-$R^4$, or $R^1$ forms, together with $R^{21}$ or $R^{22}$ on the pyridine ring bonded thereto, a hydrocarbon ring fused with the pyridine ring, represented by any of the following formulas (i) to (iv):

[Chemical Formula 3]

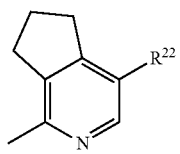

(i)

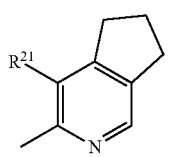

(ii)

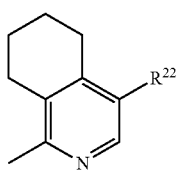

(iii)

-continued

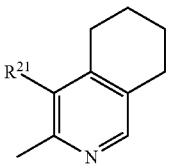

(iv)

wherein the hydrocarbon ring optionally has 1 to 4 substituents selected from the group consisting of lower alkyl optionally having 1 to 5 substituents selected from group $G^1$, cycloalkyl optionally having 1 to 5 substituents selected from group $G^2$, -lower alkylene-$R^4$, and —O-lower alkylene-$R^4$, or the hydrocarbon ring optionally forms a spiro ring with $C_{3-8}$ cycloalkane, $R^{21}$ and $R^{22}$ are the same or different and each are H; lower alkyl optionally having 1 to 5 substituents selected from group $G^1$; —X-lower alkyl; —X-halogeno lower alkyl; cycloalkyl optionally having 1 to 5 substituents selected from group $G^2$; or -lower alkylene-(cycloalkyl optionally having 1 to 5 substituents selected from group $G^2$), $R^3$ is lower alkyl optionally having 1 to 5 substituents selected from group $G^1$; -lower alkylene-X-(lower alkyl optionally having 1 to 5 substituents selected from group $G^1$); -lower alkylene-X-(lower alkenyl optionally having 1 to 5 substituents selected from group $G^1$); -lower alkylene-(cycloalkyl optionally having 1 to 5 substituents selected from group $G^2$); -lower alkylene-X-(cycloalkyl optionally having 1 to 5 substituents selected from group $G^2$); or -lower alkylene-X-lower alkylene-(cycloalkyl optionally having 1 to 5 substituents selected from group $G^2$), each X is independently O or S, each $R^4$ is independently cycloalkyl optionally having 1 to 5 substituents selected from group $G^2$; cycloalkenyl optionally having 1 to 5 substituents selected from group $G^2$; or aryl optionally having 1 to 5 substituents selected from group $G^3$, group $G^1$ consists of halogen, OH, —O-lower alkyl, —S-lower alkyl, —O-halogeno lower alkyl, and CN, group $G^2$ consists of the groups of group $G^1$, lower alkyl optionally having 1 to 5 substituents selected from group $G^1$, and -lower alkylene-(cycloalkyl optionally substituted by 1 to 4 lower alkyl groups), and group $G^3$ consists of the groups of group $G^1$, lower alkyl optionally having 1 to 5 substituents selected from group $G^1$, and benzyloxycarbonyl.

As used herein, if a symbol used in a chemical formula is also used in other chemical formula, identical symbols have the same definition, unless otherwise specified.

The present invention also relates to a pharmaceutical composition comprising the compound represented by Formula (I) or a salt thereof. The pharmaceutical composition encompasses an agent for treating nocturia. The present invention also relates to a pharmaceutical composition for treating nocturia comprising the compound represented by Formula (I) or a salt thereof and an excipient.

The present invention also relates to use of the compound represented by Formula (I) or a salt thereof for production of a pharmaceutical composition for treating nocturia, use of the compound represented by Formula (I) or a salt thereof for treating nocturia, the compound represented by Formula (I) or a salt thereof for treating nocturia, and a method of treating nocturia comprising administering to a subject an effective amount of the compound represented by Formula (I) or a salt thereof. As used herein, "subject" is a human or non-human animal in need of a therapeutic treatment, and in one embodiment, a human in need of the therapeutic treatment.

Effects of Invention

The compound represented by Formula (I) or a salt thereof has inhibitory activity against P-LAP, i.e. the AVP-degrading enzyme, and maintains and/or increases an endogenous AVP level to reduce urine production. Such a compound thus is expected to be used as an agent for treating nocturia, and is also expected to be used as an agent for treating any other voiding dysfunction or polyuria associated with a decreased AVP level, such as pollakiuria, urinary incontinence, and nocturnal enuresis.

DESCRIPTION OF EMBODIMENTS

Hereinafter, the present invention will be described in detail.

In the present specification, the "lower alkyl" is a straight or branched alkyl having one to ten carbon atoms (hereinafter, abbreviated as $C_{1-10}$); specifically, methyl, ethyl, n-propyl, isopropyl, n-butyl, isobutyl, sec-butyl, tert-butyl, isopentyl, isohexyl, isoheptyl, isooctyl, 3-ethylpentyl, 4-ethylhexyl, 4-ethylheptyl, n-hexyl, hexan-2-yl, 4-methylpentan-2-yl, 2,2-dimethylpropyl, 3,3-dimethylpentyl or 3,3-dimethylbutyl. In one embodiment, the "lower alkyl" is a straight or branched $C_{1-6}$ alkyl, in one embodiment, a $C_{1-4}$ alkyl; in one embodiment, the "lower alkyl" is methyl, ethyl, n-propyl, isopropyl, n-butyl, isobutyl, sec-butyl or tert-butyl; in one embodiment, methyl, ethyl, n-propyl or isopropyl; in one embodiment, methyl or ethyl.

The "lower alkyl" in the definition of $R^3$ is, in one embodiment, n-propyl, isopropyl, n-butyl, isobutyl, sec-butyl, tert-butyl, isopentyl, isohexyl, isoheptyl, isooctyl, 3-ethylpentyl, 4-ethylhexyl, 4-ethylheptyl, n-hexyl, hexan-2-yl, 4-methylpentan-2-yl, 2,2-dimethylpropyl, 3,3-dimethylpentyl or 3,3-dimethylbutyl; in one embodiment, a $C_{1-5}$ alkyl. In one embodiment, isobutyl, isopentyl or 2,2-dimethylpropyl.

The "$C_{1-10}$ alkyl" in the definition of $R^1$ is a straight or branched $C_{1-10}$ alkyl as described with respect to "lower alkyl." The "$C_{1-10}$ alkyl" in the definition of $R^1$ is, in one embodiment, methyl, ethyl, n-pentyl, isopentyl, n-hexyl, isohexyl, 4-methylhexyl, n-heptyl, isoheptyl, n-octyl, isooctyl, 3,3-dimethylpentyl or 3,3-dimethylbutyl; in one embodiment, methyl, n-pentyl, isopentyl, n-hexyl or 4-methylhexyl.

The "lower alkenyl" is a straight or branched $C_{2-10}$ alkenyl, and specifically, vinyl, propenyl, butenyl, pentenyl, hexenyl, heptenyl, octenyl, 1-methylvinyl, 1-methyl-2-propenyl, 2-methyl-1-propenyl, 1,3-butadienyl, 3-methyl-1,3-butadienyl, 1,3-pentadienyl. The "lower alkenyl" is, in one embodiment, $C_{2-6}$ alkenyl; in one embodiment, propenyl or butenyl; and in one embodiment, 2-propenyl.

The "$C_{2-10}$ alkenyl" in the definition of $R^1$ is a straight or branched $C_{2-10}$ alkenyl as described with respect to "lower alkenyl." The "$C_{2-10}$ alkenyl" in the definition of $R^1$ is, in one embodiment, vinyl, propenyl, butenyl, pentenyl, hexenyl, heptenyl, octenyl, 1-methylvinyl, 1-methyl-2-propenyl, 2-methyl-1-propenyl, 1,3-butadienyl, 3-methyl-1,3-butadienyl, 1,3-pentadienyl; and in one embodiment, vinyl.

The "$C_{2-10}$ alkynyl" in the definition of $R^1$ is a straight or branched $C_{2-10}$ alkynyl; in one embodiment, ethynyl, propynyl, butynyl, pentynyl, hexynyl, heptynyl, octynyl, 1-methyl-2-propynyl, 1,3-butadiynyl or 1,3-pentadiynyl; and in one embodiment, 1-heptynyl.

The "lower alkylene" is a $C_{1-10}$ straight or branched alkylene; specifically, methylene, ethylene, trimethylene, tetramethylene, pentamethylene, hexamethylene, heptamethylene, octamethylene, methylmethylene, propylene, 2-methyltrimethylene, ethylethylene, 1,2-dimethylethylene or 1,1,2,2-tetramethyl ethylene. In one embodiment, a $C_{1-6}$ alkylene; in one embodiment, a $C_{1-4}$ alkylene; in one embodiment, methylene, ethylene, trimethylene, tetramethylene or 2-methyltrimethylene; in one embodiment, trimethylene. The "lower alkylene" is, in one embodiment, methylene or ethylene; in one embodiment, methylene.

The "lower alkenylene" is a $C_{2-6}$ straight or branched alkenylene; specifically, vinylene, ethylydene, propenylene, butenylene, pentenylene, hexenylene, 1,3-butadienylene or 1,3-pentadienylene. In one embodiment, a $C_{2-4}$ alkenylene; in one embodiment, vinylene or ethylydene; in one embodiment, vinylene.

The "halogen" is F, Cl, Br or I; and in one embodiment, Cl.

The "lower halogenoalkyl" is a straight or branched $C_{1-10}$ alkyl substituted by one or more halogens. The "lower halogenoalkyl" is, in one embodiment, a $C_{1-6}$ alkyl substituted by one to five halogens; in one embodiment, trifluoromethyl, trifluoroethyl, trifluoropropyl, 2-fluoro-2-methylpropyl, difluoromethyl, fluoromethyl or chloromethyl; and in one embodiment, trifluoromethyl.

The "cycloalkyl" is a $C_{3-12}$ saturated hydrocarbon ring group which is optionally cross-linked and optionally forms a spiro ring. The "$C_{3-12}$ cycloalkyl" is, specifically, cyclopropyl, cyclobutyl, cyclopentyl, cyclohexyl, cycloheptyl, cyclooctyl, bicyclo[2,2,1]heptyl, bicyclo[3,1,0]hexyl, bicyclo[3,1,1]heptyl, adamantyl, spiro[2,5]octyl, spiro[3,5]nonyl or spiro[4,5]decyl. In one embodiment, the "cycloalkyl" is cyclopropyl, cyclobutyl, cyclopentyl, cyclohexyl, cycloheptyl or spiro[2,5]octyl; in one embodiment, cyclopropyl, cyclopentyl or spiro[2,5]octyl. The "cycloalkyl" is, in one embodiment, cyclopropyl. In one embodiment, cyclopropyl or cyclobutyl. The "cycloalkyl" is, in one embodiment, a "$C_{3-10}$ cycloalkyl"; in one embodiment, a "$C_{3-8}$ cycloalkyl"; in one embodiment, a "$C_{3-6}$ cycloalkyl".

In case of where the hydrocarbon ring fused with the pyridine ring forms a spiro ring with $C_{3-8}$ cycloalkane, the "$C_{3-8}$ cycloalkane" includes cyclopropane, cyclobutane, cyclopentane, cyclohexane, cycloheptane or cyclooctane; in one embodiment, cyclopentane or cyclohexane; in one embodiment, cyclopentane.

The "cycloalkenyl" is a $C_{3-12}$ nonaromatic hydrocarbon ring group having one or more unsaturated bond, which is optionally crosslinked and optionally forms a spiro ring. The "cycloalkenyl" is, specifically, cyclopentenyl, cyclopentadienyl, cyclohexenyl or cyclohexadienyl; in one embodiment, $C_{5-10}$ cycloalkenyl; in one embodiment, cyclohexenyl.

The "aryl" is a $C_{6-14}$ mono, di or tri-cyclic aromatic hydrocarbon ring group; in one embodiment, phenyl or naphtyl; in one embodiment, phenyl.

The "5 or 6-membered heterocyclic group" is a 5 or 6-membered monocyclic heterocyclic group having 1-4 hetero atoms selected from oxygen, sulfer and nitrogen, which includes a saturated ring, an aromatic ring and their partially hydrogenated ring. Sulfer or nitrogen of the ring atoms is optionally oxydized to form oxide or dioxide. The "5 or 6-membered heterocyclic group" includes, specifically, a monocyclic heteroaryl such as pyridyl, pyrrolyl, pyrazinyl, pyrimidinyl, pyridazinyl, imidazolyl, triazolyl, triazinyl, tetrazolyl, thiazolyl, pyrazolyl, isothiazolyl, oxazolyl, isoxazolyl, thiadiazolyl, oxadiazolyl, thienyl and furyl; or a monocyclic saturated or partially hydrogenated hetero ring such as pyrrolidinyl, piperidyl, piperazinyl, morpholinyl, thiomorpholinyl, tetrahydropyridinyl, dihydropyridinyl, tetrahydrofuranyl, dihydrofuranyl, tetrahydrothienyl, dihydrothienyl, tetrahydropyranyl, dihydropyranyl, dioxolanyl, dioxanyl, tetrahydrothiopyranyl and dihydrothiopyranyl; in one embodiment, tetrahydropyridinyl, tetrahydrofuranyl, dihydrofuranyl, piperidyl, morpholinyl, tetrahydropyranyl, dihydropyranyl, pyridyl, pyrazinyl, pyrimidinyl or pyrazolyl; in one embodiment, 1,2,3,6-tetrahydropyridinyl, tetrahydro-2H-pyranyl or 3,4-dihydro-2H-pyranyl.

In the present specification, the "optionally has substituents" means that the specified group is unsubstituted or has substituents; specifically, the "optionally having 1 to 5 substituents" means that the specified group is unsubstituted or has one to five substituents. If the specified group has a plurality of substituents, the substituents may be the same or different from each other.

The compound represented by Formula (I) having a carboxyl group has at least two asymmetric carbon atoms. One asymmetric carbon atom attached to a hydroxy group (position 2) has (R) configuration, and neighboring carbon atom attached to an amino group (position 3) may have either (R) or (S) configuration, and the compound represented by Formula (I) includes (R) or (S) isomer on position 3, and a mixture thereof. In one embodiment, the compound represented by Formula (I) is a compound represented by Formula (I') or a salt thereof:

[Chemical Formula 4]

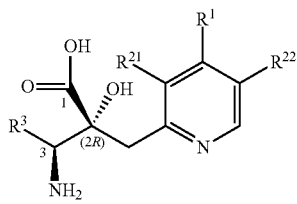

(I')

wherein, (2R) indicates that the carbon atom at position 2 has (R) configuration.

The compound represented by Formula (I) may have tautomers and geometric isomers, depending on the type of substituent groups. The compound represented by Formula (I) also includes separate tautomers and geometric isomers, and mixtures thereof.

The compound represented by Formula (I) may also have stereoisomers based on other asymmetric carbon atom than those described above, depending on the type of substituent groups. The compound represented by Formula (I) also includes separate stereoisomers and mixtures thereof.

The present invention also encompasses a pharmaceutically acceptable prodrug of the compound represented by Formula (I). A pharmaceutically acceptable prodrug is a compound having a group which can be converted into an amino group, a hydroxyl group, or a carboxyl group as a result of solvolysis or under physiological conditions. Examples of a group forming a prodrug are described in Prog. Med., 5, 2157-2161 (1985), "Iyakuhin no Kaihatsu (Pharmaceutical Research and Development)" (Hirokawa-Shoten Ltd.), 1990, Vol. 7, "Bunshi Sekkei (Drug Molecular Design)", pp. 163-198, or "Prodrugs and targeted delivery" (Wiley-VCH 2011) Methods and principles in medicinal chemistry, volume 47.

The salt of the compound represented by Formula (I) is a pharmaceutically acceptable salt of the compound represented by Formula (I). The compound represented by Formula (I) may form an acid addition salt or a salt with a base, depending on the type of substituent groups. Specific examples of the salt include acid addition salts with inorganic acids such as hydrochloric acid, hydrobromic acid, hydroiodic acid, sulfuric acid, nitric acid, and phosphoric acid; acid addition salts with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, and glutamic acid; salts with metal cations such as sodium, potassium, magnesium, calcium, and aluminum; salts with organic bases such as methylamine, ethylamine, and ethanolamine; salts with various amino acids and amino acid derivatives such as acetylleucine, lysine, and ornithine; and ammonium salts.

The present invention also encompasses various hydrates, solvates, and crystalline polymorphs of the compound represented by Formula (I) and a salt thereof. The present invention also encompasses various compounds labeled with a radioactive or nonradioactive isotope.

Some embodiments of the compound represented by Formula (I) or a salt thereof are shown below.

(1-1) A compound or a salt thereof, wherein $R^1$ is $C_{1\text{-}10}$ alkyl optionally having 1 to 5 substituents selected from group $G^1$; $C_{2\text{-}10}$ alkenyl optionally having 1 to 5 substituents selected from group $G^1$; $C_{2\text{-}10}$ alkynyl optionally having 1 to 5 substituents selected from group $G^1$; -lower alkylene-X-(lower alkyl optionally having 1 to 5 substituents selected from group $G^1$); $R^4$; 5- or 6-membered heterocyclic group optionally having 1 to 5 substituents selected from group $G^3$; -lower alkylene-$R^4$; -lower alkenylene-$R^4$; -lower alkylene-X—$R^4$; or -lower alkylene-X-lower alkylene-$R^4$, or $R^1$ forms, together with $R^{21}$ or $R^{22}$ on the pyridine ring bonded thereto, a hydrocarbon ring fused with the pyridine ring, represented by any of the following formulas (i) to (iv):

[Chemical Formula 5]

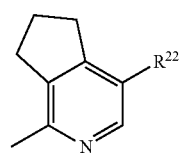

(i)

(ii)

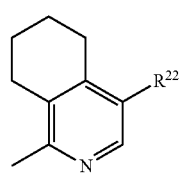

(iii)

-continued

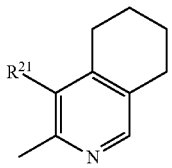
(iv)

wherein the hydrocarbon ring optionally has 1 to 4 substituents selected from the group consisting of lower alkyl optionally having 1 to 5 substituents selected from group $G^1$, cycloalkyl optionally having 1 to 5 substituents selected from group $G^2$, -lower alkylene-$R^4$, and —O-lower alkylene-$R^4$, or the hydrocarbon ring optionally forms a spiro ring with $C_{3-8}$ cycloalkane, $R^{21}$ and $R^{22}$ are the same or different and each are H; lower alkyl optionally having 1 to 5 substituents selected from group $G^1$; —X-lower alkyl; —X-halogeno lower alkyl; cycloalkyl optionally having 1 to 5 substituents selected from group $G^2$; or -lower alkylene-(cycloalkyl optionally having 1 to 5 substituents selected from group $G^2$), each X is independently O or S, and each $R^4$ is independently cycloalkyl optionally having 1 to 5 substituents selected from group $G^2$; cycloalkenyl optionally having 1 to 5 substituents selected from group $G^2$; or aryl optionally having 1 to 5 substituents selected from group $G^3$.

(1-1-i) A compound or a salt thereof, wherein $R^1$ is $C_{1-10}$ alkyl optionally having 1 to 5 substituents selected from group $G^1$; $C_{2-10}$ alkenyl optionally having 1 to 5 substituents selected from group $G^1$; $C_{2-10}$ alkynyl optionally having 1 to 5 substituents selected from group $G^1$; -lower alkylene-X-(lower alkyl optionally having 1 to 5 substituents selected from group $G^1$); $R^4$; 5- or 6-membered heterocyclic group optionally having 1 to 5 substituents selected from group $G^3$; -lower alkylene-$R^4$; -lower alkenylene-$R^4$; -lower alkylene-X—$R^4$; or -lower alkylene-X-lower alkylene-$R^4$, $R^{21}$ and $R^{22}$ are the same or different and each are H; lower alkyl optionally having 1 to 5 substituents selected from group $G^1$; —X-lower alkyl; —X-halogeno lower alkyl; cycloalkyl optionally having 1 to 5 substituents selected from group $G^2$; or -lower alkylene-(cycloalkyl optionally having 1 to 5 substituents selected from group G), each X is independently O or S, and each $R^4$ is independently cycloalkyl optionally having 1 to 5 substituents selected from group $G^2$; cycloalkenyl optionally having 1 to 5 substituents selected from group $G^2$; or aryl optionally having 1 to 5 substituents selected from group $G^3$.

(1-1-ii) A compound or a salt thereof, wherein $R^1$ forms, together with $R^{21}$ or $R^{22}$ on the pyridine ring bonded thereto, a hydrocarbon ring fused with the pyridine ring, represented by any of the above formulas (i) to (iv), wherein the hydrocarbon ring optionally has 1 to 4 substituents selected from the group consisting of lower alkyl optionally having 1 to 5 substituents selected from group $G^1$, cycloalkyl optionally having 1 to 5 substituents selected from group $G^2$, -lower alkylene-$R^4$, and —O-lower alkylene-$R^4$, or the hydrocarbon ring optionally forms a spiro ring with $C_{3-8}$ cycloalkane, each of $R^{21}$ and $R^{22}$ is H; lower alkyl optionally having 1 to 5 substituents selected from group $G^1$; —X-lower alkyl; —X-halogeno lower alkyl; cycloalkyl optionally having 1 to 5 substituents selected from group $G^2$; or -lower alkylene-(cycloalkyl optionally having 1 to 5 substituents selected from group $G^2$), each X is independently O or S, and each $R^4$ is independently cycloalkyl optionally having 1 to 5 substituents selected from group $G^2$; cycloalkenyl optionally having 1 to 5 substituents selected from group $G^2$; or aryl optionally having 1 to 5 substituents selected from group $G^3$.

(1-2) The compound or a salt thereof according to (1-1), wherein $R^1$ is $C_{1-10}$ alkyl optionally having 1 to 5 substituents selected from group $G^1$; $C_{2-10}$ alkenyl optionally having 1 to 5 substituents selected from group $G^1$; $C_{2-10}$ alkynyl optionally having 1 to 5 substituents selected from group $G^1$; cycloalkyl optionally having 1 to 5 substituents selected from group $G^2$; cycloalkenyl; aryl optionally having 1 to 5 substituents selected from group $G^3$; 5- or 6-membered heterocyclic group optionally having 1 to 5 substituents selected from group $G^3$; -lower alkylene-(cycloalkyl optionally having 1 to 5 substituents selected from group $G^2$); -lower alkylene-(aryl optionally having 1 to 5 substituents selected from group $G^3$); -lower alkenylene-aryl; -lower alkylene-O-cycloalkyl; or -lower alkylene-O-aryl, or $R^1$ forms, together with $R^{21}$ or $R^{22}$ on the pyridine ring bonded thereto, a hydrocarbon ring fused with the pyridine ring, represented by any of formulas (i) to (iv), wherein the hydrocarbon ring optionally has 1 to 4 substituents selected from the group consisting of lower alkyl, cycloalkyl, -lower alkylene-(cycloalkyl optionally having 1 to 5 substituents selected from group $G^2$), —O-lower alkylene-(cycloalkyl optionally having 1 to 5 substituents selected from group $G^2$), and —O-lower alkylene-(aryl optionally having 1 to 5 substituents selected from group $G^3$), or the hydrocarbon ring optionally forms a spiro ring with $C_{3-6}$ cycloalkane, and $R^{21}$ and $R^{22}$ are the same or different and each are H, lower alkyl optionally having 1 to 5 substituents selected from group $G^1$, —X-lower alkyl, or cycloalkyl optionally having 1 to 5 substituents selected from group $G^2$.

(1-2-i) The compound or a salt thereof according to (1-1-i), wherein $R^1$ is $C_{1-10}$ alkyl optionally having 1 to 5 substituents selected from group $G^1$; $C_{2-10}$ alkenyl optionally having 1 to 5 substituents selected from group $G^1$; $C_{2-10}$ alkynyl optionally having 1 to 5 substituents selected from group $G^1$; cycloalkyl optionally having 1 to 5 substituents selected from group $G^2$; cycloalkenyl; aryl optionally having 1 to 5 substituents selected from group $G^3$; 5- or 6-membered heterocyclic group optionally having 1 to 5 substituents selected from group $G^3$; -lower alkylene-(cycloalkyl optionally having 1 to 5 substituents selected from group $G^2$); -lower alkylene-(aryl optionally having 1 to 5 substituents selected from group $G^3$); -lower alkenylene-aryl; -lower alkylene-O-cycloalkyl; or -lower alkylene-O-aryl, and $R^{21}$ and $R^{22}$ are the same or different and each are H, lower alkyl optionally having 1 to 5 substituents selected from group $G^1$, —X-lower alkyl, or cycloalkyl optionally having 1 to 5 substituents selected from group $G^2$.

(1-2-ii) The compound or a salt thereof according to (1-1-ii), wherein $R^1$ forms, together with $R^{21}$ or $R^{22}$ on the pyridine ring bonded thereto, a hydrocarbon ring fused with the pyridine ring, represented by any of formulas (i) to (iv), wherein the hydrocarbon ring optionally has 1 to 4 substituents selected from the group consisting of lower alkyl, cycloalkyl, -lower alkylene-(cycloalkyl optionally having 1 to 5 substituents selected from group $G^2$), —O-lower alkylene-(cycloalkyl optionally having 1 to 5 substituents selected from group $G^2$), and —O-lower alkylene-(aryl optionally having 1 to 5 substituents selected from group $G^3$), or the hydrocarbon ring optionally forms a spiro ring with $C_{3-6}$ cycloalkane, and each of $R^{21}$ and $R^{22}$ is H, lower alkyl optionally having 1 to 5 substituents selected from group $G^1$, —X-lower alkyl, or cycloalkyl optionally having 1 to 5 substituents selected from group $G^2$.

(1-3) The compound or a salt thereof according to (1-2), wherein $R^1$ is $C_{1-10}$ alkyl optionally having 1 to 5 substituents selected from the group consisting of halogen and OH; $C_{2-10}$ alkynyl; cycloalkyl optionally having 1 to 5 substituents selected from the group consisting of lower alkyl and -lower alkylene-cycloalkyl; cycloalkenyl; aryl optionally substituted by one (—O-lower alkyl); tetrahydropyridinyl optionally substituted by one benzyloxycarbonyl; dihydropyranyl; tetrahydropyranyl; -lower alkylene-(cycloalkyl optionally substituted by one lower alkyl); -lower alkylene-(aryl optionally having 1 to 5 substituents selected from the group consisting of lower alkyl and —O-lower alkyl); -lower alkenylene-aryl; -lower alkylene-O-cycloalkyl; or -lower alkylene-O-aryl, and $R^{21}$ and $R^{22}$ are the same or different and each are H, lower alkyl, —O-lower alkyl, or cycloalkyl, or $R^1$ forms, together with $R^{21}$ or $R^{22}$ on the pyridine ring bonded thereto, a hydrocarbon ring fused with the pyridine ring, represented by any of formulas (i) to (iii), wherein the hydrocarbon ring optionally has 1 to 4 substituents selected from the group consisting of lower alkyl, -lower alkylene-(cycloalkyl optionally substituted by one lower alkyl), —O-lower alkylene-cycloalkyl, and —O-lower alkylene-aryl, or the hydrocarbon ring optionally forms a spiro ring with $C_{3-6}$ cycloalkane, and each of $R^{21}$ and $R^{22}$ is H.

(1-3-i) The compound or a salt thereof according to (1-2-i), wherein $R^1$ is $C_{1-10}$ alkyl optionally having 1 to 5 substituents selected from the group consisting of halogen and OH; $C_{2-10}$ alkynyl; cycloalkyl optionally having 1 to 5 substituents selected from the group consisting of lower alkyl and -lower alkylene-cycloalkyl; cycloalkenyl; aryl optionally substituted by one (—O-lower alkyl); tetrahydropyridinyl optionally substituted by one benzyloxycarbonyl; dihydropyranyl; tetrahydropyranyl; -lower alkylene-(cycloalkyl optionally substituted by one lower alkyl); -lower alkylene-(aryl optionally having 1 to 5 substituents selected from the group consisting of lower alkyl and —O-lower alkyl); -lower alkenylene-aryl; -lower alkylene-O-cycloalkyl; or -lower alkylene-O-aryl, and $R^{21}$ and $R^{22}$ are the same or different and each are H, lower alkyl, —O-lower alkyl, or cycloalkyl.

(1-3-ii) The compound or a salt thereof according to (1-2-ii), wherein $R^1$ forms, together with $R^{21}$ or $R^{22}$ on the pyridine ring bonded thereto, a hydrocarbon ring fused with the pyridine ring, represented by any of formulas (i) to (iii), wherein the hydrocarbon ring optionally has 1 to 4 substituents selected from the group consisting of lower alkyl, -lower alkylene-(cycloalkyl optionally substituted by one lower alkyl), —O-lower alkylene-cycloalkyl, and —O-lower alkylene-aryl, or the hydrocarbon ring optionally forms a spiro ring with $C_{3-6}$ cycloalkane, and each of $R^{21}$ and $R^{22}$ is H.

(1-4) The compound or a salt thereof according to (1-3), wherein $R^1$ is $C_{1-10}$ alkyl, cycloalkyl substituted by one (-lower alkylene-cycloalkyl), or -lower alkylene-cycloalkyl, $R^{21}$ is H, and $R^{22}$ is H or lower alkyl, or $R^1$ forms, together with $R^{21}$ or $R^{22}$ on the pyridine ring bonded thereto, a hydrocarbon ring fused with the pyridine ring, represented by any of formulas (i) and (ii), wherein the hydrocarbon ring is substituted by one (-lower alkylene-cycloalkyl).

(1-4-i) The compound or a salt thereof according to (1-3-i), wherein $R^1$ is $C_{1-10}$ alkyl; cycloalkyl substituted by one (-lower alkylene-cycloalkyl); or -lower alkylene-cycloalkyl, $R^{21}$ is H, and $R^{22}$ is H or lower alkyl.

(1-4-ii) The compound or a salt thereof according to (1-3-ii), wherein $R^1$ forms, together with $R^{21}$ or $R^{22}$ on the pyridine ring bonded thereto, a hydrocarbon ring fused with the pyridine ring, represented by any of formulas (i) and (ii), wherein the hydrocarbon ring is substituted by one (-lower alkylene-cycloalkyl).

(1-5) The compound or a salt thereof according to (1-3), wherein $R^1$ is -lower alkylene-cycloalkyl, $R^{21}$ is H, and $R^{22}$ is H or $C_{1-4}$ alkyl, or $R^1$ forms, together with $R^{21}$ on the pyridine ring bonded thereto, a hydrocarbon ring fused with the pyridine ring, represented by formula (i), wherein the hydrocarbon ring is substituted by one (-lower alkylene-cycloalkyl).

(1-5-i) The compound or a salt thereof according to (1-3-i), wherein $R^1$ is -lower alkylene-cycloalkyl, $R^{21}$ is H, and $R^{22}$ is H or $C_{1-4}$ alkyl.

(1-5-ii) The compound or a salt thereof according to (1-3-ii), wherein $R^1$ forms, together with $R^{21}$ on the pyridine ring bonded thereto, a hydrocarbon ring fused with the pyridine ring, represented by formula (i), wherein the hydrocarbon ring is substituted by one (-lower alkylene-cycloalkyl).

(1-6) A compound or a salt thereof, wherein $R^1$ is 3-cyclopropylpropyl, $R^{21}$ is H, and $R^{22}$ is H or methyl, or $R^1$ forms, together with $R^{21}$ on the pyridine ring bonded thereto, a hydrocarbon ring fused with the pyridine ring, represented by the following formula (ia):

[Formula 6]

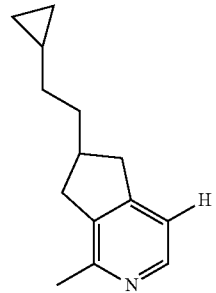

(ia)

(1-6-i) A compound or a salt thereof, wherein $R^1$ is 3-cyclopropylpropyl, $R^{21}$ is H, and $R^{22}$ is H or methyl.

(1-6-ii) A compound or a salt thereof, wherein $R^1$ forms, together with $R^{21}$ on the pyridine ring bonded thereto, a hydrocarbon ring fused with the pyridine ring, represented by formula (ia).

(2-1) A compound or a salt thereof, wherein $R^3$ is lower alkyl optionally having 1 to 5 substituents selected from group $G^1$; -lower alkylene-X-(lower alkyl optionally having 1 to 5 substituents selected from group $G^1$); -lower alkylene-X-(lower alkenyl optionally having 1 to 5 substituents selected from group $G^1$); -lower alkylene-(cycloalkyl optionally having 1 to 5 substituents selected from group $G^2$); -lower alkylene-X-(cycloalkyl optionally having 1 to 5 substituents selected from group $G^2$); or -lower alkylene-X-lower alkylene-(cycloalkyl optionally having 1 to 5 substituents selected from group $G^2$), and each X is independently O or S.

(2-2) The compound or a salt thereof according to (2-1), wherein $R^3$ is lower alkyl optionally having 1 to 5 substituents selected from group $G^1$; -lower alkylene-S-(lower alkyl optionally having 1 to 5 substituents selected from group $G^1$); -lower alkylene-S-lower alkenyl; -lower alkylene-(cycloalkyl optionally having 1 to 5 substituents selected from group $G^2$); -lower alkylene-S-(cycloalkyl optionally having 1 to 5 substituents selected from group $G^2$); or -lower alkylene-X-lower alkylene-(cycloalkyl optionally having 1 to 5 substituents selected from group $G^2$).

(2-3) The compound or a salt thereof according to (2-2), wherein $R^3$ is lower alkyl optionally substituted by 1 to 5 halogen atoms; -lower alkylene-S-lower alkyl; -lower alkylene-S-lower alkenyl; -lower alkylene-($C_{3-8}$ cycloalkyl optionally substituted by one lower alkyl); -lower alkylene-S—$C_{3-8}$ cycloalkyl; or -lower alkylene-X-lower alkylene-$C_{3-8}$ cycloalkyl.

(2-3-ii) A compound or a salt thereof, wherein $R^3$ is lower alkyl optionally substituted by 1 to 5 halogen atoms; -lower alkylene-S-lower alkyl; or -lower alkylene-O-lower alkylene-$C_{3-8}$ cycloalkyl.

(2-4) A compound or a salt thereof, wherein $R^3$ is lower alkyl; -lower alkylene-S-lower alkyl; -lower alkylene-$C_{3-8}$ cycloalkyl; -lower alkylene-S—$C_{3-8}$ cycloalkyl; or -lower alkylene-O-lower alkylene-$C_{3-8}$ cycloalkyl.

(2-4-ii) A compound or a salt thereof, wherein $R^3$ is lower alkyl; -lower alkylene-S-lower alkyl; or -lower alkylene-O-lower alkylene-$C_{3-8}$ cycloalkyl.

(2-5) A compound or a salt thereof, wherein $R^3$ is lower alkyl; -lower alkylene-S-lower alkyl; or -lower alkylene-$C_{3-6}$ cycloalkyl.

(2-5-ii) A compound or a salt thereof, wherein $R^3$ is lower alkyl or -lower alkylene-S-lower alkyl.

(2-6) A compound or a salt thereof, wherein $R^3$ is isobutyl, methylthiomethyl, n-propylthiomethyl, or 2-cyclopropylethyl.

(2-6-i) A compound or a salt thereof, wherein $R^3$ is isobutyl, methylthiomethyl, or 2-cyclopropylethyl.

(2-6-ii) A compound or a salt thereof, wherein $R^3$ is isobutyl, methylthiomethyl, or n-propylthiomethyl.

(2-7) A compound or a salt thereof, wherein $R^3$ is -lower alkylene-$C_{3-6}$ cycloalkyl.

(2-8) A compound or a salt thereof, wherein $R^3$ is -lower alkylene-S-lower alkyl.

(2-9) A compound or a salt thereof, wherein $R^3$ is lower alkyl.

(3) A compound or a salt thereof which is the combination of any of the embodiments described above in (1-1) to (1-6-ii) and any of the embodiments described above in (2-1) to (2-9). Examples thereof include, but are not limited to, the following combinations.

(3-1) A compound or a salt thereof which is the combination of the embodiments of (1-2) and (2-2).

(3-2) A compound or a salt thereof which is the combination of the embodiments of (1-3) and (2-3).

(3-3) A compound or a salt thereof which is the combination of the embodiments of (1-4) and (2-4).

(3-4) A compound or a salt thereof which is the combination of the embodiments of (1-5) and (2-5).

(3-5) A compound or a salt thereof which is the combination of the embodiments of (1-6) and (2-6).

(3-6) A compound or a salt thereof which is the combination of the embodiments of (1-1-i) and (2-1).

(3-7) A compound or a salt thereof which is the combination of the embodiments of (1-2-i) and (2-2).

(3-8) A compound or a salt thereof which is the combination of the embodiments of (1-3-i) and (2-3).

(3-9) A compound or a salt thereof which is the combination of the embodiments of (1-4-i) and (2-4).

(3-10) A compound or a salt thereof which is the combination of the embodiments of (1-5-i) and (2-5).

(3-11) A compound or a salt thereof which is the combination of the embodiments of (1-6-i) and (2-6-i).

(3-12) A compound or a salt thereof which is the combination of the embodiments of (1-1-ii) and (2-1).

(3-13) A compound or a salt thereof which is the combination of the embodiments of (1-2-ii) and (2-2).

(3-14) A compound or a salt thereof which is the combination of the embodiments of (1-3-ii) and (2-3-ii).

(3-15) A compound or a salt thereof which is the combination of the embodiments of (1-4-ii) and (2-4-ii).

(3-16) A compound or a salt thereof which is the combination of the embodiments of (1-5-ii) and (2-5-ii).

(3-17) A compound or a salt thereof which is the combination of the embodiments of (1-6-ii) and (2-6-ii).

(3-18) A compound or a salt thereof which is the combination of the embodiments of (1-4-i) and (2-7).

(3-19) A compound or a salt thereof which is the combination of the embodiments of (1-4-i) and (2-8).

(3-20) A compound or a salt thereof which is the combination of the embodiments of (1-4-i) and (2-9).

In a certain embodiment, the compound of formula (I) or the salt thereof is the compound of formula (I') according to any of the embodiments described above in (3-1) to (3-20).

In a certain embodiment, the compound of formula (I) or the salt thereof is a compound or the salt thereof, wherein the compound is selected from the group consisting of (2R,3R)-3-amino-2-{[4-(3-cyclopropylpropyl)-5-methylpyridin-2-yl]methyl}-2-hydroxy-4-(methylsulfanyl)butanoic acid, (2R,3S)-3-amino-5-cyclopropyl-2-{[4-(3-cyclopropylpropyl)-5-methylpyridin-2-yl]methyl}-2-hydroxypentanoic acid, (2R,3S)-3-amino-2-{[4-(3-cyclopropylpropyl)-5-methylpyridin-2-yl]methyl}-2-hydroxy-5-methylhexanoic acid, (2R,3S)-3-amino-2-{[(6S)-6-(2-cyclopropylethyl)-6,7-dihydro-5H-cyclopenta[c]pyridin-1-yl]methyl}-2-hydroxy-5-methylhexanoic acid, (2R,3S)-3-amino-5-cyclopropyl-2-{[4-(3-cyclopropylpropyl)pyridin-2-yl]methyl}-2-hydroxypentanoic acid, (2R,3R)-3-amino-2-{[(6R)-6-(2-cyclopropylethyl)-6,7-dihydro-5H-cyclopenta[c]pyridin-1-yl]methyl}-2-hydroxy-4-(methylsulfanyl)butanoic acid, (2R,3R)-3-amino-2-{[(6R)-6-(2-cyclopropylethyl)-6,7-dihydro-5H-cyclopenta[c]pyridin-1-yl]methyl}-2-hydroxy-4-(propylsulfanyl)butanoic acid, (2R,3R)-3-amino-2-{[(6S)-6-(2-cyclopropylethyl)-6,7-dihydro-5H-cyclopenta[c]pyridin-1-yl]methyl}-2-hydroxy-4-(methylsulfanyl)butanoic acid, and (2R,3S)-3-amino-2-{[(6R)-6-(2-cyclopropylethyl)-6,7-dihydro-5H-cyclopenta[c]pyridin-1-yl]methyl}-2-hydroxy-5-methylhexanoic acid.

(Preparation Methods)

The compound represented by the formula (I) or a salt thereof can be prepared using the characteristics based on the basic structure or the type of substituents and by applying various known synthesis methods. During the preparation, replacement of the functional group with a suitable protective group (a group that can be easily converted into the functional group) at the stage from starting material to an intermediate may be effective depending on the type of functional groups in the production technology in some cases. Such a protective group may include, for example, the protective groups described in "Greene's Protective Groups in Organic Synthesis (4th edition, 2006)", P. G. M. Wuts and T. W. Greene, and one of these may be selected and used as necessary depending on the reaction conditions. In this kind of method, a desired compound can be obtained by introducing the protective group, by carrying out the reaction and by eliminating the protective group as necessary.

Hereinbelow, the representative preparation methods for the compound represented by the formula (I) will be described. Each of the production processes may also be carried out with reference to the References appended in the present description. Further, the preparation methods of the present invention are not limited to the examples as shown below.

(Production Process 1)

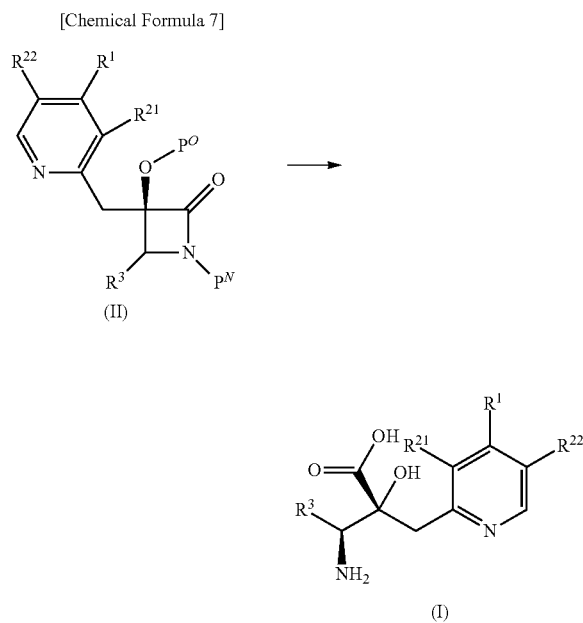

In the formula, $P^O$ represents a protective group for a hydroxyl group, and $P^N$ represents a protective group for an amino group.

The compound (I) in which $R^4$ is OH in Formula (I) can be prepared by ring-opening and deprotection of the compound (II).

In this reaction, the compound (II) and a hydrolytic reagent in equivalent amounts, or either thereof in an excess amount, are used, and the mixture is stirred for usually 0.1 hour to five days in a solvent which is inert to the reaction under from cooling to heating with reflux. Examples of the solvent used herein are not particularly limited, but include alcohols such as methanol, ethanol and n-propanol; halogenated hydrocarbons such as dichloromethane, 1,2-dichloroethane and chloroform; 1,4-dioxane; N,N-dimethylformamide; tetrahydrofuran and the like. In some cases, a mixed solvent of such solvent(s) and water is preferably used for the reaction. Examples of the hydrolytic reagent used herein are not particularly limited, but include bases such as aqueous sodium hydroxide solution and aqueous potassium hydroxide solution; and acids such as hydrogen chloride and trifluoroacetic acid. In some cases, it is preferred to treat the compound (IT) with a base and then with an acid, or to treat it with an acid and then with a base.

Examples of $P^O$, the protective group for a hydroxyl group, include methoxymethyl, benzyloxymethyl and the like. Examples of $P^N$, the protective group for an amino group, include methoxymethyl, benzyloxymethyl and the like.

(Production Process 2)

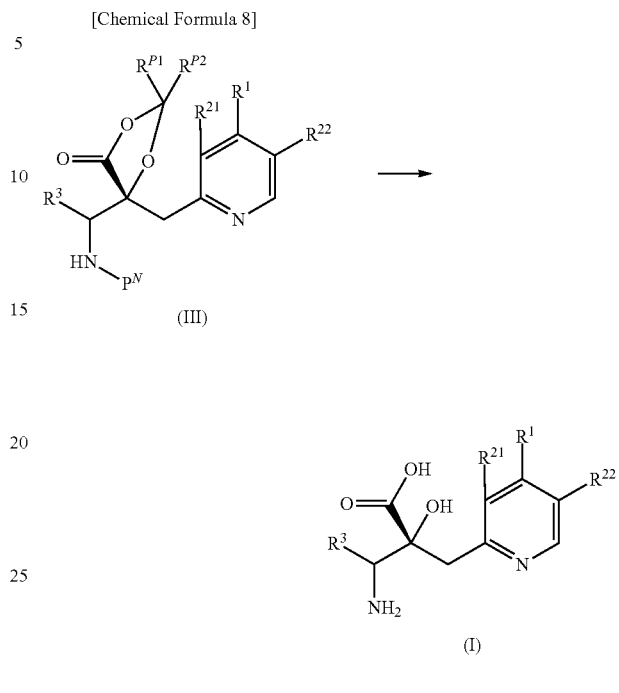

wherein $R^{P1}$ and $R^{P2}$ are a lower alkyl, and in one embodiment, both of them are methyl.

The compound (I) can be prepared by deprotection of the compound (III).

In this reaction, the compound (III) and a deprotecting reagent in equivalent amounts, or either thereof in an excess amount, are used, and the mixture is stirred for usually 0.1 hour to five days in a solvent which is inert to the reaction or in the absence of a solvent, under from cooling to heating with reflux. Examples of the solvent used herein are not particularly limited, but include alcohols such as methanol, ethanol and n-propanol; halogenated hydrocarbons such as dichloromethane, 1,2-dichloroethane and chloroform; 1,4-dioxane; N,N-dimethylformamide; tetrahydrofuran and the like. In some cases, a mixed solvent of such solvent(s) and water is preferably used for the reaction. Examples of the deprotecting reagent are not particularly limited, but include bases such as aqueous sodium hydroxide solution and aqueous potassium hydroxide solution; and acids such as hydrogen chloride and trifluoroacetic acid. In some cases, it is preferred to treat the compound (III) with a base and then with an acid, or to treat it with an acid and then with a base.

Examples of $P^N$, the protective group for an amino group, include tert-butoxycarbonyl, benzyloxycarbonyl, methoxymethyl, benzyloxymethyl and the like.

(Other Production Process)

A compound of Formula (I) prepared by the respective production processes can be used as a starting material and is subjected to a chemical modification reaction generally used by those skilled in the art, such as cyanation and hydrogenation, to produce other compounds represented by Formula (I).

(Synthesis of Starting Material 1)

[Chemical Formula 9]

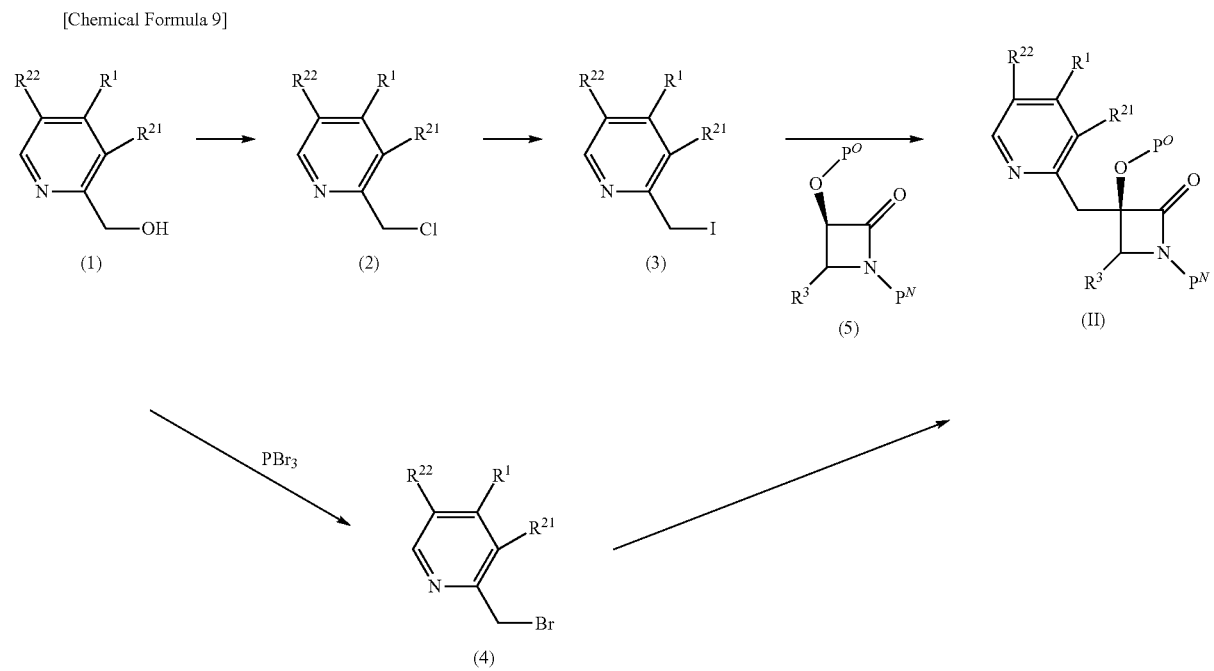

The compound (2) can be prepared through halogenation of a hydroxy group of the compound (1) using thionyl chloride and the like, and the compound (3) can be prepared through iodination of the compound (2) by Finkelstein reaction.
[Reference]
Chirality, 2011, 23(1), 24-33

The compound (II) can be prepared by reacting the compound (3) with the compound (5).

In this reaction, the compounds (3) and (5) in equivalent amounts, or either thereof in an excess amount, are used, the mixture is stirred for usually 0.1 hour to five days in a solvent which is inert to the reaction in the presence of a base under from cooling to room temperature, preferably under cooling. Examples of the solvent used herein are not particularly limited, but include aromatic hydrocarbons such as benzene, toluene and xylene; ethers such as diethylether, tetrahydrofuran, 1,4-dioxane and dimethoxyethane; hexane and a mixture thereof. Examples of the base include organic bases such as lithium diisopropylamide triethylamine, diisopropyl ethylamine, lithium hexamethyldisilazide, potassium hexamethyldisilazide, 1,8-diazabicyclo[5.4.0]-undec-7-ene, n-butyllithium and potassium tert-butoxide; and inorganic bases such as sodium carbonate, potassium carbonate, cesium carbonate and sodium hydride.
[Reference]
Journal of Organic Chemistry, 1990, 55(20), 5525-5528
Tetrahedron Letters, 2000, 41 (33), 6523-6526

Alternatively, the compound (II) can be prepared by reacting the compound (4), which is the brominated compound (1) with $PBr_3$, and the compound (5). In this reaction, the compounds (5) is treated with lithium diisopropylamide under argon atmosphere, the mixture is subsequently stirred for usually 1 hour to five days, under from cooling to room temperature, preferably under cooling, in a solvent which is inert to the reaction such as aromatic hydrocarbons such as benzene, toluene and xylene; ethers such as diethyl ether, tetrahydrofuran, 1,4-dioxane and 1,2-dimethoxyethane; halogenated hydrocarbons such as dichloromethane, 1,2-dichloroethane and chloroform.
[Reference]
Molecules, 2004, 9(5), 365-372
Tetrahedron Asymmetry, 1991, 2(7), 705-720

(Synthesis of Starting Material 2)

[Chemical Formula 10]

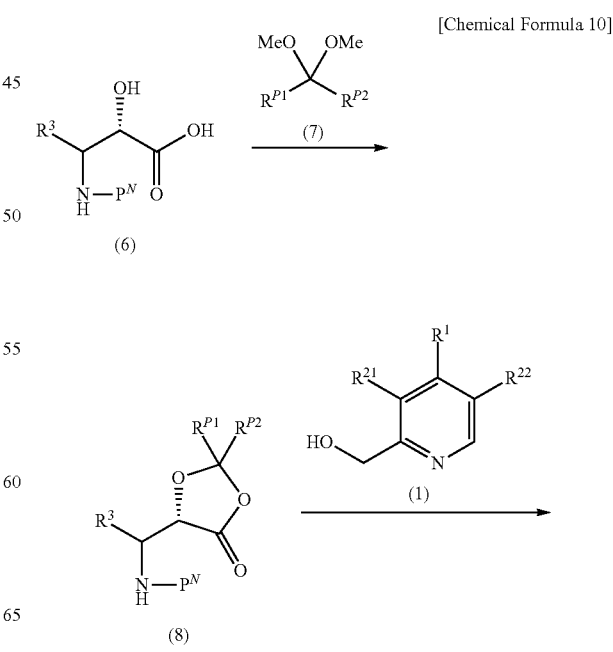

-continued

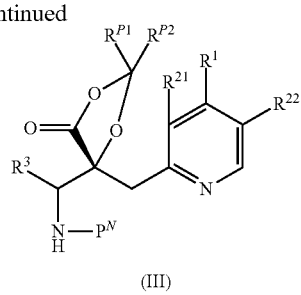

(III)

The compound (8) can be prepared by reacting the compound (6) with the compound (7) in the presence of pyridinium p-toluenesulfonate or p-toluenesulfonic acid. In this reaction, a mixture of the compounds (6) and (7) is stirred for one hour to five days in a solvent which is inert to the reaction in the presence of pyridinium p-toluenesulfonate or p-toluenesulfonic acid under from cooling to heating, preferably at a temperature of from 40 to 120° C. Examples of the solvent include aromatic hydrocarbons such as benzene, toluene and xylene; ethers such as diethylether, tetrahydrofuran, 1,4-dioxane and 1,2-dimethoxyethane; and halogenated hydrocarbons such as dichloromethane, 1,2-dichloroethane and chloroform.

Examples of $P^N$, the protective group for an amino group, include tert-butoxycarbonyl, benzyloxycarbonyl, methoxymethyl, benzyloxymethyl and the like.

The compound (III) can be prepared by reacting the compound (8) with the compound (1). The reaction can be carried out by the same method as in the synthesis of the compound (II) from the compound (1) using the compound (5) described in Synthesis of Starting Material 1.

(Synthesis of Starting Material 3)

[Chemical Formula 11]

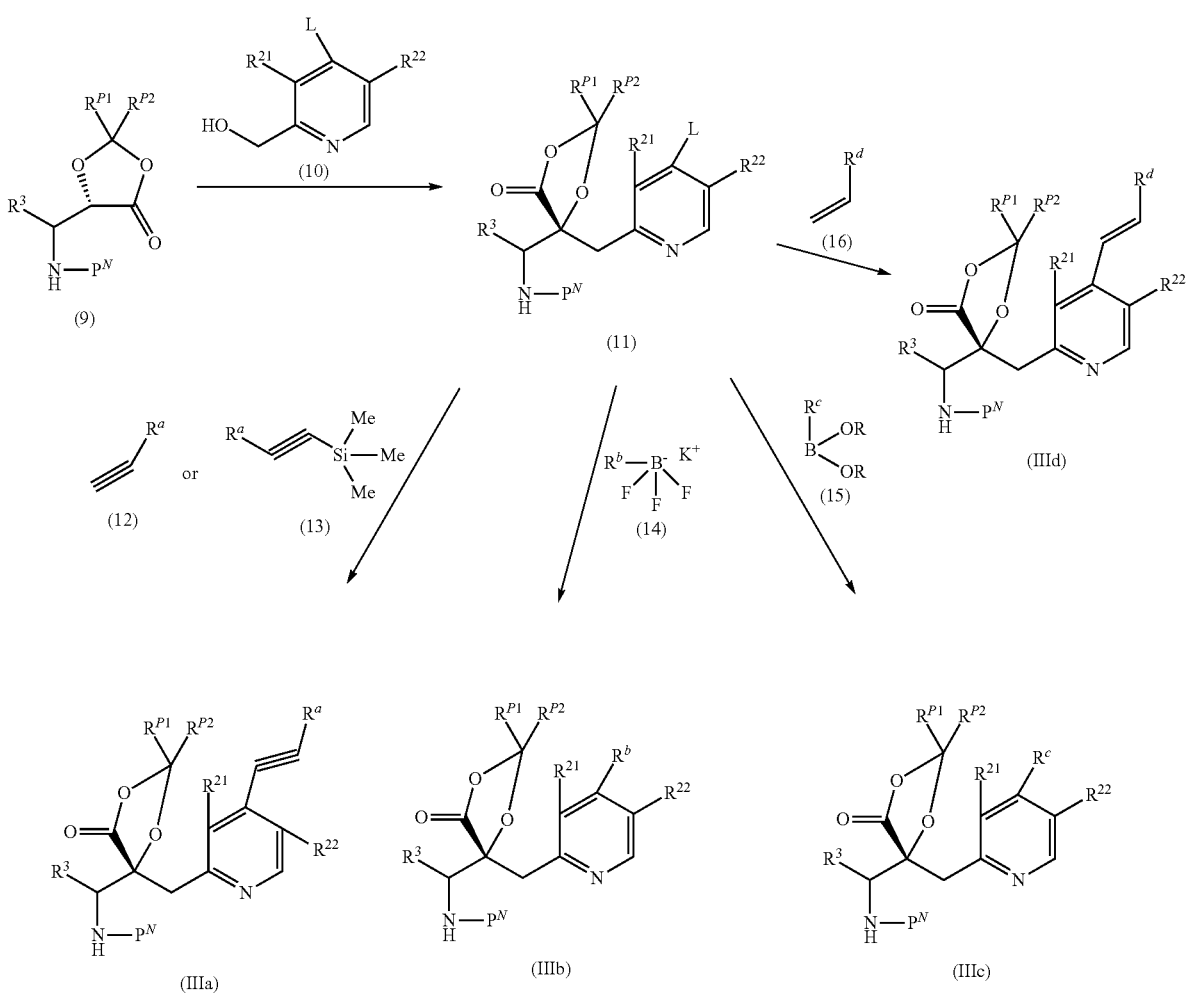

wherein L is Cl, Br, I, a trifluoromethanesulfonyloxy group and the like, $R^c$—$B(OR)_2$ is a boronic acid or a boronic acid ester, and $R^b$ and $R^c$ represent independently any group defined for $R^1$, and $R^a$ and $R^d$ represent independently a group which can be a part of the group defined for $R^1$.

The compound (11) can be obtained from the compound (9) and the compound (10). The reaction can be carried out as in the reaction of the compound (5) with the compound (1) of Synthesis of Starting Material 1.

Further compound (III) can be obtained from compound (11) using various coupling reactions known to those skilled in the art.

For example, when the acetylene derivative of the compound (12) is used, the compound (IIIa) can be obtained using the Sonogashira-Hagiwara coupling reaction. For example, in the presence of a base such as triethylamine and a palladium catalyst such as bis (triphenylphosphine) palladium (II) chloride or the like, the compound (12) can be reacted with the compound (11) in a solvent inert to the reaction such as N,N-dimethylformamide, if necessary under microwave irradiation, to give the compound (IIIa). In this reaction, addition of a copper salt such as CuI may be suitable for the reaction in some cases.

Even when the compound (13), an acetylene derivative substituted by the silyl group, is used, the compound (IIIa) can be obtained in the same manner as in the case of using the compound (12). It is sometimes preferable to add a desilylation agent such as tetra-n-butylammonium fluoride or the like for the reaction.

When trifluoroborate salt of compound (14), or, boronic acid or boronic acid ester of compound (15) is used, the compound (IIIb) or compound (IIIc) can be obtained by Suzuki-Miyaura coupling reaction. For example, the compound (14) can be reacted with the compound (11) in the presence of a cesium carbonate, dicyclohexyl (2',6'-diisopropoxybiphenyl-2-yl) phosphine and a palladium catalyst such as palladium acetate in a solvent inert to the reaction such as toluene to obtain the compound (IIIb). Also, the compound (11) and the compound (15) can be reacted with each other in a solvent inert to the reaction such as 1,4-dioxane, water and the like in the presence of a palladium catalyst such as dichlorobis(tricyclohexylphosphine) palladium and bis (tri-tert-butylphosphine) and a base such as tripotassium phosphate and sodium carbonate to obtain the compound (IIIc).

The compound (16) can be reacted with the compound (11) in a solvent inert to the reaction such as 1,4-dioxane in the presence of a base such as N-cyclohexyl-N-methylcyclohexaneamine and a palladium catalyst such as tris (dibenzylideneacetone) dipalladium and bis(tri-tert-butylphosphine) palladium, to obtain the compound (IIId).

[Reference]
Chem. Rev., 2007, 107, 874-922
Tetrahedron Letters, 2014, 55 (7), 1357-1361
Org. Lett., 2008, 10 (11), 2135-2138
Bioorganic and Medicinal Chemistry Letters, 2011, 21 (6), 1692-1696
J. Am. Chem. Soc., 2001, 123 (29), 6989-7000

It is to be noted that by hydrogenating a compound having an unsaturated bond obtained by the above coupling reaction, using Pd/C, platinum oxide or the like, a corresponding compound having a saturated bond can be obtained.

(Synthesis of Starting Material 4)

[Chemical Formula 12]

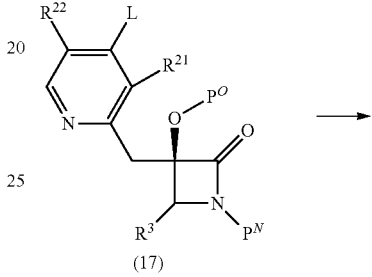

(17)

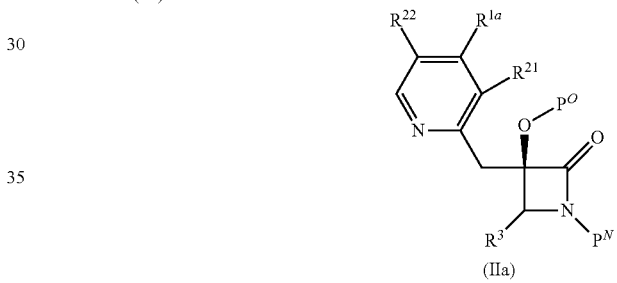

(IIa)

wherein $R^{1a}$ represents any of groups included in $R^1$.

The compound (IIa) can be obtained from the compound (17). The reaction can be carried out as in the process described in Synthesis of Starting Material 3.

(Synthesis of Other Starting Materials)

A desired starting compound can be prepared using any other method known to those skilled in the art. For example, the methods shown in the reaction scheme below can be used.

[Chemical Formula 13]

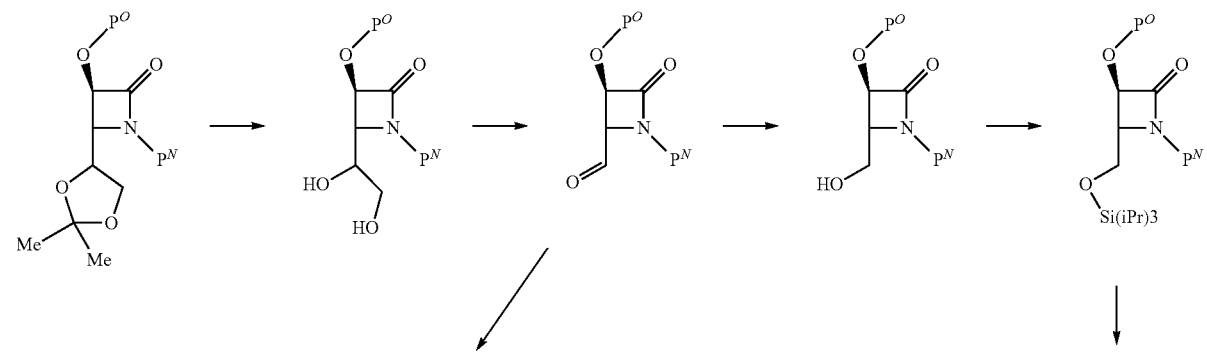

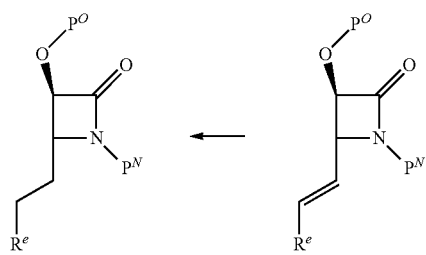
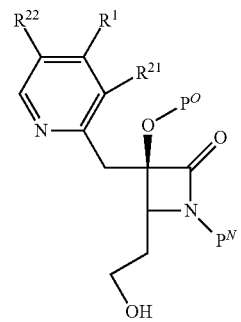

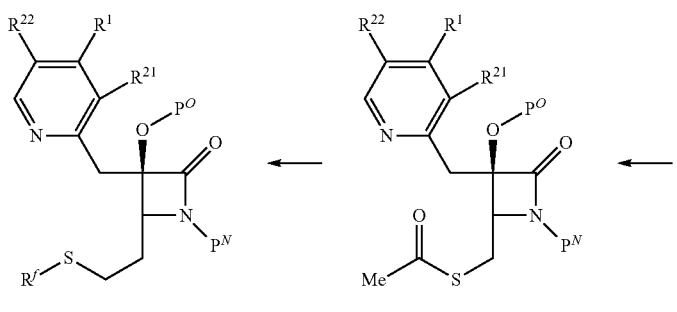
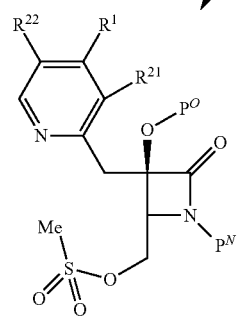

wherein $R^e$ and $R^f$ are each a group forming a part of $R^3$.

The compounds represented by Formula (I) are isolated and purified as free bases, or salts, hydrates, solvates or crystalline polymorphs thereof. Salts of the compound represented by Formula (I) can also be prepared by a conventional salt forming reaction.

Isolation and purification is carried out by a general chemical procedure such as extraction, fractional crystallization, and various types of fractional chromatography.

Various isomers can be prepared by selection of appropriate starting compounds, or can be separated based on differences in physicochemical properties among the isomers. For example, optical isomers can be prepared by a general optical resolution technique of racemic products (for example, fractional crystallization that converts the compound into diastereomer salts with optically active bases or acids, or chromatography using a chiral column), or can also be prepared from appropriate optically active starting compounds.

Pharmacological effects of the compounds represented by Formula (I) were confirmed by the tests described below. Doses of individual test compounds described herein are indicated as corresponding weights of free bases.

(1) Inhibition of IRAP Activity

Rat epididymal fat pads were homogenized and subjected to ultracentrifugation at 100,000×g for 30 minutes to obtain microsomes containing IRAP. The microsomes (with a total protein content of 55 μg/well) were mixed with a solvent (dimethyl sulfoxide; hereinafter, abbreviated as DMSO (final concentration: 0.1%)) or with each test compound (common ratio: 3; maximum concentration: 10 μM). AVP was then added to the solution to a final concentration of 25 μM, and the resulting solution was allowed to react for one hour at 37° C. An aqueous trifluoroacetic acid (hereinafter, abbreviated as TFA) solution was then added to the solution (final concentration: 1%) to stop the enzymatic reaction. Residual AVP was then determined by mass spectrometry (MALDI-MS). Based on the results, $IC_{50}$ values (nM), i.e. concentrations required for 50% inhibition of decrease in AVP level in the solvent control group, of the individual test compounds were calculated by the Sigmoid-Emax model nonlinear regression analysis to evaluate inhibition of IRAP activity.

The results are shown in Table 1, and indicate that most of the example compounds effectively inhibit AVP degradation by IRAP, i.e. a rat homolog of human P-LAP.

(2) Inhibition of Human P-LAP (hP-LAP) Activity

HEK293 cells forced to transiently express hP-LAP (J Biol Chem 1996; 271: 56-61) were prepared by lipofection, homogenized, and then subjected to ultracentrifugation at 100,000×g for 30 minutes. Microsomes containing hP-LAP were thereby prepared. The microsomes (with a total protein content of 0.5 to 1.5 μg/well) were mixed with a solvent (DMSO; final concentration: 0.1%) or with each test compound (common ratio: 3; maximum concentration: 10 μM). AVP was then added to the solution into a final concentration of 25 μM, and the resulting solution was allowed to react for one hour at 37° C. An aqueous TFA solution was then added to the solution (final concentration: 1%) to stop the enzymatic reaction. Residual AVP was then determined by mass spectrometry (MALDI-MS). Based on the results, $IC_{50}$ values (nM), i.e. concentrations required for 50% inhibition of decrease in AVP level in the solvent control group, of the individual test compounds were calculated by the Sigmoid-Emax model nonlinear regression analysis to evaluate inhibition of human P-LAP (hP-LAP) activity. The results are shown in Table 1 and indicate that the tested example compounds effectively inhibit AVP degradation by hP-LAP.

In the Tables 1 and 2 below, numerals in the column "Ex" indicate Example numbers related to the respective test compounds, and --- indicates "not tested".

TABLE 1

| Ex | IRAP IC$_{50}$(nM) | hP-LAP IC$_{50}$(nM) |
|---|---|---|
| 1 | 1.7 | 3.4 |
| 2 | 20 | 84 |
| 3 | 0.58 | 2.4 |
| 4(1) | 1.7 | 2.3 |
| 4(2) | 2.8 | 6.2 |
| 4(3) | 1.2 | 2.6 |
| 5 | 5.1 | 5.3 |
| 6(1) | 42 | 160 |
| 6(2) | 1.8 | 5.2 |
| 7 | 370 | — |
| 8 | 11 | 18 |
| 9 | 15 | 43 |
| 10(1) | >10000 | — |
| 10(2) | 240 | — |
| 11 | 19 | 15 |
| 12 | 12 | 9.0 |
| 13 | 29 | 27 |
| 14 | 93 | 90 |
| 15 | 56 | 350 |
| 16 | 5.9 | 19 |
| 17 | 20 | 100 |
| 18 | 25 | 24 |
| 19 | 220 | — |
| 20 | 12 | 81 |
| 21 | 48 | 40 |
| 22 | 40 | 19 |
| 23 | 56 | 41 |
| 24 | 21 | 130 |
| 25 | 8.7 | 34 |
| 26 | 59 | 310 |
| 27 | 3.8 | 25 |
| 28 | 26 | 98 |
| 29 | 8.6 | 33 |
| 30 | 1.4 | 3.1 |
| 31 | 4.4 | 3.4 |
| 32 | 30 | 53 |
| 33 | 29 | 38 |
| 34 | 2.4 | 11 |
| 35 | 0.94 | 1.6 |
| 36 | 1.8 | 7.1 |
| 37 | 15 | 17 |
| 38 | 4.9 | 43 |
| 39 | 6.4 | 44 |
| 40 | 1.6 | 45 |
| 41 | 4.5 | 4.4 |
| 42 | 15 | 20 |
| 43 | 14 | 28 |
| 44 | 2.5 | 6.8 |
| 45 | 3.8 | 16 |
| 46 | 7.1 | 34 |
| 47 | 0.65 | 3.5 |
| 48 | 7.6 | 1.8 |
| 49 | 1.5 | 3.6 |
| 50 | 2.7 | 6.0 |
| 51 | 15 | 4.0 |
| 52 | 5.9 | 4.9 |
| 53 | 5.8 | 7.3 |
| 54 | 15 | 12 |
| 55 | 5.2 | 4.3 |
| 56 | 73 | 37 |
| 57 | 130 | — |
| 58 | 31 | 17 |
| 59 | 110 | — |
| 60 | 31 | 36 |
| 61 | 21 | 12 |
| 62 | 690 | 150 |
| 63 | 120 | 14 |
| 64 | 28 | 18 |
| 65 | 630 | 150 |
| 66 | 91 | 29 |
| 67 | 260 | 37 |
| 68 | 19 | 3.7 |
| 69 | 8.3 | 2.1 |
| 70 | 73 | 6.2 |
| 71 | 20 | 3.9 |
| 72 | 4.6 | 3.2 |
| 73 | 1.5 | 2.2 |
| 74 | 3.2 | 2.6 |
| 75 | 2.3 | 3.1 |
| 76 | 800 | — |
| 77 | 33 | 46 |
| 78 | 160 | — |
| 79 | 210 | 46 |
| 80 | 130 | — |

(3) Antidiuresis Test in Water-loaded Rats (Oral Administration)

Individual test compounds were dissolved in a vehicle (containing 10% N,N-dimethylformamide, 10% propylene glycol, and 80% distilled water), and the resulting solution was orally administered to the rats. When a test compound is a free base, one molar equivalent hydrochloric acid was added to dissolve the compound in the solvent. Rats in a vehicle control group were administered only with the vehicle. One hour after the administration, 30 ml/kg of distilled water was orally administered to the rats. One hour after the water loading, the urine volume was measured (urine volumes less than 0.3 ml were considered as 0 ml) to calculate the ratio of the urine volume (urinary excretion rate) to the amount of water load. The inhibition of urination (%) in the compound-administered group in comparison with the vehicle control group was calculated in accordance with the following expression (each group consisted of four to five rats):

Inhibition of urination (%)={[(urinary excretion rate in the vehicle control group)−(urinary excretion rate in the compound-administered group]/(urinary excretion rate in the vehicle control group)}×100

Table 2 shows inhibition of urination (%) observed when some example compounds included in compounds of Formula (I) were respectively administered in the amount of 3 mg/kg. In this regard, the inhibition rates with * were observed when the compounds were respectively administered in the amount of 1 mg/kg. The results indicate that the example compounds have an excellent antidiuretic effect.

TABLE 2

| Ex | Inhibition (%) |
|---|---|
| 1 | 49* |
| 3 | 100 |
| 4(1) | 86 |
| 5 | 84 |
| 6(2) | 90 |
| 9 | 55 |
| 25 | 88 |
| 40 | 100 |
| 41 | 69* |
| 42 | 81* |
| 44 | 51* |
| 52 | 90 |

The results shown above suggest that the compounds represented by Formula (I) inhibit P-LAP (IRAP), i.e. an aminopeptidase that cleaves AVP, to inhibit degradation of endogenous AVP, which results in a reduced urine production.

It is known that the plasma AVP level is strictly regulated by plasma osmolality and that an excessive water intake reduces AVP production and secretion to cause diuresis. The present inventors had obtained the results, from the antidiuresis test in continuously hydrated rats with additional water loading using the compounds having an antidiuretic effect based on P-LAP inhibition, revealing that in a case of an excessive water intake caused by the additional water loading, reduced urine volumes were recovered (PCT/JP2015/065344). It is suggested that the decreased endogenous AVP level caused by the additional water loading reduces the antidiuretic effect. Therefore, the compound represented by Formula (I) having the antidiuretic effect based on P-LAP inhibition is expected to be an agent for treating nocturia involving lower risks of hyponatremia even in a case of an excessive water intake, unlike V2 receptor agonists which requires attention for hyponatremia.

A pharmaceutical composition containing one or more compounds represented by Formula (I) or salts thereof as an active ingredient can be prepared by a common method using an excipient generally used in the art, that is, an excipient or a carrier for a pharmaceutical.

Such a pharmaceutical composition can be administered in any form, such as oral administration of tablets, pills, capsules, granules, powder, or liquid, and parental administration by intraarticular, intravenous, or intramuscular injection, suppositories, transdermal liquid, transdermal patches, transmucosal liquid, transmucosal patches, or inhalations.

A solid composition for oral administration may be in a form of, for example, a tablet, powder, and granules. Such a solid composition contains one or more active ingredients mixed with at least one inactive excipient. The composition may contain an inactive additive, for example, a lubricant, a disintegrating agent, a stabilizing agent, and a solubilizing agent, in accordance with conventional techniques. Tablets or pills may be coated with sugar or a film of gastric or enteric soluble material, if necessary.

A liquid composition for oral administration includes a pharmaceutically acceptable emulsion, solution, suspension, syrup, and elixir, and contains a common inactive diluent, for example, purified water or ethanol. The liquid composition may contain an additive such as a solubilizing agent, a moisturizer, and a suspending agent; a sweetening agent; a flavoring agent; an aromatic agent; and a preservative, in addition to the inactive diluent.

An injection for parenteral administration contains aqueous or non-aqueous sterile solvent, suspension, or emulsion. Examples of the aqueous solvent include distilled water for injection and physiological saline. Examples of the non-aqueous solvent include alcohols such as ethanol. The composition may further contain a tonicity agent, a preservative, a moisturizer, an emulsifier, a dispersant, a stabilizer, or a solubilizing agent. These components are sterilized by filtration through a bacteria retentive filter, blending a bactericide, or irradiation, for example. These components may also be formulated into a sterile solid composition to be dissolved or suspended in a sterile solvent for injection before use.

If the compound represented by Formula (I) is orally administered, an appropriate daily dose is approximately 0.001 to 100 mg/kg, preferably 0.1 to 30 mg/kg, more preferably 0.1 to 10 mg/kg, per body weight, and is administered daily in a single dose or in two to four separate doses. If the compound is intravenously administered, an appropriate daily dose is approximately 0.0001 to 10 mg/kg per body weight, and is administered daily in a single dose or in separate doses. If the compound is transmucosally administered, an appropriate daily dose is approximately 0.001 to 100 mg/kg per body weight, and is administered daily in a single dose or in separate doses. The dose is appropriately determined depending on, for example, the symptom, age, and sex of individual patient. If the compound represented by Formula (I) is used for prevention or treatment of nocturia, it may be preferably administered once daily after supper or before going to bed, for example.

The pharmaceutical composition of the present invention contains one or more compounds represented by Formula (I) or salts thereof in an amount of 0.01 to 100% by weight, in one embodiment 0.01 to 50% by weight, as an active ingredient, while the amount may vary depending on a route of administration, dosage form, site of administration, and the type of excipient or additive.

The compound represented by Formula (I) may be used in combination with various therapeutic agents or preventive agents for diseases to which the compound of Formula (I) is assumed to be effective. The compound represented by Formula (I) and the agent to be used in combination therewith may be administered simultaneously, sequentially or at desired time intervals. The preparation to be simultaneously administered may be combined with the compound of Formula (I) or formulated as a separate preparation.

EXAMPLES

Hereinbelow, the production processes for the compound represented by Formula (I) will be described in more details with reference to Examples. The present invention is not limited to the compounds described in the Examples. Production processes for starting compounds will be described in Production Examples. The production process for the compound represented by Formula (I) should not be limited to the processes described in the specific Examples and Production Examples below, but the compound represented by Formula (I) can be prepared by a combination of such production processes or by any method obvious to those skilled in the art.

As used herein, the unit "mol/l" for a concentration is abbreviated as "M" for expediency. For example, "1M aqueous sodium hydroxide solution" refers to 1 mol/l aqueous sodium hydroxide solution.

In the Examples, Production Examples and Tables below, the following abbreviations may be used:

DMF: N,N-dimethylfonnamide; AcOEt: ethyl acetate; AcOH: acetic acid; THF: tetrahydrofuran; MeCN: acetonitrile; EtOH: ethanol; MeOH: methanol; DOX: 1,4-dioxane; DMSO: dimethyl sulfoxide, $Et_2O$: diethyl ether; TFA: trifluoroacetic acid; $Et_3N$: triethylamine; DIPEA: diisopropylethylamine; $Pd(OAc)_2$: palladium acetate; Pd/C: palladium on carbon; $NaBH_4$: sodium borohydride; LDA: lithium diisopropylamide; ODS: octadecylsilyl; PEx: Production Example number; Ex: Example number; PSyn: the Production Example number in which a compound is prepared by the same method; Syn: Example number in which a compound is prepared by the same method; Str: chemical structural formula; Boc: tert-butoxycarbonyl; Ph: phenyl; Bn: benzyl; TIPS: triisopropylsilyl; TBDMS: tert-butyl (dimethyl) silyl; TMS: trimethylsilyl; DATA: physicochemical data, ESI+: m/z value in mass spectrometry (electrospray ionization (ESI); representing $[M+H]^+$ unless otherwise specified); and CI+: m/z value in mass spectrometry (chemical ionization (CI); representing $[M+H]^+$ unless otherwise specified).

The compound represented by Formula (I) to be described in Examples later has at least two asymmetric carbon atoms, and among them, the carbon atom (position 2) to which carboxy group is attached has the (R) configuration. In the tables below, the symbol "*" in a chemical structural formula indicates that the corresponding compound is a single isomer having the indicated configuration. The symbol "#1" indicates that the corresponding compound has the indicated steric configuration and is a mixture of isomers which have (R) and (S) configurations, respectively, in an asymmetric carbon with the steric configuration not indicated. The symbol "#2" indicates that the corresponding compound has the indicated configuration and is a mixture of diastereomers in which two substituents other than H on the cyclopropyl ring have the trans configuration. Two compounds represented by the same structural formula to which "$-M" or "$-L" are assigned have the indicated steric configuration, and furthermore, the asymmetric carbon of which the steric configuration is not indicated, is (R) in one compound and (S) in other compound. Of these two compounds, "$-M" represents a more polar diastereomer and "$-L" represents a less polar diastereomer, respectively. Two compounds represented by the same structural formula to which "$2" is attached have the indicated steric configuration, and two substituents, other than H on the two asymmetric carbons of the cyclopropyl ring, have the trans configuration, and furthermore, the two compounds are single stereoisomers with the opposite configuration each other at the two asymmetric carbons on the cyclopropyl ring. Two compounds represented by the same structural formula to which "$-PEx57(1)" or "$-PEx57(2)" are assigned have the indicated steric configuration, and furthermore, the asymmetric carbon of which the steric configuration is not indicated, is (R) in one compound and (S) in other compound. Of the two compounds, "$-PEx57(1)" represents a diastereomer prepared from the compound of Preparation Example 57(1) as a starting material, "$-PEx57(2)" represents a diastereomer prepared from the compound of Preparation Example 57(2) as a starting material, respectively. 2HCl in the structural formula indicates that the compound is dihydrochloride. Further, the compound having a double bond represented by two crossed lines in the structural formula indicates that the double bond is E form or Z form, or a mixture thereof.

In the present specification, a nomenclature software such as ACD/Name (registered trademark, Advanced Chemistry Development, Inc.) may be used for nomenclature of compounds in some cases.

Example 1

To a mixture of (3R,4R)-3-{[4-(3-cyclopropylpropyl)-5-methylpyridin-2-yl]methyl}-3-(methoxymethoxy)-1-(methoxymethyl)-4-[(methylsulfanyl)methyl]azetidin-2-one (100 mg) and $CH_2Cl_2$ (2 ml), TFA (1 ml) was added, and the resulting mixture was stirred overnight at room temperature. To the obtained reaction mixture, MeOH (4 ml) and a 6 M aqueous sodium hydroxide solution (2 ml) were added, and the mixture was stirred at room temperature for 2 hours. The pH of the obtained reaction mixture was adjusted to approximately 7 with 1 M hydrochloric acid and concentrated under reduced pressure. The obtained residue was purified by ODS column chromatography (MeCN/0.1% aqueous formic acid solution) to obtain (2R,3R)-3-amino-2-{[4-(3-cyclopropylpropyl)-5-methylpyridin-2-yl]methyl}-2-hydroxy-4-(methylsulfanyl)butanoic acid (35 mg) as a solid.

Example 2

To a mixture of (3R,4R)-3-{[4-(3-cyclopropylpropyl)pyridin-2-yl]methyl}-4-[(cyclopropyl sulfanyl)methyl]-3-(methoxymethoxy)-1-(methoxymethyl)azetidin-2-one (8.4 mg) and $CH_2Cl_2$ (0.104 ml), TFA (0.104 ml) was added, and the resulting mixture was stirred at room temperature for 2 hours. The reaction mixture was concentrated under reduced pressure. To the obtained residue, MeOH (0.323 ml) and a 6 M aqueous sodium hydroxide solution (0.323 ml) were added, and the mixture was stirred overnight at room temperature. The pH of the obtained reaction mixture was adjusted to approximately 7 by the addition of 1 M hydrochloric acid and concentrated under reduced pressure. The obtained residue was purified by ODS column chromatography (MeCN/0.1% aqueous formic acid solution) to obtain (2R,3R)-4-(allylsulfanyl)-3-amino-2-{[4-(3-cyclopropylpropyl)pyridin-2-yl]methyl})-2-hydroxybutanoic acid (3.3 mg) as a solid.

Example 3

A mixture of (3R,4S)-4-(2-cyclopropylethyl)-3-{[4-(3-cyclopropylpropyl)-5-methylpyridin-2-yl]methyl}-3-(methoxymethoxy)-1-(methoxymethyl)azetidin-2-one (176 mg), THF (5 ml), and a 6 M hydrochloric acid (1 ml) was stirred at 60° C. for 1 hour, and the reaction mixture was then allowed to cool to room temperature. The obtained reaction mixture was neutralized with a 1 M aqueous sodium hydroxide solution and then concentrated under reduced pressure. The obtained residue was purified by ODS column chromatography (MeCN/0.1% aqueous formic acid solution) to obtain (2R,3S)-3-amino-5-cyclopropyl-2-{[4-(3-cyclopropylpropyl)-5-methylpyridin-2-yl]methyl}-2-hydroxypentanoic acid (115 mg) as a solid.

Example 4

To a mixture of tert-butyl {(1S)-1-[(4R)-4-{[4-(3-cyclopropylpropyl)-5-methylpyridin-2-yl]methyl}-2,2-dimethyl-5-oxo-1,3-dioxolan-4-yl]-3-methylbutyl}carbamate (3.1 g), MeOH (35 ml), and DOX (70 ml), a 1 M aqueous sodium hydroxide solution (50 ml) was added at room temperature, and the resulting mixture was stirred at 55° C. for 3 hours and then allowed to cool to room temperature. The obtained reaction mixture was concentrated under reduced pressure. To the obtained residue, DOX (35 ml) was added, and hydrogen chloride (4 M solution in DOX, 140 ml) was added dropwise under ice cooling. The obtained reaction mixture was stirred at room temperature for 30 minutes and then concentrated under reduced pressure. The obtained residue was purified by ODS column chromatography (MeCN/0.1% aqueous formic acid solution) to respectively obtain (1) (2R,3S)-3-amino-2-{[4-(3-cyclopropylpropyl)-5-methylpyridin-2-yl]methyl}-2-hydroxy-5-methylhexanoic acid (1.21 g), (2) (2R,3S)-3-amino-2-{[4-(4-chlorohexyl)-5-methylpyridin-2-yl]methyl}-2-hydroxy-5-methylhexanoic acid (160 mg), and (3) (2R,3S)-3-amino-2-hydroxy-2-{[4-(4-hydroxyhexyl)-5-methylpyridin-2-yl]methyl}-5-methylhexanoic acid (138 mg) as solids.

Example 5

To a mixture of tert-butyl {(1S)-1-[(4R)-4-{[(6S)-6-(2-cyclopropylethyl)-6,7-dihydro-5H-cyclopenta[c]pyridin-1-yl]methyl}-2,2-dimethyl-5-oxo-1,3-dioxolan-4-yl]-3-methylbutyl}carbamate (660 mg), MeOH (10 ml), and DOX (10 ml), a 1 M aqueous sodium hydroxide solution (10 ml) was added, and the resulting mixture was stirred at 50° C. for 4.5 hours. The obtained reaction mixture was allowed to cool to room temperature and then concentrated under reduced pressure. To the obtained residue, DOX (10 ml) was added, and then, hydrogen chloride (4 M solution in DOX, 10 ml) was added under ice cooling. The obtained reaction mixture was stirred at room temperature for 1 hour, then diluted with DOX and water, and concentrated under reduced pressure. The obtained residue was purified by ODS column chromatography (MeCN/0.1% aqueous formic acid solution). The obtained compound was dissolved in a mixture of MeCN and 1 M hydrochloric acid, and the solvent was distilled off under reduced pressure to obtain (2R,3S)-3-amino-2-{[(6S)-6-(2-cyclopropylethyl)-6,7-dihydro-5H-cyclopenta[c]pyridin-1-yl]methyl}-2-hydroxy-5-methylhexanoic acid dihydrochloride (495 mg) as a solid.

Example 6

To a mixture of a mixture of tert-butyl {(1S)-1-[(4R)-4-({4-[(1R,2R)-2-(cyclopropylmethyl)cyclopropyl]pyridin-2-yl}methyl)-2,2-dimethyl-5-oxo-1,3-dioxolan-4-yl]-3-methylbutyl}carbamate and tert-butyl {(1S)-1-[(4R)-4-({4-[(1S,2S)-2-(cyclopropylmethyl)cyclopropyl]pyridin-2-yl}methyl)-2,2-dimethyl-5-oxo-1,3-dioxolan-4-yl]-3-methylbutyl}carbamate (1.3 g), and CH$_2$Cl$_2$ (30 ml), TFA (5 ml) was added, and the resulting mixture was stirred at room temperature for 2 hours. The reaction mixture was concentrated. To the obtained residue, MeOH (20 ml) and a 1 M aqueous sodium hydroxide solution (20 ml) were added, and the mixture was stirred at 60° C. for 2 hours. The obtained reaction mixture was cooled with ice, then the pH was adjusted to approximately 7 with 1 M hydrochloric acid, and concentrated under reduced pressure. To the obtained residue, MeOH (15 ml) and water (5 ml) were added, and insoluble matter was filtered off. The obtained filtrate was purified by ODS column chromatography (MeCN/0.1% aqueous formic acid solution) to obtain (2R,3S)-3-amino-2-({4-[(1R,2R)-2-(cyclopropylmethyl)cyclopropyl]pyridin-2-yl}methyl)-2-hydroxy-5-methylhexanoic acid and (2R,3S)-3-amino-2-({4-[(1S,2S)-2-(cyclopropylmethyl)cyclopropyl]pyridin-2-yl}methyl)-2-hydroxy-5-methylhexanoic acid (760 mg) as a mixture of two diastereomers.

This diastereomeric mixture (400 mg) was subjected to supercritical fluid chromatography (Daicel chiral column OZ-H (10×250 mm), carbon dioxide:EtOH containing 0.1% diethylamine=65:35, flow rate: 15 ml/min, column temperature: 40° C.) to separate the first peak (retention time=3.98 min) and the second peak (retention time=5.29 min). Each fraction was concentrated under reduced pressure to respectively obtain (1) one diastereomer (150 mg) from the first peak and (2) the other diastereomer (167 mg) from the second peak as solids.

Example 7

To a mixture of tert-butyl {(1S)-1-[(4R)-4-{[4-(3-cyclopropylpropyl)-3-methylpyridin-2-yl]methyl}-2,2-dimethyl-5-oxo-1,3-dioxolan-4-yl]-3-methylbutyl}carbamate (90 mg) and CH$_2$Cl$_2$ (2 ml), TFA (0.5 ml) was added, and the resulting mixture was stirred at room temperature for 3 hours. The reaction mixture was concentrated. To the obtained residue, MeOH (2 ml) and a 1 M aqueous sodium hydroxide solution (2 ml) were added, and the mixture was stirred at 60° C. for 2 hours. The obtained reaction mixture was cooled with ice, then the pH was adjusted to approximately 7 with 1 M hydrochloric acid, and concentrated under reduced pressure. To the obtained residue, water (3 ml) was added, and insoluble matter was filtered off. The obtained filtrate was purified by ODS column chromatography (MeCN/0.1% aqueous formic acid solution). To the obtained compound, 1 M hydrochloric acid was added, and the solvent was then distilled off under reduced pressure to obtain (2R,3S)-3-amino-2-{[4-(3-cyclopropylpropyl)-3-methylpyridin-2-yl]methyl}-2-hydroxy-5-methylhexanoic acid dihydrochloride (45 mg) as a solid.

Example 8

A mixture of (3R,4S)-4-isobutyl-3-(methoxymethoxy)-1-(methoxymethyl)-3-[(4-pentylpyridin-2-yl)methyl]azetidin-2-one (166 mg), 6 M hydrochloric acid (3.2 ml), and DOX (0.8 ml) was stirred at 60° C. for 12 hours. The obtained reaction mixture was concentrated, and the residue was purified by ODS column chromatography (MeCN/0.1% aqueous formic acid solution). The obtained compound was dissolved in a mixture of MeCN and 1 M hydrochloric acid, and the solvent was distilled off under reduced pressure to obtain (2R,3S)-3-amino-2-hydroxy-5-methyl-2-[(4-pentylpyridin-2-yl)methyl]hexanoic acid dihydrochloride (127 mg) as a solid.

Example 9

To a mixture of tert-butyl {(1S)-1-[(4R)-4-{[6-(cyclopropylmethyl)-5,6,7,8-tetrahydroisoquinolin-1-yl]methyl}-2,2-dimethyl-5-oxo-1,3-dioxolan-4-yl]-3-methylbutyl}carbamate (380 mg), MeOH (6 ml), and DOX (6 ml), a 1 M aqueous sodium hydroxide solution (6 ml) was added, and the resulting mixture was stirred at 50° C. for 5 hours. The obtained reaction mixture was allowed to cool to room temperature and then concentrated under reduced pressure. To the obtained residue, DOX (6 ml) was added, and then, hydrogen chloride (4 M solution in DOX, 6 ml) was added under ice cooling. The obtained reaction mixture was stirred at room temperature for 1 hour, and a 1 M aqueous sodium hydroxide solution (6 ml) was then added thereto under ice cooling. The obtained mixture was diluted with DOX and concentrated under reduced pressure. The obtained residue was purified by ODS column chromatography (MeCN/0.1% aqueous formic acid solution) to obtain (2R,3S)-3-amino-2-{[6-(cyclopropylmethyl)-5,6,7,8-tetrahydroisoquinolin-1-yl]methyl}-2-hydroxy-5-methylhexanoic acid (229 mg) as a solid.

Example 10

To a mixture of tert-butyl [(1S)-1-{(4R)-4-[(7-ethyl-6,7-dihydro-5H-cyclopenta[c]pyridin-1-yl)methyl]-2,2-dimethyl-5-oxo-1,3-dioxolan-4-yl}-3-methylbutyl]carbamate (60 mg), MeOH (1 ml), and DOX (1 ml), a 1 M aqueous sodium hydroxide solution (1 ml) was added, and the resulting mixture was stirred at 50° C. for 12 hours. The obtained reaction mixture was allowed to cool to room temperature and then concentrated under reduced pressure. To the obtained residue, DOX (1 ml) was added, and then, hydrogen chloride (4 M solution in DOX, 1 ml) was added under ice cooling. The obtained reaction mixture was stirred at room temperature for 1 hour and then concentrated under reduced pressure to obtain a mixture containing two diastereomers of (2R,3S)-3-amino-2-[(7-ethyl-6,7-dihydro-5H-cyclopenta[c]pyridin-1-yl)methyl]-2-hydroxy-5-methylhexanoic acid. The obtained mixture was fractionated and purified by ODS column chromatography (MeCN/0.1% aqueous formic acid solution) to respectively obtain (1) a more polar diastereomer (18.2 mg) and (2) a less polar diastereomer (8.9 mg) as solids.

Example 11

To a mixture of two diastereomers (3R,4S)-3-(methoxymethoxy)-1-(methoxymethyl)-4-(2-methylpropyl)-3-({4-[(1S,2S)-2-propylcyclopropyl]pyridin-2-yl}methyl)azetidin-2-one and (3R,4S)-3-(methoxymethoxy)-1-(methoxymethyl)-4-(2-methylpropyl)-3-({4-[(1R,2R)-2-propylcyclopropyl]pyridin-2-yl}methyl)azetidin-2-one (100 mg), MeOH (5 ml) and a 6 M aqueous sodium hydroxide solution (2 ml) were added at room temperature, and the resulting mixture was stirred at 60° C. for 16 hours. To the obtained reaction mixture, 6 M hydrochloric acid (8 ml) was added under ice cooling, and the mixture was then stirred at room temperature for 14 hours. The obtained reaction mixture was concentrated under reduced pressure, and the residue was purified by ODS column chromatography (MeCN/0.1% aqueous formic acid solution). To the obtained compound, 1 M hydrochloric acid was added, and the solvent was then distilled off under reduced pressure to obtain (2R,3S)-3-amino-2-hydroxy-5-methyl-2-({4-[(1S,2S)-2-propylcyclopropyl]pyridin-2-yl}methyl)hexanoic acid dihydrochloride and (2R,3S)-3-amino-2-hydroxy-5-methyl-2-({4-[(1R,2R)-2-propylcyclopropyl]pyridin-2-yl}methyl)hexanoic acid dihydrochloride (80 mg) as a mixture of two diastereomers as a solid.

Example 12

To a mixture of (3R,4S)-4-isobutyl-3-(methoxymethoxy)-1-(methoxymethyl)-3-({4-[2-(2-methoxyphenyl)ethyl]pyridin-2-yl}methyl)azetidin-2-one (129 mg), MeOH (4 ml), and THF (3 ml), a 6 M aqueous sodium hydroxide solution (3 ml) was added, and the resulting mixture was stirred at 70° C. for 5 hours. The obtained reaction mixture was cooled with ice. Then, 6 M hydrochloric acid (3 ml) was added thereto, and the mixture was concentrated under reduced pressure. To the obtained residue, 1 M hydrochloric acid (6 ml) and isopropanol (1 ml) were added, and the mixture was stirred for 22 hours. The obtained reaction mixture was purified by ODS column chromatography (MeCN/0.1% aqueous formic acid solution) to obtain (2R,3S)-3-amino-2-hydroxy-2-({4-[2-(2-methoxyphenyl)ethyl]pyridin-2-yl}methyl)-5-methylhexanoic acid (55.5 mg) as a solid.

Compounds of Examples shown in tables described later were produced in the same way as the methods of Examples 1 to 12. The structures, physicochemical data, and production methods of the compounds of Examples are shown in the tables described below.

Production Example 1

To a mixture of [4-(3-cyclopropylpropyl)-5-methylpyridin-2-yl]methanol (3.2 g) and $CH_2Cl_2$ (50 ml), thionyl chloride (2.3 ml) was added under ice cooling. The obtained reaction mixture was stirred at the same temperature as above for 2 hours and then added to an aqueous sodium bicarbonate solution under ice cooling. The obtained mixture was extracted with $CHCl_3$. The organic layer was washed with a saturated aqueous solution of sodium bicarbonate and then dried over anhydrous sodium sulfate. The organic layer was concentrated under reduced pressure, and the obtained residue was purified by silica gel column chromatography (hexane/AcOEt). To a fraction containing the target compound, hydrogen chloride (4 M solution in AcOEt, 5 ml) was added, and the mixture was then concentrated under reduced pressure to obtain a solid (3.05 g).

To a mixture of the obtained solid (420 mg) and $CHCl_3$, a saturated aqueous solution of sodium bicarbonate was added, and the resulting mixture was stirred for 5 minutes. The organic layer was separated, and the aqueous layer was extracted with $CHCl_3$. The obtained organic layers were combined and dried over anhydrous magnesium sulfate. The organic layer was concentrated under reduced pressure. To the obtained residue, acetone (5 ml) and sodium iodide (540 mg) were added, and the mixture was stirred at room temperature for 3 hours. Then, to the reaction mixture, AcOEt was added, and the mixture was washed with a 5% aqueous sodium thiosulfate solution. The obtained organic layer was dried over anhydrous magnesium sulfate and then concentrated to approximately 5 ml under reduced pressure. To the obtained solution, toluene was added, and the mixture was concentrated again to approximately 2 ml under reduced pressure (mixture A). A mixture of (3R,4S)-4-(2-cyclopropylethyl)-3-(methoxymethoxy)-1-(methoxymethyl)azetidin-2-one (200 mg) and THF (5 ml) was cooled with a dry ice-MeOH bath under an argon atmosphere. LDA (1.09 M solution in hexane-THF, 0.9 ml) was added thereto with stirring, and the mixture was stirred for 15 minutes. To this reaction mixture, mixture A was added over 15 minutes, and the resulting mixture was then stirred for 30 minutes while cooled with a dry ice-MeOH bath. The obtained reaction mixture was warmed to room temperature. Then, a saturated aqueous solution of ammonium chloride was added thereto, followed by extraction with AcOEt. The obtained organic layer was dried over anhydrous magnesium sulfate and then concentrated under reduced pressure. The obtained residue was purified by silica gel column chromatography (hexane/AcOEt) to obtain (3R,4S)-4-(2-cyclopropylethyl)-3-{[4-(3-cyclopropylpropyl)-5-methylpyridin-2-yl]methyl}-3-(methoxymethoxy)-1-(methoxymethyl)azetidin-2-one (185 mg) as an oil.

Production Example 2

A mixture of (3R,4S)-3-{[4-(3-cyclopropylpropyl)-5-methylpyridin-2-yl]methyl}-3-(methoxymethoxy)-1-(methoxymethyl)-4-{[(triisopropylsilyl)oxy]methyl}azetidin-2-one (1.5 g) and THF (3 ml) was cooled with ice. Then, tetra-n-butylammonium fluoride (1 M solution in THF, 3 ml) was added thereto, and the mixture was stirred at the same temperature as above for 1 hour. To the reaction mixture, a saturated aqueous solution of ammonium chloride was added, followed by extraction with AcOEt. The organic layer was washed with a saturated aqueous solution of sodium chloride, dried over anhydrous magnesium sulfate, and then concentrated under reduced pressure. The obtained residue was purified by silica gel column chromatography ($CHCl_3$/MeOH) to obtain (3R,4S)-3-{[4-(3-cyclopropylpropyl)-5-methylpyridin-2-yl]methyl}-4-(hydroxymethyl)-3-(methoxymethoxy)-1-(methoxymethyl)azetidin-2-one (1.02 g) as an oil.

Production Example 3

To a mixture of (3R,4S)-3-hydroxy-4-isobutylazetidin-2-one (38.9 g), chloro(methoxy)methane (90 ml), and THF (778 ml), NaH (60% dispersion in mineral oil, 26 g) was added in several divided portions (approximately 5 g each) over 1 hour under ice cooling under an argon atmosphere. The obtained reaction mixture was stirred for 1 hour under ice cooling, and a 5% aqueous ammonium chloride solution was then added thereto. The organic layer was separated, and the aqueous layer was then extracted with AcOEt three times. The obtained organic layers were combined and washed with a saturated aqueous solution of sodium bicarbonate and a saturated aqueous solution of sodium chloride. The organic layer was dried over anhydrous magnesium sulfate and concentrated under reduced pressure. The obtained residue was purified by silica gel column chromatography (hexane/AcOEt) to obtain (3R,4S)-4-isobutyl-3-(methoxymethoxy)-1-(methoxymethyl)azetidin-2-one (57.89 g) as an oil.

Production Example 4

To a mixture of (3R,4S)-4-[(4S)-2,2-dimethyl-1,3-dioxolan-4-yl]-3-(methoxymethoxy)azetidin-2-one (302 mg), chloro(methoxy)methane (0.15 ml), tetra-n-butylammonium iodide (500 mg), and THF (9 ml), potassium hexamethyldisilazide (1.0 M solution in THF, 1.5 ml) was added under ice cooling, and the resulting mixture was stirred for 1 hour and then stirred overnight at room temperature. To the obtained reaction mixture, water was added, followed by extraction with AcOEt. The obtained organic layer was dried over anhydrous magnesium sulfate and concentrated under reduced pressure. The obtained residue was purified by silica gel column chromatography (hexane/AcOEt) to obtain (3R,4S)-4-[(4S)-2,2-dimethyl-1,3-dioxolan-4-yl]-3-(methoxymethoxy)-1-(methoxymethyl)azetidin-2-one (247 mg) as an oil.

Production Example 5

To a mixture of (3R,4S)-3-{[4-(3-cyclopropylpropyl)-5-methylpyridin-2-yl]methyl}-4-(hydroxymethyl)-3-(methoxymethoxy)-1-(methoxymethyl)azetidin-2-one (1 g), pyridine (1 ml), and $CH_2Cl_2$ (10 ml), methanesulfonyl chloride (0.6 ml) was added, and the resulting mixture was stirred overnight at room temperature. To the obtained reaction mixture, 1 M hydrochloric acid was added, followed by extraction with AcOEt. The obtained organic layer was washed sequentially with a saturated aqueous solution of sodium bicarbonate and a saturated aqueous solution of sodium chloride, and dried over anhydrous magnesium sulfate. The obtained organic layer was concentrated under reduced pressure to obtain [(2S,3R)-3-{[4-(3-cyclopropylpropyl)-5-methylpyridin-2-yl]methyl}-3-(methoxymethoxy)-1-(methoxymethyl)-4-oxoazetidin-2-yl]methyl (900 mg) methanesulfonate as an oil.

Production Example 6

A mixture of [(2S,3R)-3-{[4-(3-cyclopropylpropyl)-5-methylpyridin-2-yl]methyl}-3-(methoxymethoxy)-1-(methoxymethyl)-4-oxoazetidin-2-yl]methyl methanesulfonate (900 mg), DMF (20 ml), and potassium thioacetate (400 mg) was stirred overnight at 60° C. To the obtained reaction mixture, potassium thioacetate (400 mg) was further added, and the mixture was further stirred at 60° C. for 2 hours. To the obtained reaction mixture, water was added, followed by extraction with AcOEt. The obtained organic layer was washed sequentially with a saturated aqueous solution of sodium bicarbonate and a saturated aqueous solution of sodium chloride, and then dried over anhydrous magnesium sulfate. The obtained organic layer was concentrated under reduced pressure, and the residue was purified by silica gel column chromatography (hexane/AcOEt) to obtain S-{[(2R,3R)-3-{[4-(3-cyclopropylpropyl)-5-methylpyridin-2-yl]methyl}-3-(methoxymethoxy)-1-(methoxymethyl)-4-oxoazetidin-2-yl]methyl}thioacetate (440 mg) as an oil.

Production Example 7

To a solution of (3R,4S)-3-(benzyloxy)-4-(3-methylbutyl)azetidin-2-one (1.456 g) in EtOH (45.5 ml), 10% Pd/C (containing 50% water, 0.73 g) was added, and the mixture was stirred at room temperature for 24 hours under a hydrogen atmosphere. Insoluble matter was filtered off from the obtained reaction mixture, and the filtrate was then concentrated under reduced pressure. The obtained residue was purified by silica gel column chromatography (hexane/AcOEt) to obtain (3R,4S)-3-hydroxy-4-(3-methylbutyl)azetidin-2-one (760 mg) as a solid.

Production Example 8

To a mixture of S-{[(2R,3R)-3-{[4-(3-cyclopropylpropyl)-5-methylpyridin-2-yl]methyl}-3-(methoxymethoxy)-1-(methoxymethyl)-4-oxoazetidin-2-yl]methyl}thioacetate (110 mg), DMF (1.1 ml), MeOH (1.1 ml), triphenylmethanethiol (5 mg), and potassium carbonate (105 mg), iodomethane (0.05 ml) was added, and the resulting mixture was stirred overnight at room temperature. To the obtained reaction mixture, water was added, followed by extraction with AcOEt. The obtained organic layer was washed sequentially with a saturated aqueous solution of sodium bicarbonate and a saturated aqueous solution of sodium chloride, and then dried over anhydrous magnesium sulfate. The obtained organic layer was concentrated under reduced pressure to obtain (3R,4R)-3-{[4-(3-cyclopropylpropyl)-5-methylpyridin-2-yl]methyl}-3-(methoxymethoxy)-1-(methoxymethyl)-4-[(methyl sulfanyl)methyl]azetidin-2-one (100 mg) as an oil.

Production Example 9

A mixture of 5-[(cyclopropylmethyl)sulfonyl]-1-phenyl-1H-tetrazole (3.32 g) and THF (60 ml) was cooled to −78° C. under an argon atmosphere. Lithium hexamethyldisilazide (1.3 M solution in THF, 11 ml) was added thereto, and the mixture was stirred for 30 minutes. To the obtained reaction mixture, (2R,3R)-3-(methoxymethoxy)-1-(4-methoxyphenyl)-4-oxoazetidine-2-carbaldehyde (3.00 g) was added, and the mixture was stirred at the same temperature as above for 30 minutes. The obtained reaction mixture was warmed to room temperature, and a saturated aqueous solution of ammonium chloride was added thereto, followed by extraction with AcOEt. The obtained organic layer was washed with a saturated aqueous solution of sodium chloride, and the organic layer was dried over anhydrous magnesium sulfate. The organic layer was concentrated under reduced pressure, and the obtained residue was purified by silica gel column chromatography (hexane/AcOEt) to obtain (3R)-4-(2-cyclopropylvinyl)-3-(methoxymethoxy)-1-(4-methoxyphenyl)azetidin-2-one (1.73 g) as a solid.

Production Example 10

To a solution of (3R)-4-(2-cyclopropylvinyl)-3-(methoxymethoxy)-1-(4-methoxyphenyl)azetidin-2-one (831 mg) in toluene (25 ml), $PtO_2$ (61 mg) was added, and the mixture was stirred at 0° C. for 6 hours under a hydrogen atmosphere. Insoluble matter was filtered off from the obtained reaction mixture, and the filtrate was then concentrated under reduced pressure. The obtained residue was purified by silica gel column chromatography (hexane/AcOEt) to obtain (3R,4S)-4-(2-cyclopropylethyl)-3-(methoxymethoxy)-1-(4-methoxyphenyl)azetidin-2-one (574 mg) as an oil.

Production Example 11

To a mixture of (3R,4S)-4-(2-cyclopropylethyl)-3-(methoxymethoxy)-1-(4-methoxyphenyl)azetidin-2-one (1.24 g), MeCN (30 ml), and water (15 ml), cerium(IV) ammonium nitrate (6.3 g) was added under ice cooling, and the resulting mixture was stirred for 30 minutes. To the obtained reaction mixture, water and a saturated aqueous solution of sodium bicarbonate were added with stirring, and then, a 2% aqueous sodium bisulfite solution was added. The obtained reaction mixture was filtered through celite pad, and the filtrate was extracted with CHCl$_3$. The obtained organic layer was washed with a saturated aqueous solution of sodium chloride, dried over anhydrous magnesium sulfate, and then concentrated under reduced pressure. The obtained residue was purified by silica gel column chromatography (hexane/AcOEt) to obtain (3R,4S)-4-(2-cyclopropylethyl)-3-(methoxymethoxy)azetidin-2-one (601 mg) as a solid.

Production Example 12

A mixture of (3R,4S)-4-(2-cyclopropylethyl)-3-(methoxymethoxy)azetidin-2-one (591 mg), 1,2-dichloroethane (15.4 ml), chloro(methoxy)methane (1.5 ml), and DIPEA (4 ml) was stirred at 90° C. for 12 hours. The obtained reaction mixture was allowed to cool to room temperature, and a saturated aqueous solution of sodium bicarbonate was then added thereto, followed by extraction with AcOEt. The obtained organic layer was washed with a saturated aqueous solution of sodium chloride and dried over anhydrous magnesium sulfate. The organic layer was concentrated under reduced pressure, and the obtained residue was purified by silica gel column chromatography (hexane/AcOEt) to obtain (3R,4S)-4-(2-cyclopropylethyl)-3-(methoxymethoxy)-1-(methoxymethyl)azetidin-2-one (609 mg) as an oil.

Production Example 13

To a mixture of (3R)-4-(2-cyclobutylvinyl)-3-(methoxymethoxy)-1-(4-methoxyphenyl)azetidin-2-one (1.06 g) and CH$_2$Cl$_2$ (24 ml), (1,5-cyclooctadiene)(pyridine)(tricyclohexylphosphine)iridium(I) hexafluorophosphate (270 mg) was added, and the resulting mixture was stirred overnight at room temperature under a hydrogen atmosphere. The obtained reaction mixture was concentrated under reduced pressure, and the obtained residue was purified by silica gel column chromatography (hexane/AcOEt) to obtain (3R,4S)-4-(2-cyclobutylethyl)-3-(methoxymethoxy)-1-(4-methoxyphenyl)azetidin-2-one (960 mg) as an oil.

Production Example 14

To a mixture of (4-bromo-5-methylpyridin-2-yl)methanol (10 g), (3-cyclopropylprop-1-yn-1-yl)(trimethyl)silane (12.1 g), Et$_3$N (42 ml), tetra-n-butylammonium fluoride (1 M solution in THF, 74 ml), and MeCN (80 ml), bis(triphenylphosphine)palladium(II) dichloride (0.69 g) was added under a nitrogen atmosphere. The obtained mixture was stirred at 85° C. for 2.5 hours. The obtained reaction mixture was allowed to cool to room temperature and then concentrated under reduced pressure. The obtained residue was purified by silica gel column chromatography (hexane/AcOEt) to obtain [4-(3-cyclopropylprop-1-yn-1-yl)-5-methylpyridin-2-yl]methanol (7.65 g) as an oil.

Production Example 15 tert-Butyl {(1S)-1-[(4R)-4-{[4-(3-cyclopropylprop-1-yn-1-yl)-5-methylpyridin-2-yl]methyl}-2,2-dimethyl-5-oxo-1,3-dioxolan-4-yl]-3-methylbutyl}carbamate (3.0 g) was dissolved in EtOH (132 ml), and the solution was filtered. The obtained filtrate was reacted in a continuous flow hydrogenation reaction apparatus (H-Cube(R); manufactured by ThalesNano Nanotechnology Inc.) using CatCart(R) 10% Pd/C (manufactured by ThalesNano Nanotechnology Inc., 70×4 mm) as a cartridge-type catalyst at a flow rate of 1.0 ml/min, a temperature of 60° C., and a pressure of 50 bar. The obtained mixture was concentrated under reduced pressure to obtain tert-butyl {(1S)-1-{[(4R)-4-([4-(3-cyclopropylpropyl)-5-methylpyridin-2-yl]methyl}-2,2-dimethyl-5-oxo-1,3-dioxolan-4-yl]-3-methylbutyl}carbamate (3.1 g) as a foamy solid.

Production Example 16

A mixture of diethyl zinc (1.09 M solution in hexane, 36 ml) and CH$_2$Cl$_2$ (40 ml) was cooled with ice under a nitrogen atmosphere, and a mixture of TFA (3 ml) and CH$_2$Cl$_2$ (15 ml) was added dropwise thereto. The obtained reaction mixture was stirred for 20 minutes under ice cooling, and a mixture of diiodomethane (3.2 ml) and CH$_2$Cl$_2$ (15 ml) was then added dropwise thereto at the same temperature as above. The reaction mixture was stirred for 20 minutes under ice cooling, and a mixture of ethyl (6S)-6-(but-3-en-1-yl)-6,7-dihydro-5H-cyclopenta[c]pyridine-1-carboxylate (950 mg) and CH$_2$Cl$_2$ (15 ml) was then slowly added thereto at the same temperature as above. The obtained reaction mixture was stirred at room temperature for 2 hours, and 1 M hydrochloric acid (100 ml) was then added thereto under ice cooling. The organic layer was separated, washed with a saturated aqueous solution of sodium bicarbonate, then dried over anhydrous magnesium sulfate, and concentrated under reduced pressure. The obtained residue was purified by silica gel column chromatography (hexane/AcOEt) to obtain ethyl (6S)-6-(2-cyclopropylethyl)-6,7-dihydro-5H-cyclopenta[c]pyridine-1-carboxylate (965 mg) as an oil.

Production Example 17

A mixture of (2S,3S)-3-[(tert-butoxycarbonyl)amino]-2-hydroxy-5-methylhexanoic acid (19.0 g), toluene (140 ml), 2,2-dimethoxypropane (95 ml), and pyridinium p-toluenesulfonate (900 mg) was stirred at 80° C. for 14 hours. The obtained reaction mixture was cooled with ice. Then, an aqueous sodium bicarbonate solution was added thereto, and the mixture was stirred at room temperature for 15 minutes. The organic layer was separated, washed sequentially with 1 M hydrochloric acid, an aqueous sodium bicarbonate solution and a saturated aqueous solution of sodium chloride, and then dried over anhydrous magnesium sulfate. The obtained organic layer was concentrated under reduced pressure to obtain tert-butyl {(1S)-1-[(4S)-2,2-dimethyl-5-oxo-1,3-dioxolan-4-yl]-3-methylbutyl}carbamate (18.8 g) as an oil.

Production Example 18

To a mixture of [(6S)-6-(2-cyclopropylethyl)-6,7-dihydro-5H-cyclopenta[c]pyridin-1-yl]methanol (986 mg) and THF (30 ml), a mixture of PBr$_3$ (0.32 ml) and THF (3 ml) was added under ice cooling, and the resulting mixture was then stirred at room temperature for 1 hour. The obtained reaction mixture was poured to a mixture of a saturated aqueous solution of sodium bicarbonate and CH$_2$Cl$_2$ cooled with ice, and the mixture was stirred at room temperature for 5 minutes. The organic layer was separated, and the aqueous layer was extracted with $CH_2Cl_2$. The obtained organic layers were dried over anhydrous magnesium sulfate, diluted with toluene, and then concentrated to approximately 30 ml under reduced pressure. Again, the obtained mixture was diluted with toluene and concentrated to approximately 20 ml under reduced pressure (mixture B). A mixture of (3R,4S)-3-(methoxymethoxy)-1-(methoxymethyl)-4-{[(triisopropylsilyl)oxy]methyl}azetidin-2-one (1.5 g) and THF (20 ml) was cooled with a dry ice-acetone bath under a nitrogen atmosphere. LDA (1.09 M solution in hexane-THF, 5.7 ml) was added thereto with stirring, and the mixture was stirred for 20 minutes. To this reaction mixture, mixture B was added dropwise, and the resulting mixture was then stirred for 1.5 hours while cooled with a dry ice-acetone bath. To the obtained reaction mixture, a saturated aqueous solution of ammonium chloride was added, and the mixture was then warmed to room temperature and extracted with AcOEt. The obtained organic layer was dried over anhydrous magnesium sulfate and concentrated under reduced pressure. The obtained residue was purified by silica gel column chromatography ($CHCl_3$/AcOEt) to obtain (3R, 4S)-3-{[(6S)-6-(2-cyclopropylethyl)-6,7-dihydro-5H-cyclopenta[c]pyridin-1-yl]methyl}-3-(methoxymethoxy)-1-(methoxymethyl)-4-{[(triisopropylsilyl)oxy]methyl}azetidin-2-one (1.97 g) as an oil.

Production Example 19

To a mixture of N-(tert-butoxycarbonyl)-L-serine (20 g) and DMF (480 ml), NaH (60% dispersion in mineral oil, 8.6 g) was added in 5 divided portions under ice cooling under a nitrogen atmosphere with the internal temperature kept below 5° C., and the resulting mixture was then stirred for 1 hour under ice cooling. To the obtained reaction mixture, (2-iodoethyl)cyclopropane (24 g) was added, and the mixture was stirred at room temperature for 14 hours. The obtained reaction mixture was cooled with ice and then the pH was adjusted to approximately 2.5 with water and 1 M hydrochloric acid. The obtained reaction mixture was extracted with AcOEt three times. Then, the organic layer was washed with a saturated aqueous solution of sodium chloride. The obtained organic layer was dried over anhydrous sodium sulfate and concentrated under reduced pressure. To the obtained residue, MeOH (140 ml) and $CH_2Cl_2$ (420 ml) were added, then (diazomethyl)(trimethyl)silane (2 M solution in hexane, 62 ml) was added dropwise under ice cooling with the internal temperature kept below 6° C., and the mixture was then stirred for 10 minutes under ice cooling and at room temperature for 1 hour. To the obtained reaction mixture, AcOH was added, and the reaction mixture was then concentrated under reduced pressure. The obtained residue was purified by silica gel column chromatography (hexane/AcOEt) to obtain methyl N-(tert-butoxycarbonyl)-O-(2-cyclopropylethyl)-L-serinate (6.51 g) as an oil.

Production Example 20

To a mixture of methyl N-(tert-butoxycarbonyl)-O-(2-cyclopropylethyl)-L-serinate (6.5 g), dibromomethane (8.0 g), and THF (22 ml), 2,2,6,6-tetramethylpiperidinyl magnesium chloride-lithium chloride complex (1 M solution in THF-toluene, 91 ml) was added dropwise at −20° C. over 2 hours under a nitrogen atmosphere with the internal temperature kept below −11° C., and the resulting mixture was then stirred at −15° C. for 2 hours. The reaction mixture was poured to a mixture of a 5% aqueous citric acid solution and AcOEt cooled with ice in advance, and the resulting mixture was then stirred for 10 minutes. Organic layer was separated from aqueous layer, and the obtained organic layer was washed with a 5% aqueous citric acid solution three times and then washed with a saturated aqueous solution of sodium chloride. The obtained organic layer was dried over anhydrous sodium sulfate and then concentrated under reduced pressure to obtain a residue containing tert-butyl [(2S)-4,4-dibromo-1-(2-cyclopropylethoxy)-3-oxobutan-2-yl] carbamate (10.7 g) as an oil.

Production Example 21

To a mixture of tert-butyl [(2S)-4,4-dibromo-1-(2-cyclopropylethoxy)-3-oxobutan-2-yl]carbamate (9.6 g) and toluene (76 ml), a 2 M aqueous sodium hydroxide solution (57 ml) was added dropwise over 15 minutes under ice cooling, and the resulting mixture was then stirred at room temperature for 2 hours. To the obtained reaction mixture, toluene and water were added, and aqueous layer was separated from organic layer. The organic layer was extracted with water twice. The extracts were combined with the aqueous layer obtained above, and AcOEt was then added thereto. The obtained mixture was cooled with ice and, then the pH of the aqueous layer was adjusted to approximately 1.5 with 2 M hydrochloric acid. Organic layer was separated from aqueous layer, and the aqueous layer was extracted with AcOEt three times. The obtained organic layers were combined and dried over anhydrous sodium sulfate. The obtained organic layer was concentrated under reduced pressure to obtain (3S)-3-[(tert-butoxycarbonyl)amino]-4-(2-cyclopropylethoxy)-2-hydroxybutanoic acid (4.53 g) as an oil.

Production Example 22

A mixture of (3R,4S)-3-[(4-chloropyridin-2-yl)methyl]-4-isobutyl-3-(methoxymethoxy)-1-(methoxymethyl)azetidin-2-one (50.0 mg), cyclopropylboronic acid (36.2 mg), dichlorobis(tricyclohexylphosphine)palladium (31.0 mg), tripotassium phosphate (59.5 mg), DOX (1.0 ml), and water (0.14 ml) was stirred at 90° C. for 18 hours under a nitrogen atmosphere. The obtained reaction mixture was allowed to cool to room temperature, and cyclopropylboronic acid (24.0 mg) and dichlorobis(tricyclohexylphosphine)palladium (21.0 mg) were added thereto. The obtained reaction mixture was stirred at 90° C. for 24 hours. The obtained mixture was allowed to cool to room temperature, and a saturated aqueous solution of sodium bicarbonate was added thereto, followed by extraction with AcOEt. The obtained organic layer was dried over anhydrous sodium sulfate and then concentrated under reduced pressure. The obtained residue was purified by silica gel column chromatography (hexane/AcOEt) to obtain (3R,4S)-3-[(4-cyclopropylpyridin-2-yl)methyl]-4-isobutyl-3-(methoxymethoxy)-1-(methoxymethyl)azetidin-2-one (41 mg) as an oil.

Production Example 23

To a solution of (3-bromo-2-methylpropyl)cyclopropane (400 mg) in DMF (5 ml), triphenylphosphine (77 mg), CuI (43 mg), bis(pinacolato)diboron (750 mg), and lithium methoxide (10% solution in MeOH, 1.72 g) were added under an argon atmosphere, and the mixture was vigorously stirred at room temperature for 18 hours. To the reaction mixture, AcOEt was added, and insoluble matter was filtered off through celite pad. The obtained filtrate was concentrated under reduced pressure, and the residue was purified by silica gel column chromatography (hexane/Et$_2$O) to obtain 2-(3-cyclopropyl-2-methylpropyl)-4,4,5,5-tetramethyl-1,3,2-dioxaborolane (410 mg) as an oil.

To a solution of the 2-(3-cyclopropyl-2-methylpropyl)-4,4,5,5-tetramethyl-1,3,2-dioxaborolane (300 mg) thus obtained in MeCN (3 ml), a solution of potassium hydrogen fluoride (330 mg) in water (0.8 ml) was added under ice cooling. The obtained reaction mixture was stirred at the same temperature as above for 20 minutes. The reaction mixture was concentrated under reduced pressure, and the obtained residue was washed with acetone. The obtained organic layer was concentrated under reduced pressure. To the residue, Et$_2$O was added, and the resulting insoluble material was collected by filtration to obtain potassium (3-cyclopropyl-2-methylpropyl)(trifluoro)borate (200 mg) as a solid.

Production Example 24

A mixture of (3R,4S)-3-[(4-chloropyridin-2-yl)methyl]-4-isobutyl-3-(methoxymethoxy)-1-(methoxymethyl)azetidin-2-one (150 mg), potassium phenoxymethyltrifluoroborate (135 mg), cesium carbonate (411 mg), dicyclohexyl(2',6'-diisopropoxybiphenyl-2-yl)phosphine (19.6 mg), Pd(OAc)$_2$ (4.7 mg), toluene (3.0 ml), and water (0.63 ml) was stirred at 100° C. for 17 hours under a nitrogen atmosphere. The obtained reaction mixture was allowed to cool to room temperature, and dicyclohexyl(2',6'-diisopropoxybiphenyl-2-yl)phosphine (39.2 mg) and Pd(OAc)$_2$ (9.4 mg) were added thereto. The obtained mixture was stirred at 100° C. for 6 hours. The obtained reaction mixture was allowed to cool to room temperature, and a saturated aqueous solution of sodium bicarbonate was added thereto, followed by extraction with AcOEt. The obtained organic layer was dried over anhydrous sodium sulfate and then concentrated under reduced pressure. The obtained residue was purified by silica gel column chromatography (hexane/AcOEt) to obtain (3R,4S)-4-isobutyl-3-(methoxymethoxy)-1-(methoxymethyl)-3-{[4-(phenoxymethyl)pyridin-2-yl]methyl}azetidin-2-one (116 mg) as an oil.

Production Example 25

To a mixed solution of diisobutyl aluminum hydride (1.04 M solution in CH$_2$Cl$_2$, 50 ml) and Et$_2$O (7 ml), a solution of (3-cyclopropylprop-1-yn-1-yl)(trimethyl)silane (6.5 g) in Et$_2$O (100 ml) was added under ice cooling under a nitrogen atmosphere. The obtained mixture was stirred at room temperature for 1.5 hours and then stirred at 40° C. for 2 hours. Subsequently, the obtained reaction mixture was cooled to −78° C., and a solution of I$_2$ (27 g) in THF (100 ml) was added dropwise thereto. The obtained mixture was warmed to room temperature, and 1 M hydrochloric acid was added thereto. The obtained reaction mixture was extracted with Et$_2$O. The organic layer was washed sequentially with a saturated aqueous solution of sodium bicarbonate and a 25% aqueous sodium thiosulfate solution. The obtained organic layer was dried over anhydrous magnesium sulfate and then concentrated under reduced pressure to obtain [(1E)-3-cyclopropyl-1-iodoprop-1-en-1-yl](trimethyl)silane (13.3 g) as an oil.

A solution of the obtained [(1E)-3-cyclopropyl-1-iodoprop-1-en-1-yl](trimethyl)silane (12 g) in MeOH (20 ml) was added to a solution of sodium methoxide (28% solution in MeOH, 25 g) in MeOH (100 ml) at room temperature under a nitrogen atmosphere, and the mixture was stirred at 40° C. for 4 hours. To the obtained reaction mixture, water was added, followed by extraction with pentane. The obtained organic layer was washed with a saturated aqueous solution of sodium chloride, dried over anhydrous magnesium sulfate, and then concentrated under reduced pressure to obtain [(2E)-3-iodoprop-2-en-1-yl]cyclopropane (8.9 g) as an oil.

Production Example 26

A mixture of [(2E)-3-iodoprop-2-en-1-yl]cyclopropane (8.8 g), bis(pinacolato)diboron (21 g), bis(triphenylphosphine)palladium(II) dichloride (0.88 g), potassium phenoxide (16.8 g), and toluene (500 ml) was stirred at 50° C. for 3 hours under an argon atmosphere. To the reaction mixture, water was added, followed by extraction with Et$_2$O. The organic layer was washed with a saturated aqueous solution of sodium chloride, dried over anhydrous magnesium sulfate, and then concentrated under reduced pressure. The obtained residue was purified by silica gel column chromatography (hexane/AcOEt) to obtain 2-[(1E)-3-cyclopropylprop-1-en-1-yl]-4,4,5,5-tetramethyl-1,3,2-dioxaborolane (3.8 g) as an oil.

Production Example 27

A mixture of (3R,4R)-4-[(4S)-2,2-dimethyl-1,3-dioxolan-4-yl]-3-hydroxy-1-(4-methoxyphenyl)azetidin-2-one (21.94 g), 1,2-dichloroethane (300 ml), chloro(methoxy)methane (23.6 ml), and DIPEA (70 ml) was stirred at 110° C. for 12 hours. To the obtained reaction mixture, water was added, followed by extraction with CHCl$_3$. The obtained organic layer was dried over anhydrous magnesium sulfate, and the organic layer was concentrated under reduced pressure. The resulting solid was washed with a mixed solvent of diisopropyl ether and MeOH to obtain (3R,4S)-4-[(4S)-2,2-dimethyl-1,3-dioxolan-4-yl]-3-(methoxymethoxy)-1-(4-methoxyphenyl)azetidin-2-one (12.30 g) as a solid. The filtrate was further concentrated, and the obtained residue was purified by silica gel column chromatography (CHCl$_3$/MeOH) to obtain the same compound as above (12.75 g) as a solid.

Production Example 28

A mixture of [4-(3-cyclopropylprop-1-yn-1-yl)-5-methylpyridin-2-yl]methanol (500 mg), EtOH (10 ml), and 10% Pd/C (containing 50% water, 50.2 mg) was stirred at room temperature for 14 hours under a hydrogen atmosphere. Insoluble matter was filtered off from the obtained reaction mixture, and the filtrate was then concentrated under reduced pressure to obtain [4-(3-cyclopropylpropyl)-5-methylpyridin-2-yl]methanol (507 mg) as a solid.

Production Example 29

A mixture of (3R,4S)-4-[(4S)-2,2-dimethyl-1,3-dioxolan-4-yl]-3-(methoxymethoxy)-1-(4-methoxyphenyl)azetidin-2-one (3.17 g), AcOH (50 ml), and water (13 ml) was stirred at 50° C. for 4 hours. The obtained reaction mixture was allowed to cool to room temperature and then concentrated under reduced pressure. The obtained residue was purified by silica gel column chromatography (CHCl$_3$/MeOH) to obtain (3R,4S)-4-[(1S)-1,2-dihydroxyethyl]-3-(methoxymethoxy)-1-(4-methoxyphenyl)azetidin-2-one (2.57 g) as an oil.

Production Example 30

To a mixture of (3R,4S)-4-[(1S)-1,2-dihydroxyethyl]-3-(methoxymethoxy)-1-(4-methoxyphenyl)azetidin-2-one (2.09 g), CH$_2$Cl$_2$ (40 ml), and a saturated aqueous solution of sodium bicarbonate (1 ml), sodium periodate (2.3 g) was added, and the resulting mixture was stirred at room temperature for 1 hour. To the obtained reaction mixture, anhydrous magnesium sulfate was added, and the mixture was stirred for 30 minutes. The obtained reaction mixture was filtered through celite pad, and the filtrate was concentrated under reduced pressure to obtain (2R,3R)-3-(methoxymethoxy)-1-(4-methoxyphenyl)-4-oxoazetidine-2-carbaldehyde (1.80 g) as a solid.

Production Example 31

To a mixture of (2R,3R)-3-(methoxymethoxy)-1-(methoxymethyl)-4-oxoazetidine-2-carbaldehyde (5.08 g) and THF (50 ml), NaBH$_4$ (1.2 g) was added under ice cooling, and the resulting mixture was stirred for 30 minutes. To the obtained reaction mixture, water (5 ml) was added, then anhydrous magnesium sulfate was added, and the mixture was stirred at room temperature for 30 minutes. The obtained reaction mixture was filtered, and the filtrate was then concentrated under reduced pressure. The obtained residue was purified by silica gel chromatography (CHCl$_3$/MeOH) to obtain (3R,4S)-4-(hydroxymethyl)-3-(methoxymethoxy)-1-(methoxymethyl)azetidin-2-one (4.43 g) as an oil.

Production Example 32

A mixture of (3R,4S)-4-(hydroxymethyl)-3-(methoxymethoxy)-1-(methoxymethyl)azetidin-2-one (100 mg), triisopropylchlorosilane (0.21 ml), imidazole (140 mg), and DMF (2 ml) was stirred overnight at room temperature. The obtained reaction mixture was added to water, followed by extraction with AcOEt. The obtained organic layer was washed with a saturated aqueous solution of sodium chloride, dried over anhydrous magnesium sulfate, and then concentrated under reduced pressure. The obtained residue was purified by silica gel column chromatography (hexane/AcOEt) to obtain (3R,4S)-3-(methoxymethoxy)-1-(methoxymethyl)-4-{[(triisopropylsilyl)oxy]methyl}azetidin-2-one (137 mg) as an oil.

Production Example 33

To a solution of ethyl (2S)-2-[(tert-butoxycarbonyl)amino]-4-methylpent-4-enoate (5.7 g) in CH$_2$Cl$_2$ (40 ml), TFA (12 ml) was added, and the mixture was stirred at room temperature for 1 hour. The obtained reaction mixture was concentrated under reduced pressure. To the residue, THF (60 ml), benzyl chloroformate (3.2 ml), sodium bicarbonate (4.3 g), and water (60 ml) were added, and the mixture was stirred at room temperature for 1 hour. The obtained reaction mixture was extracted with AcOEt. The organic layer was washed with a saturated aqueous solution of sodium chloride, then dried over anhydrous magnesium sulfate, and then concentrated under reduced pressure. The obtained residue was purified by silica gel column chromatography (hexane/AcOEt) to obtain ethyl (2S)-2-{[(benzyloxy)carbonyl]amino}-4-methylpent-4-enoate (4.2 g) as an oil.

Production Example 34

To a solution of ethyl N-[(benzyloxy)carbonyl]-3-(1-methylcyclopropyl)-L-alaninate (3.8 g) in EtOH (76 ml), 10% Pd/C (containing 50% water, 0.95 g) was added, and the mixture was stirred at room temperature for 1.5 hours under a hydrogen atmosphere. Insoluble matter was filtered off from the obtained reaction mixture, and the filtrate was then concentrated under reduced pressure. To a solution of the obtained residue in THF (76 ml), di-tert-butyl dicarbonate (2.85 g) and DIPEA (2.3 ml) were added under ice cooling, and the mixture was stirred at room temperature for 2 hours. The obtained reaction mixture was poured into a saturated aqueous solution of ammonium chloride, followed by extraction with AcOEt. The obtained organic layer was dried over anhydrous sodium sulfate and then concentrated under reduced pressure. The obtained residue was purified by silica gel column chromatography (hexane/AcOEt) to obtain ethyl N-(tert-butoxycarbonyl)-3-(1-methylcyclopropyl)-L-alaninate (3.2 g) as an oil.

Production Example 35

Hydrogen fluoride-pyridine (25 g) was cooled to −10° C. (ice-MeOH bath), and ethyl (2S)-2-amino-4-methylpent-4-enoate mono{[(1R,4S)-7,7-dimethyl-2-oxobicyclo[2.2.1]hept-1-yl]methanesulfonic acid}salt (7.5 g) was added thereto in small portions with the internal temperature kept below −5° C. The obtained reaction mixture was stirred at room temperature for 3 hours and then cooled again in an ice-MeOH bath, and a saturated aqueous solution of ammonium acetate was added thereto. Subsequently, the pH of the reaction mixture was adjusted to approximately 9.5 with a 28% aqueous ammonia solution. The obtained mixture was extracted with methyl-tert-butyl ether for three times. The obtained organic layer was dried over anhydrous magnesium sulfate and concentrated under reduced pressure. To the obtained residue, THF (50 ml) was added, then DIPEA (3.3 ml) and di-tert-butyl dicarbonate (3.86 ml) were added at room temperature, and the mixture was stirred for 4 hours. The obtained reaction mixture was concentrated under reduced pressure. To the residue, water was added, followed by extraction with AcOEt. The organic layer was dried over anhydrous magnesium sulfate and then concentrated under reduced pressure. The obtained residue was purified by silica gel column chromatography (hexane/AcOEt) to obtain ethyl N-(tert-butoxycarbonyl)-4-fluoro-L-leucinate (2.65 g) as an oil.

Production Example 36

To a mixture of ethyl 1,2,4-triazine-3-carboxylate (1.25 g), (3S)-3-(but-3-en-1-yl)cyclopentanone (1.14 g), and CHCl$_3$ (12.5 ml), pyrrolidine (0.75 ml) was added under a nitrogen atmosphere. The obtained reaction mixture was stirred at 40° C. for 4 hours. The obtained reaction mixture was cooled with ice and diluted with CHCl$_3$ (12.5 ml), and m-chloroperbenzoic acid (containing approximately 25% water, 1.88 g) was then added thereto in several portions with the internal temperature kept below 13° C. The obtained reaction mixture was stirred at room temperature for 1 hour. The obtained reaction mixture was cooled with ice again. m-Chloroperbenzoic acid (containing approximately 25% water, 400 mg) was added thereto in several portions, and the mixture was then stirred at room temperature for 1 hour. To the obtained reaction mixture, a saturated aqueous solution of sodium bicarbonate and a 5% aqueous sodium sulfite solution were added under ice cooling, and the mixture was stirred at room temperature for 15 minutes and then extracted with CHCl$_3$. The obtained organic layer was washed with a saturated aqueous solution of sodium chloride, then dried over anhydrous magnesium sulfate, and concentrated under reduced pressure. The obtained residue was purified by basic silica gel column chromatography (hexane/AcOEt) and then silica gel column chromatography (hexane/AcOEt) to obtain ethyl (1) (6S)-6-(but-3-en-1-yl)-6,7-dihydro-5H-cyclopenta[c]pyridine-1-carboxylate (960 mg) and (2) ethyl (5S)-5-(but-3-en-1-yl)-6,7-dihydro-5H-cyclopenta[c]pyridine-1-carboxylate (487 mg) as oils.

Production Example 37

To a mixture of ethyl (6S)-6-(2-cyclopropylethyl)-6,7-dihydro-5H-cyclopenta[c]pyridine-1-carboxylate (954 mg) and MeOH (30 ml), NaBH$_4$ (1.12 g) was added in several portions under ice cooling under a nitrogen atmosphere. The obtained reaction mixture was gradually warmed to room temperature over 2 hours and then stirred at room temperature for 12 hours. To the obtained reaction mixture, acetone was added, and the mixture was then concentrated under reduced pressure. To the obtained residue, AcOEt and an aqueous solution of sodium chloride were added. The organic layer was separated, and the aqueous layer was extracted with AcOEt. The obtained organic layer was dried over anhydrous magnesium sulfate and concentrated under reduced pressure. The obtained residue was purified by silica gel column chromatography (hexane/AcOEt) to obtain [(6S)-6-(2-cyclopropylethyl)-6,7-dihydro-5H-cyclopenta[c]pyridin-1-yl]methanol (715 mg) as an oil.

Production Example 38

To a mixture of (1-methylcyclopropyl)methanol (887 mg), triphenylphosphine (2.8 g), imidazole (725 mg), MeCN (3 ml), and Et$_2$O (10 ml), I$_2$ (2.8 g) was added, and the resulting mixture was stirred at room temperature for 2 hours. Insoluble matter was filtered off from the obtained reaction mixture. To the filtrate, hexane (20 ml) and silica gel were added, and insoluble matter was filtered off again. The obtained filtrate was concentrated under reduced pressure to obtain 1-(iodomethyl)-1-methylcyclopropane (1.9 g) as an oil.

Production Example 39

A mixture of [(4S)-4,4'-bi-1,3-benzodioxole-5,5'-diyl]bis[bis(3,5-di-tert-butyl-4-methoxyphenyl)phosphine] (160 mg), copper(II) acetate monohydrate (27.0 mg), and toluene (10 ml; used after being bubbled with argon gas over 30 minutes) was stirred at room temperature for 2 hours under an argon atmosphere. To the obtained reaction mixture, polymethylhydrosiloxane (1.77 g) was added, and the mixture was stirred at room temperature for 1 hour. To the obtained reaction mixture, a mixture of 3-(but-3-en-1-yl)cyclopent-2-en-1-one (2.0 g) and toluene (12 ml; used after being bubbled with argon gas over 30 minutes) was added, and the resulting mixture was stirred at room temperature for 13 hours. The obtained reaction mixture was diluted with THF (30 ml), and a 3 M aqueous sodium hydroxide solution (20 ml) was added thereto under ice cooling. The obtained reaction mixture was warmed to room temperature and stirred for 2 hours, and water was then added thereto, followed by extraction with Et$_2$O. The obtained organic layer was dried over anhydrous magnesium sulfate and then concentrated to approximately 15 ml under reduced pressure. The obtained mixture was purified by silica gel column chromatography (hexane/Et$_2$O) to obtain (3S)-3-(but-3-en-1-yl)cyclopentanone (1.20 g) as an oil.

Production Example 40

A mixture of [(4R)-4,4'-bi-1,3-benzodioxole-5,5'-diyl]bis[bis(3,5-di-tert-butyl-4-methoxyphenyl)phosphine] (621 mg), copper(II) acetate monohydrate (105 mg), and toluene (25 ml; used after being bubbled with argon gas for 30 minutes or longer) was stirred at room temperature for 2 hours under an argon atmosphere. To the obtained reaction mixture, polymethylhydrosiloxane (4.23 g) was added, and the mixture was stirred at room temperature for 1 hour. To the obtained reaction mixture, a mixture of 3-(but-3-en-1-yl)cyclopent-2-en-1-one (4.78 g) and toluene (28 ml; used after being bubbled with argon gas over 30 minutes) was added, and the resulting mixture was stirred at room temperature for 13 hours. The obtained reaction mixture was diluted with THF (70 ml), and a 3 M aqueous sodium hydroxide solution (50 ml) was added thereto under ice cooling. The obtained reaction mixture was warmed to room temperature and stirred for 2 hours, and water was then added thereto, followed by extraction with Et$_2$O. The obtained organic layer was dried over anhydrous magnesium sulfate and then concentrated to approximately 25 ml under reduced pressure. The obtained mixture was purified by silica gel column chromatography (hexane/Et$_2$O) to obtain (3R)-3-(but-3-en-1-yl)cyclopentanone (3.74 g) as an oil.

Production Example 41

A mixture of 4-methylpentanal (1.1 g), (2R,5R)-2,5-dimethylpyrrolidin-1-amine (1.29 g), CH$_2$Cl$_2$ (21.9 ml), and anhydrous magnesium sulfate (3.97 g) was stirred at room temperature for 2 hours. Insoluble matter was filtered off from the obtained reaction mixture, and the filtrate was concentrated under reduced pressure. The obtained residue was purified by silica gel column chromatography (hexane/AcOEt) to obtain (2R,5R)-2,5-dimethyl-N-[(1E)-4-methylpentylidene]pyrrolidin-1-amine (1.63 g) as an oil.

Production Example 42

A mixture of ethyl (5R)-5-(2-cyclopropylethyl)-6,7-dihydro-5H-cyclopenta[c]pyridine-1-carboxylate (1.41 g) and CH$_2$Cl$_2$ (35 ml) was cooled with ice. Then, m-chloroperbenzoic acid (containing approximately 25% water, 1.9 g) was added thereto, and the mixture was stirred at room temperature for 4 hours. To the obtained reaction mixture, a 10% aqueous sodium thiosulfate solution was added, and the mixture was stirred at room temperature for 30 minutes. The obtained reaction mixture was extracted with CHCl$_3$. The organic layer was washed sequentially with a saturated aqueous solution of sodium bicarbonate and a saturated aqueous solution of sodium chloride. The obtained organic layer was dried over anhydrous magnesium sulfate and then concentrated under reduced pressure. The obtained residue was purified by silica gel column chromatography (CHCl$_3$/MeOH) to obtain ethyl (5R)-5-(2-cyclopropylethyl)-6,7-dihydro-5H-cyclopenta[c]pyridine-1-carboxylate 2-oxide (1.5 g) as an oil.

Production Example 43

A mixture of (3R,4S)-3-(benzyloxy)-1-[(2R,5R)-2,5-dimethylpyrrolidin-1-yl]-4-(3-methylbutyl)azetidin-2-one (470 mg), MeOH (15.5 ml), and magnesium monoperoxyphthalate hexahydrate (1.3 g) was stirred at room temperature for 2 hours. To the obtained reaction mixture, water was added, followed by extraction with CHCl₃. The obtained organic layer was dried over anhydrous magnesium sulfate and then concentrated under reduced pressure. The obtained residue was purified by silica gel column chromatography (hexane/AcOEt) to obtain (3R,4S)-3-(benzyloxy)-4-(3-methylbutyl)azetidin-2-one (188 mg) as a solid.

Production Example 44

To a mixture of ethyl (5R)-5-(2-cyclopropylethyl)-6,7-dihydro-5H-cyclopenta[c]pyridine-1-carboxylate 2-oxide (1.5 g) and 1,2-dichloroethane (30 ml), dimethylcarbamoyl chloride (1.6 ml) was added under a nitrogen atmosphere, and the resulting mixture was stirred at room temperature for 30 minutes. To the obtained reaction mixture, trimethylsilyl cyanide (3 ml) was added, and the mixture was stirred at room temperature for 14 hours. To the obtained reaction mixture, a saturated aqueous solution of sodium bicarbonate was added, followed by extraction with CHCl₃. The obtained organic layer was washed with a saturated aqueous solution of sodium chloride, dried over anhydrous magnesium sulfate, and then concentrated under reduced pressure. The obtained residue was purified by silica gel column chromatography (hexane/AcOEt) to obtain ethyl (5R)-3-cyano-5-(2-cyclopropylethyl)-6,7-dihydro-5H-cyclopenta[c]pyridine-1-carboxylate (1.17 g) as an oil.

Production Example 45

To a mixture of ethyl (5R)-3-cyano-5-(2-cyclopropylethyl)-6,7-dihydro-5H-cyclopenta[c]pyridine-1-carboxylate (1.17 g) and MeOH (15 ml), a 1 M aqueous sodium hydroxide solution (10 ml) was added, and the resulting mixture was stirred at room temperature for 1 hour. To the obtained reaction mixture, 1 M hydrochloric acid (13 ml) and DOX (15 ml) were added, and the mixture was stirred at room temperature for 2 hours. The pH of the obtained reaction mixture was adjusted to approximately 7 with a 1 M aqueous sodium hydroxide solution and extracted with CHCl₃. The obtained organic layer was washed with a saturated aqueous solution of sodium chloride and dried over anhydrous magnesium sulfate. The obtained organic layer was concentrated under reduced pressure to obtain (5R)-5-(2-cyclopropylethyl)-3-(methoxycarbonyl)-6,7-dihydro-5H-cyclopenta[c]pyridine-1-carboxylic acid (990 mg) as an oil.

Production Example 46

A mixture of (5R)-5-(2-cyclopropylethyl)-3-(methoxycarbonyl)-6,7-dihydro-5H-cyclopenta[c]pyridine-1-carboxylic acid (990 mg), Cu₂O (25 mg), 1,10-phenanthroline (63 mg), quinoline (2 ml), and N-methyl-2-pyrrolidone (8 ml) was stirred at 190° C. for 10 minutes under microwave irradiation under a nitrogen atmosphere. The obtained reaction mixture was allowed to cool to room temperature, and water was then added thereto, followed by extraction with AcOEt. The obtained organic layer was washed with a saturated aqueous solution of sodium chloride and dried over anhydrous magnesium sulfate. The obtained organic layer was concentrated under reduced pressure, and the residue was purified by silica gel column chromatography (hexane/AcOEt) to obtain methyl (5R)-5-(2-cyclopropylethyl)-6,7-dihydro-5H-cyclopenta[c]pyridine-3-carboxylate (59 mg) as an oil.

Production Example 47

To a mixture of 2-({[tert-butyl(dimethyl)silyl]oxy}methyl)-5-hydroxy-4H-pyran-4-one (4 g), potassium carbonate (3 g), and DMF (40 ml), iodomethane (1.2 ml) was added, then DMF (20 ml) was added, and the resulting mixture was stirred at room temperature for 30 minutes. To the obtained reaction mixture, water was added, followed by extraction with AcOEt. The obtained organic layer was washed sequentially with water and a saturated aqueous solution of sodium chloride, and dried over anhydrous magnesium sulfate. The obtained organic layer was concentrated under reduced pressure, and the residue was purified by silica gel column chromatography (hexane/AcOEt) to obtain 2-({[tert-butyl(dimethyl)silyl]oxy}methyl)-5-methoxy-4H-pyran-4-one (5.32 g) as an oil.

To a solution of the obtained 2-({[tert-butyl(dimethyl)silyl]oxy}methyl)-5-methoxy-4H-pyran-4-one (5.32 g) in EtOH (100 ml), 28% aqueous ammonia solution (100 ml) was added, and the mixture was stirred at 60° C. for 8 hours. To the obtained reaction mixture, a saturated aqueous solution of potassium carbonate was added, followed by extraction with CHCl₃:isopropanol=10:1 mixed solution for three times. The obtained organic layer was washed sequentially with a saturated aqueous solution of sodium bicarbonate and a saturated aqueous solution of sodium chloride, and dried over anhydrous magnesium sulfate. The obtained organic layer was concentrated under reduced pressure, and the residue was purified by silica gel column chromatography (CHCl₃/MeOH) to obtain 2-({[tert-butyl(dimethyl)silyl]oxy}methyl)-5-methoxypyridin-4-ol (1.5 g) as a solid.

Production Example 48

To a solution of 2-({[tert-butyl(dimethyl)silyl]oxy}methyl)-5-methoxypyridin-4-ol (1 g) and Et₃N (1 ml) in CH₂Cl₂ (20 ml), trifluoromethanesulfonic anhydride (1 ml) was added under ice cooling under a nitrogen atmosphere, and the mixture was stirred at the same temperature as above for 1 hour. To the obtained reaction mixture, a saturated aqueous solution of sodium bicarbonate was added under ice cooling, followed by extraction with AcOEt. The obtained organic layer was dried over anhydrous magnesium sulfate and concentrated under reduced pressure. The residue was purified by silica gel column chromatography (hexane/AcOEt) to obtain 2-({[tert-butyl(dimethyl)silyl]oxy}methyl)-5-methoxypyridin-4-yl trifluoromethanesulfonate (1.35 g) as an oil.

Production Example 49

Under an argon atmosphere, a mixture of tert-butyl [(1S)-1-{(4R)-4-[(4-bromo-5-methylpyridin-2-yl)methyl]-2,2-dimethyl-5-oxo-1,3-dioxolan-4-yl}-3-methylbutyl]carbamate (77 mg), 3-methyl-1-butyne (0.05 ml), Et₃N (0.155 ml), DMF (0.77 ml), and bis(triphenylphosphine)palladium(II) dichloride (23 mg) was stirred at 90° C. for 30 minutes under microwave irradiation. To the obtained reaction mixture, water was added, followed by extraction with AcOEt. The obtained organic layer was washed with water twice and then washed with a saturated aqueous solution of sodium chloride. The organic layer was dried over anhydrous sodium sulfate, and then concentrated under reduced pressure. The obtained residue was purified by silica gel column chromatography (hexane/AcOEt) to obtain tert-butyl {(1S)-1-[(4R)-2,2-dimethyl-4-{[5-methyl-4-(3-methylbut-1-yn-1- yl)pyridin-2-yl]methyl}-5-oxo-1,3-dioxolan-4-yl]-3-methylbutyl}carbamate (68.8 mg) as a solid.

Production Example 50

To a solution of 2-({[tert-butyl(dimethyl)silyl]oxy}methyl)-5-cyclopropyl-4H-pyran-4-one (1.55 g) in EtOH (35 ml), 28% aqueous ammonia solution (35 ml) was added, and the mixture was stirred overnight at 60° C. The obtained reaction mixture was concentrated under reduced pressure, and the residue was purified by silica gel column chromatography (CHCl$_3$/MeOH). To the obtained compound, DMF (20 ml) was added, then Et$_3$N (2 ml), tert-butyl(chloro)dimethylsilane (2 g), and N,N-dimethylpyridin-4-amine (10 mg) were added under ice cooling, and the mixture was stirred at room temperature for 3 hours. To the obtained reaction mixture, Et$_3$N (4 ml) and tert-butyl(chloro)dimethylsilane (2 g) were further added at room temperature, and the mixture was stirred at room temperature for 2 hours.

To the obtained reaction mixture, water was added, followed by extraction with AcOEt. The obtained organic layer was washed sequentially with water and a saturated aqueous solution of sodium chloride, and dried over anhydrous magnesium sulfate. The obtained organic layer was concentrated under reduced pressure. To the residue, CHCl$_3$ (20 ml) and formic acid (0.5 ml) were added, and the mixture was stirred at room temperature for 4 hours. To the obtained reaction mixture, water was added, followed by extraction with AcOEt. The obtained organic layer was washed sequentially with water and a saturated aqueous solution of sodium chloride, and dried over anhydrous magnesium sulfate. The obtained organic layer was concentrated under reduced pressure, and the residue was purified by silica gel column chromatography (CHCl$_3$/MeOH) to obtain 2-({[tert-butyl(dimethyl)silyl]oxy}methyl)-5-cyclopropylpyridin-4-ol (733 mg) as a solid.

Production Example 51

To 4-benzyl-2,5-dimethylpyridine 1-oxide (334 mg), acetic anhydride (6 ml) was added, and the mixture was stirred at 85° C. for 1 hour. The obtained reaction mixture was allowed to cool to room temperature and then concentrated under reduced pressure. To the obtained residue, MeOH (6 ml) and potassium carbonate (500 mg) were added, and the mixture was stirred at room temperature for 1 hour. To the obtained reaction mixture, water was added, followed by extraction with CHCl$_3$. The obtained organic layer was dried over anhydrous magnesium sulfate and then concentrated under reduced pressure. The obtained residue was purified by basic silica gel column chromatography (hexane/AcOEt) to obtain (4-benzyl-5-methylpyridin-2-yl)methanol (175 mg) as a solid.

Production Example 52

A mixture of trimethylsilylacetylene (25 ml) and THF (170 ml) was cooled to −78° C. under a nitrogen atmosphere, and n-butyllithium (1.6 M solution in hexane, 115 ml) was added dropwise thereto. The obtained reaction mixture was stirred for 15 minutes under ice cooling and then cooled to −78° C. again. To the obtained reaction mixture, N,N,N',N',N'',N''-hexamethylphosphoric acid triamide (32 ml) was added, and the mixture was stirred at the same temperature as above for 30 minutes. Then, (2-bromoethyl)cyclopropane (27 g) was added dropwise thereto over 5 minutes or longer, and the mixture was stirred at the same temperature as above for 30 minutes. The obtained reaction mixture was warmed to room temperature and stirred for 16 hours. To the obtained reaction mixture, water was added under ice cooling, and the organic layer was separated. The obtained organic layer was washed with a saturated aqueous solution of sodium chloride, dried over anhydrous magnesium sulfate, and then concentrated under reduced pressure to obtain (4-cyclopropylbut-1-yn-1-yl)(trimethyl)silane (31.8 g) as an oil.

Production Example 53

A mixture of (3R,4S)-3-[(4-chloropyridin-2-yl)methyl]-4-isobutyl-3-(methoxymethoxy)-1-(methoxymethyl)azetidin-2-one (150 mg), 1-methoxy-2-vinylbenzene (0.57 ml), N-cyclohexyl-N-methylcyclohexanamine (0.12 ml), tris(dibenzylideneacetone)dipalladium (96.0 mg), bis(tri-tert-butylphosphine)palladium (107 mg), and DOX (3 ml) was stirred at 100° C. for 24 hours under a nitrogen atmosphere. The obtained reaction mixture was allowed to cool to room temperature. Basic silica gel was added thereto, and the mixture was then concentrated under reduced pressure. The obtained residue was purified by basic silica gel column chromatography (hexane/AcOEt) to obtain (3R,4S)-4-isobutyl-3-(methoxymethoxy)-1-(methoxymethyl)-3-({4-[(E)-2-(2-methoxyphenyl)vinyl]pyridin-2-yl}methyl)azetidin-2-one (139 mg) as an oil.

Production Example 54

A mixture of tert-butyl {(1S)-1-[(4R)-4-{[6-(benzyloxy)-5,6,7,8-tetrahydroisoquinolin-1-yl]methyl}-2,2-dimethyl-5-oxo-1,3-dioxolan-4-yl]-3-methylbutyl}carbamate (100 mg), PtO$_2$ (20 mg), and THF (2 ml) was stirred at room temperature for 30 hours under a hydrogen atmosphere. Insoluble matter was filtered off from the obtained reaction mixture, and the filtrate was then concentrated under reduced pressure. To the obtained residue, THF (2 ml) and PtO$_2$ (20 mg) were added, and the mixture was stirred at room temperature for 14 hours under a hydrogen atmosphere. Insoluble matter was filtered off from the obtained reaction mixture, and the filtrate was then concentrated under reduced pressure. The obtained residue was purified by silica gel column chromatography (hexane/AcOEt) to obtain tert-butyl {(1S)-1-[(4R)-4-{[6-(cyclohexylmethoxy)-5,6,7,8-tetrahydroisoquinolin-1-yl]methyl}-2,2-dimethyl-5-oxo-1,3-dioxolan-4-yl]-3-methylbutyl}carbamate (93.2 mg) as a solid.

Production Example 55

A mixture of (2R,5R)-2, 5-dimethyl-N-[(1E)-4-methylpentylidene]pyrrolidin-1-amine (1.62 g), Et$_3$N (9.2 ml), and toluene (48 ml) was heated to 80° C., and benzyloxyacetyl chloride (0.4 M solution in toluene, 83 ml) was added thereto over 4 hours with stirring. The reaction mixture was allowed to cool to room temperature, and a saturated aqueous solution of sodium bicarbonate was then added thereto, followed by extraction with AcOEt. The obtained organic layer was dried over anhydrous magnesium sulfate and then concentrated under reduced pressure. The obtained residue was purified by silica gel column chromatography (hexane/AcOEt) to obtain (3R,4S)-3-(benzyloxy)-1-[(2R,5R)-2,5-dimethylpyrrolidin-1-yl]-4-(3-methylbutyl)azetidin-2-one (2.02 g) as an oil.

Production Example 56

To a mixture of 4-chloro-2-(chloromethyl)pyridine (7 g) and THF (100 ml), sodium iodide (6.8 g, dried in vacuum at 30° C. for 7 hours and further at room temperature for 5 days) was added under a nitrogen atmosphere, and the resulting mixture was stirred at room temperature for 4 hours. To the reaction mixture, anhydrous sodium sulfate (3 g) dried in vacuum at 50° C. for 4 hours was added, and the mixture was further stirred for 30 minutes (mixture C).

A solution of (3R,4S)-4-isobutyl-3-(methoxymethoxy)-1-(methoxymethyl)azetidin-2-one (5 g) in THF (50 ml) was cooled with a dry ice-acetone bath under a nitrogen atmosphere, and LDA (1.12 M solution in hexane-THF, 25 ml) was slowly added thereto. The reaction mixture was stirred for 30 minutes while cooled with a dry ice-acetone bath. Then, mixture C was added dropwise thereto, and the resulting mixture was further stirred for 30 minutes. To the obtained reaction mixture, a saturated aqueous solution of ammonium chloride was added, and the mixture was then warmed to room temperature and extracted with AcOEt twice. The obtained organic layer was dried over anhydrous sodium sulfate and concentrated under reduced pressure. The obtained residue was purified by silica gel column chromatography (hexane/AcOEt) to obtain (3R,4S)-3-[(4-chloropyridin-2-yl)methyl]-4-isobutyl-3-(methoxymethoxy)-1-(methoxymethyl)azetidin-2-one (5.44 g) as an oil.

Production Example 57

To a mixture of (6-ethyl-6,7-dihydro-5H-cyclopenta[c]pyridin-1-yl)methanol (210 mg) and THF (6 ml), a mixture of $PBr_3$ (0.11 ml) and THF (1 ml) was added under ice cooling, and the resulting mixture was then stirred at room temperature for 2 hours. The obtained reaction mixture was poured into a mixture of a saturated aqueous solution of sodium bicarbonate and AcOEt under ice cooling, and the obtained mixture was stirred at room temperature for 30 minutes. The organic layer was separated, and the aqueous layer was extracted with AcOEt. The obtained organic layers were combined and dried over anhydrous magnesium sulfate. The obtained organic layer was diluted with toluene and then concentrated to approximately 10 ml under reduced pressure. Again, the obtained mixture was diluted with toluene and concentrated to approximately 5 ml under reduced pressure (mixture D). A mixture of (3R,4S)-4-isobutyl-3-(methoxymethoxy)-1-(methoxymethyl)azetidin-2-one (210 mg) and THF (3 ml) was cooled with a dry ice-acetone bath under a nitrogen atmosphere. LDA (1.09 M solution in hexane-THF, 1.3 ml) was added thereto with stirring, and the mixture was stirred for 25 minutes. To this reaction mixture, mixture D was added dropwise, and the resulting mixture was then stirred for 1 hour under a dry ice-acetone bath cooling. To the obtained reaction mixture, propionic acid (0.10 ml) was added, and the mixture was then warmed to 0° C. and stirred at the same temperature as above for 20 minutes. To the obtained reaction mixture, dimethylamine (2 M solution in THF, 0.91 ml) was added, and the mixture was then stirred for 20 minutes under ice cooling. To the obtained reaction mixture, a saturated aqueous solution of ammonium chloride was added, followed by extraction with AcOEt. The obtained organic layer was dried over anhydrous magnesium sulfate and then concentrated under reduced pressure to obtain a mixture containing two diastereomers of (3R,4S)-3-[(6-ethyl-6,7-dihydro-5H-cyclopenta[c]pyridin-1-yl)methyl]-4-isobutyl-3-(methoxymethoxy)-1-(methoxymethyl)azetidin-2-one. The obtained mixture was purified by silica gel column chromatography (hexane/AcOEt) to respectively obtain (1) a less polar diastereomer (136 mg) and (2) a more polar diastereomer (103 mg) as oils.

Production Example 58

To a mixture of (3R,4S)-3-[(4-bromo-5-methylpyridin-2-yl)methyl]-3-(methoxymethoxy)-1-(methoxymethyl)-4-{[(triisopropylsilyl)oxy]methyl}azetidin-2-one (2 g), (4-cyclopropylbut-1-yn-1-yl)(trimethyl)silane (1.8 g), $Et_3N$ (3.6 ml), DMF (20 ml), and bis(triphenylphosphine)palladium (II) dichloride (0.5 g), tetra-n-butylammonium fluoride (1 M solution in THF, 11 ml) was added under an argon atmosphere. The obtained mixture was divided into two portions, each of which was stirred at 90° C. for 1 hour under microwave irradiation. The obtained reaction mixtures were each allowed to cool to room temperature and then combined, and water was added thereto, followed by extraction with AcOEt. The obtained organic layer was washed sequentially with water, a saturated aqueous solution of sodium bicarbonate, and a saturated aqueous solution of sodium chloride. The obtained organic layer was dried over anhydrous magnesium sulfate and concentrated under reduced pressure. The obtained residue was purified by silica gel column chromatography (hexane/AcOEt) to obtain (3R,4S)-3-{[4-(4-cyclopropylbut-1-yn-1-yl)-5-methylpyridin-2-yl]methyl}-4-(hydroxymethyl)-3-(methoxymethoxy)-1-(methoxymethyl)azetidin-2-one (1.28 g) as an oil.

Production Example compounds shown in Tables to be described later were produced in the same manner as in the method described in any of the above Production Examples 1-58. Tables to be described later show the structure, physicochemical data and production method of the Production Example compounds.

TABLE 3

| Ex. | Str |
|---|---|
| 1 | 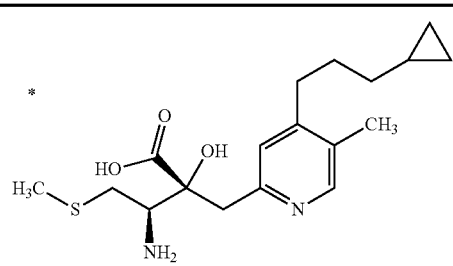 |
| 2 | 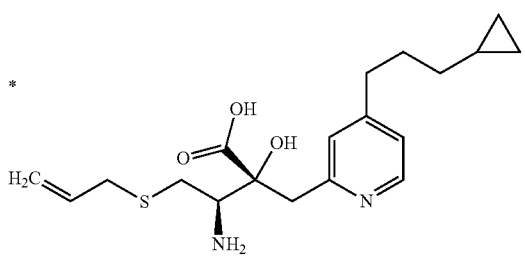 [SMILES: C=CCSC[C@H](N)[C@](O)(Cc1cc(CCCC2CC2)ccn1)C(=O)O] |

TABLE 3-continued

| Ex. | Str |
|---|---|
| 3 | (structure) |
| 4(1) | (structure) |
| 4(2) | (structure) |
| 4(3) | (structure) |
| 5 | (structure) 2HCl |
| 6(1) | (structure) |
| 6(2) | (structure) |
| 7 | (structure) 2HCl |

TABLE 4

| Ex. | Str |
|---|---|
| 8 | (structure) 2HCl |
| 9 | (structure) |

TABLE 4-continued
| Ex. | Str |
|---|---|
| 10(1) | $ 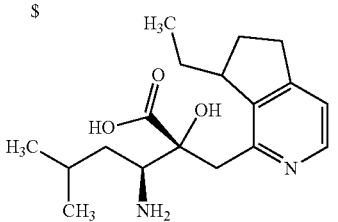 [SMILES: CCC1CCc2ccnc(C[C@](O)(C(=O)O)[C@@H](N)CC(C)C)c21] |
| 10(2) | $ 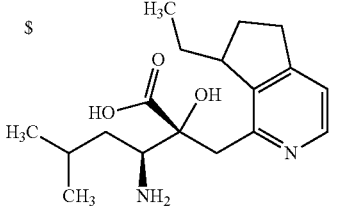 [SMILES: CCC1CCc2ccnc(C[C@](O)(C(=O)O)[C@@H](N)CC(C)C)c21] |
| 11 | #2  2HCl 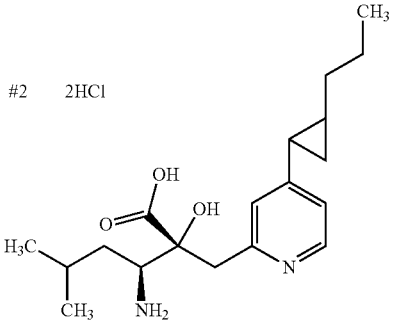 [SMILES: CCCC1CC1c1ccnc(C[C@](O)(C(=O)O)[C@@H](N)CC(C)C)c1] |
| 12 | * 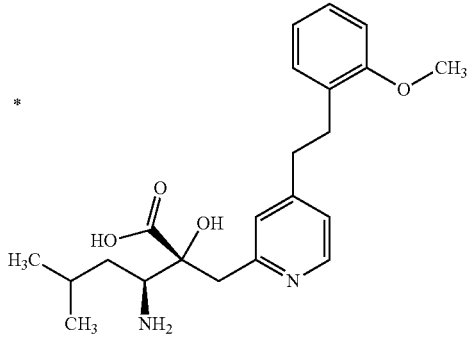 [SMILES: COc1ccccc1CCc1ccnc(C[C@](O)(C(=O)O)[C@@H](N)CC(C)C)c1] |
| 13 | * 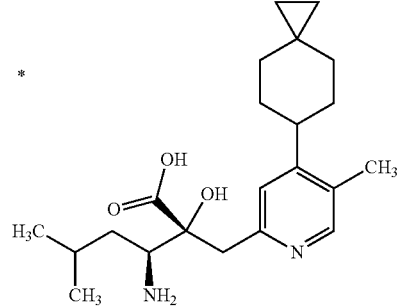 [SMILES: Cc1cnc(C[C@](O)(C(=O)O)[C@@H](N)CC(C)C)cc1C1CCC2(CC1)CC2] |
| 14 | * 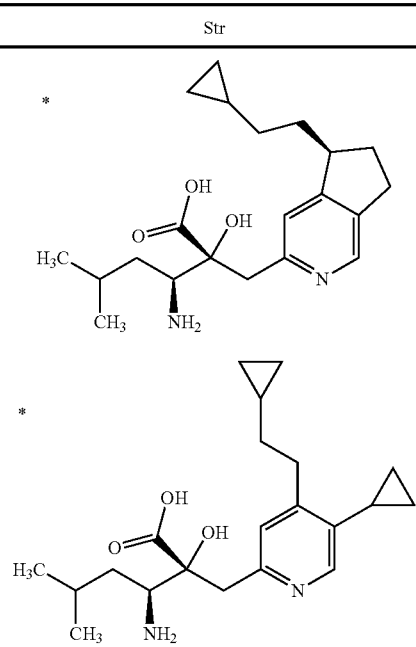 |
| 15 | * |
| 16 | * |
TABLE 5
| Ex. | Str |
|---|---|
| 17 | * |
| 18 | * |

TABLE 5-continued
| Ex. | Str |
|---|---|
| 19 | 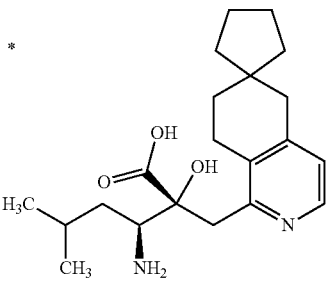 [SMILES: CC(C)C[C@H](N)[C@](O)(Cc1nccc2c1CCC1(CCCC1)C2)C(=O)O] |
| 20 #1 | 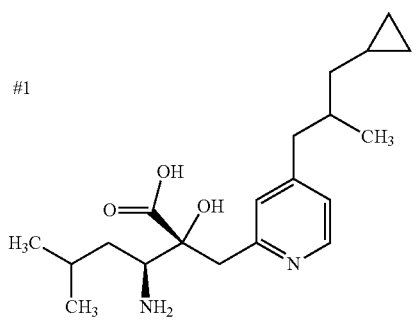 [SMILES: CC(C)C[C@H](N)[C@](O)(Cc1cc(CC(C)CC2CC2)ccn1)C(=O)O] |
| 21 * | 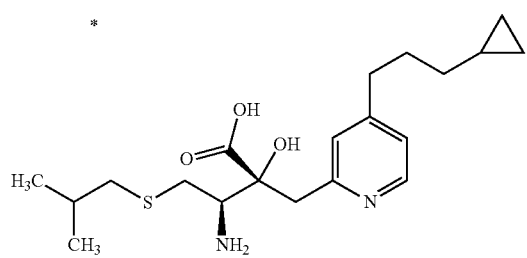 [SMILES: CC(C)CSC[C@H](N)[C@](O)(Cc1cc(CCCC2CC2)ccn1)C(=O)O] |
| 22 * | 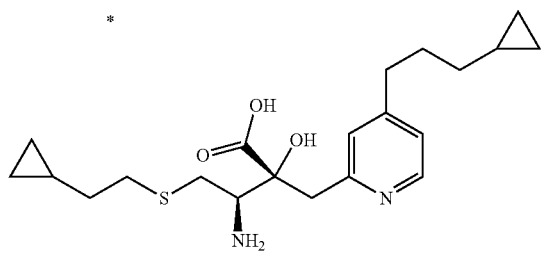 [SMILES: N[C@@H](CSCCC1CC1)[C@](O)(Cc1cc(CCCC2CC2)ccn1)C(=O)O] |
| 23 * | 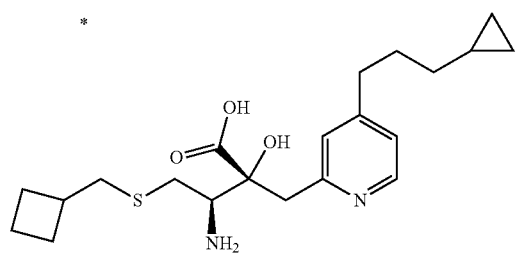 [SMILES: N[C@@H](CSCC1CCC1)[C@](O)(Cc1cc(CCCC2CC2)ccn1)C(=O)O] |
TABLE 5-continued
| Ex. | Str |
|---|---|
| 24 * | 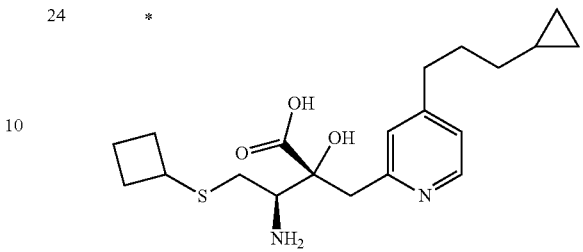 |
| 25 * | 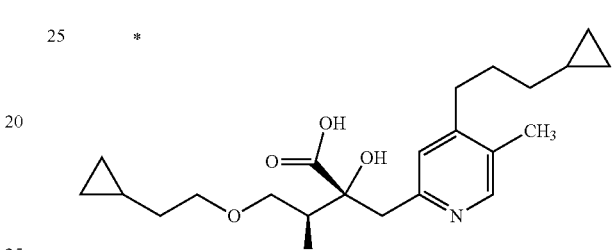 |
| 26 * | 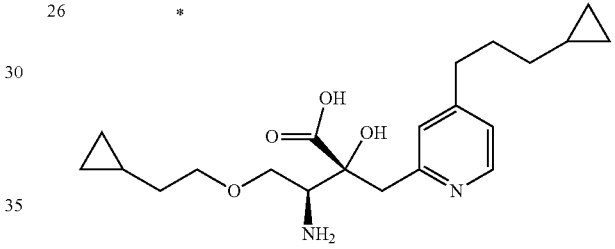 |
TABLE 6
| Ex. | Str |
|---|---|
| 27 * | 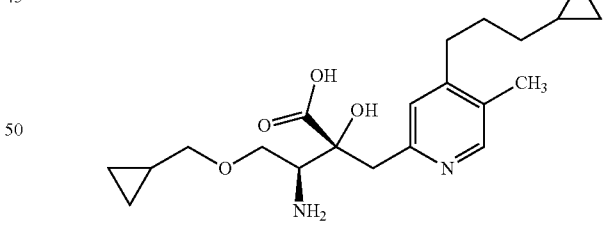 |
| 28 * | 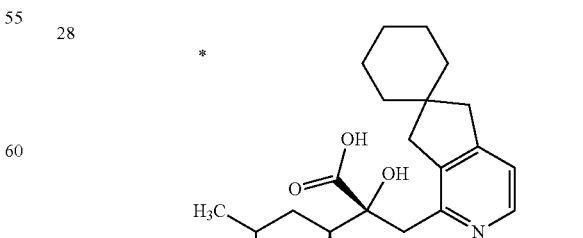 |

TABLE 6-continued

| Ex. | Str |
|---|---|
| 29 | (structure) |
| 30 | (structure) |
| 31 | (structure) |
| 32 | (structure) |
| 33 | (structure) |

TABLE 6-continued

| Ex. | Str |
|---|---|
| 34 | (structure) |
| 35 | (structure) |
| 36 | (structure) |

TABLE 7

| Ex. | Str |
|---|---|
| 37 | (structure) |
| 38 | (structure) |

TABLE 7-continued

| Ex. | Str |
|---|---|
| 39 | * (structure) |
| 40 | * (structure) |
| 41 | * (structure) |
| 42 | * (structure) |
| 43 | * (structure) |
| 44 | * (structure) |
| 45 | * (structure) |
| 46 | * (structure) |

TABLE 8

| Ex. | Str |
|---|---|
| 47 | * (structure) |

TABLE 8-continued

| Ex. | Str |
|---|---|
| 48 | (structure) |
| 49 | (structure) |
| 50 | (structure) #1 |
| 51 | (structure) #1 2HCl |
| 52 | (structure) * 2HCl |
| 53 | (structure) * 2HCl |
| 54 | (structure) * 2HCl |
| 55 | (structure) * 2HCl |
| 56 | (structure) * 2HCl |

TABLE 9
| Ex. | Str |
|---|---|
| 57 | 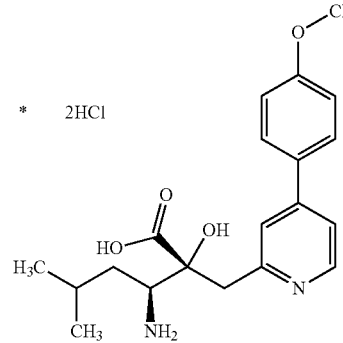 * 2HCl |
| 58 | 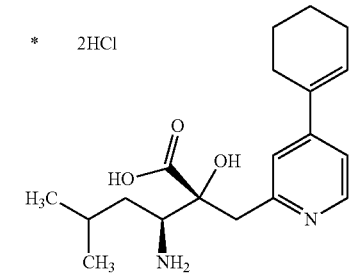 [SMILES: CC(C)C[C@H](N)[C@](O)(Cc1cc(C2=CCCCC2)ccn1)C(=O)O] * 2HCl |
| 59 | 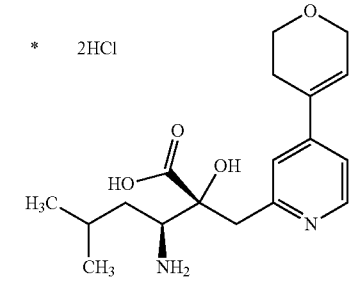 [SMILES: CC(C)C[C@H](N)[C@](O)(Cc1cc(C2=CCOCC2)ccn1)C(=O)O] * 2HCl |
| 60 | 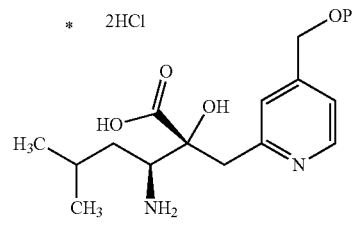 * 2HCl |
| 61 | 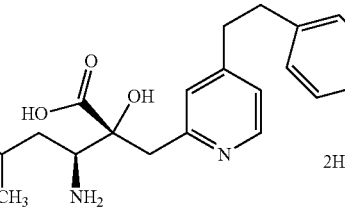 * 2HCl |
| 62 | 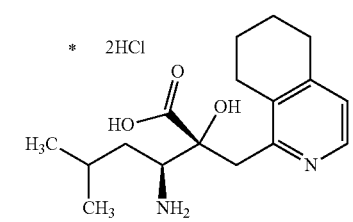 [SMILES: CC(C)C[C@H](N)[C@](O)(Cc1nccc2c1CCCC2)C(=O)O] * 2HCl |
TABLE 9-continued
| Ex. | Str |
|---|---|
| 63 | 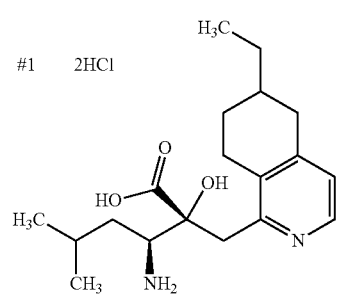 [SMILES: CCC1CCc2c(ccnc2C[C@](O)(C(=O)O)[C@@H](N)CC(C)C)C1] #1 2HCl |
| 64 | 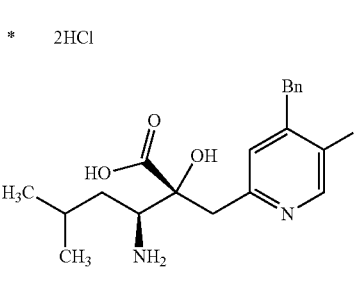 * 2HCl |
| 65 | 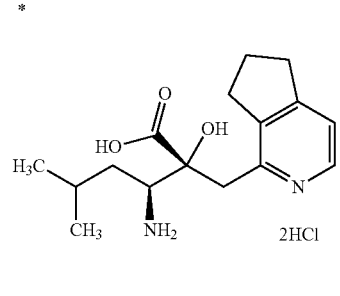 [SMILES: CC(C)C[C@H](N)[C@](O)(Cc1nccc2c1CCC2)C(=O)O] * 2HCl |
| 66 | 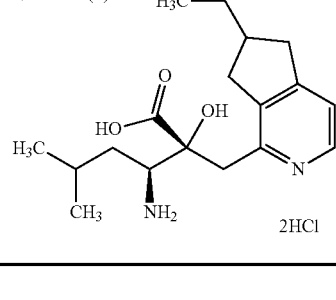 $-PEx 57(1) 2HCl |
TABLE 10
| Ex. | Str |
|---|---|
| 67 | 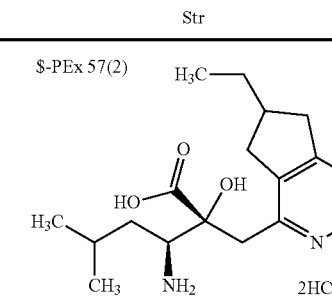 $-PEx 57(2) 2HCl |

TABLE 10-continued
| Ex. | Str |
|---|---|
| 68 | 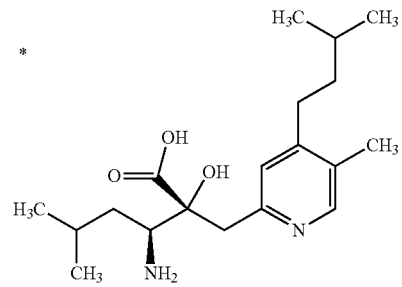 [SMILES: Cc1cnc(C[C@](O)(C(=O)O)[C@@H](N)CC(C)C)cc1CCC(C)C] |
| 69 | 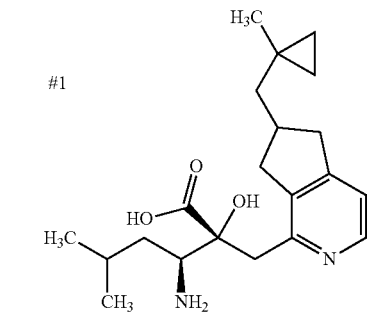 [SMILES: CC(C)C[C@H](N)[C@](O)(Cc1nccc2c1CC(CC1(C)CC1)C2)C(=O)O] |
| 70 | 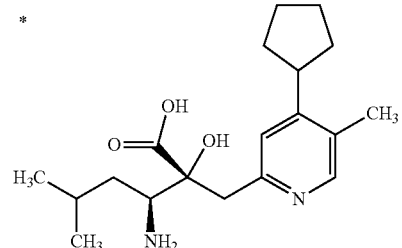 |
| 71 | 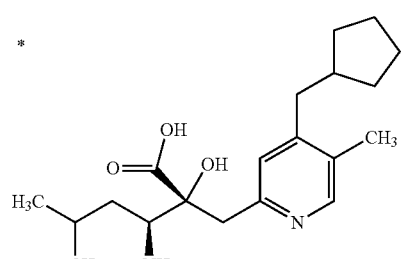 |
| 72 | 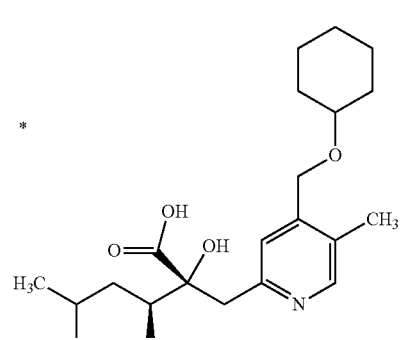 |
| 73 | 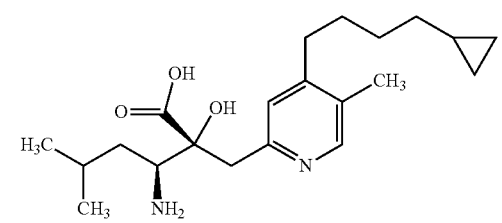 |
| 74 | 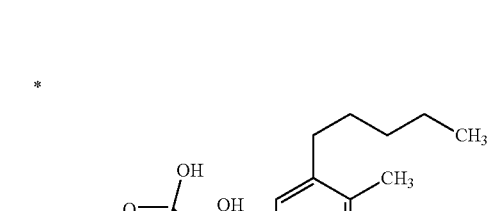 |
| 75 | 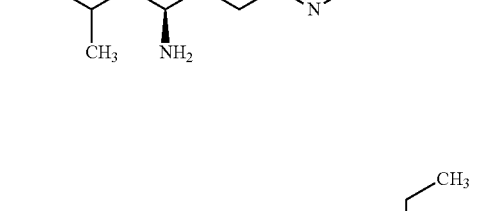 |
| 76 | 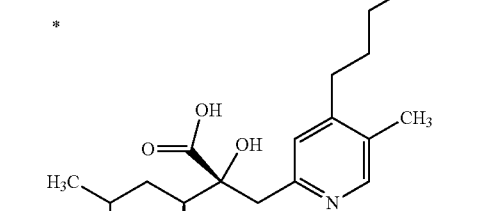 |

TABLE 11

| Ex. | Str |
|---|---|
| 77 | 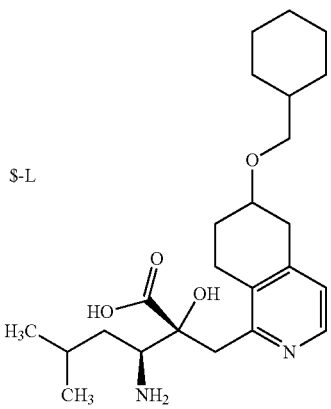 [SMILES: CC(C)C[C@H](N)[C@](O)(Cc1nccc2c1CCC(OCC1CCCCC1)C2)C(=O)O] $-L |
| 78 | 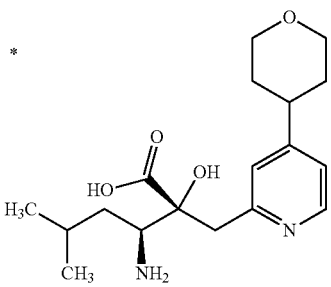 [SMILES: CC(C)C[C@H](N)[C@](O)(Cc1cc(C2CCOCC2)ccn1)C(=O)O] * |
| 79 | 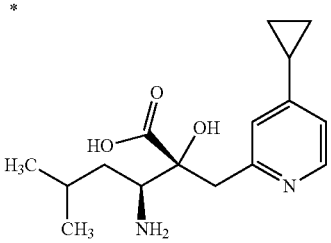 [SMILES: CC(C)C[C@H](N)[C@](O)(Cc1cc(C2CC2)ccn1)C(=O)O] * |
| 80 | 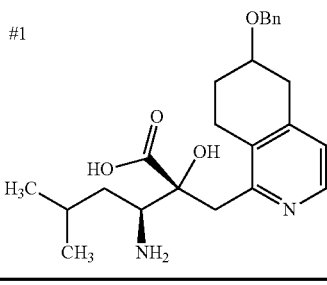 #1 |

TABLE 12

| Ex | Syn | DATA |
|---|---|---|
| 1 | — | ESI+: 353.1<br>$^1$H NMR (400 MHz, DMSO-d$_6$) δ ppm:<br>−0.01-0.04 (2H, m), 0.37-0.42 (2H, m), 0.66-0.77 (1H, m), 1.21-1.28 (2H, m), 1.56- 1.66 (2H, m), 1.97 (3H, s), 2.21 (3H, s), 2.31 (1H, dd, J = 14.3, 10.4 Hz), 2.55 (2H, dd, J = 8.8, 6.8 Hz), 2.89 (1H, d, J = 13.7 Hz), 2.93 (1H, dd, J = 14.5, 2.3 Hz), 3.05 (1H, dd, J = 10.6, 2.3 Hz), 3.11 (1H, d, J = 13.7 Hz), 7.05 (1H, s), 8.18 (1H, s) |
| 2 | — | ESI+: 365.1 |
| 3 | — | ESI+: 361.2<br>$^1$H NMR (500 MHz, DMSO-d$_6$) δ ppm:<br>−0.09-−0.02 (2H, m), −0.02-0.04 (2H, m), 0.28-0.35 (2H, m), 0.36-0.43 (2H, m), 0.50-0.58 (1H, m), 0.67-0.76 (1H, m), 1.04-1.13 (1H, m), 1.20-1.39 (4H, m), 1.57-1.65 (2H, m), 1.72-1.81 (1H, m), 2.21 (3H, s), 2.51-2.61 (2H, m), 2.79 (1H, dd, J = 9.0, 2.9 Hz), 2.82 (1H, d, J = 13.8 Hz), 3.09 (1H, d, J = 13.6 Hz), 7.04 (1H, s), 8.18 (1H, s) |
| 4(1) | — | ESI+: 349.2<br>$^1$H NMR (400 MHz, MeOH-d$_4$) δ ppm:<br>0.00-0.05 (2H, m), 0.39-0.47 (2H, m), 0.66-0.78 (1H, m), 0.83 (3H, d, J = 6.2 Hz), 0.94 (3H, d, J = 6.4 Hz), 1.27-1.34 (2H, m), 1.45 (1H, ddd, J = 13.9, 9.9, 3.5 Hz), 1.64 (1H, dd, J = 10.4, 2.6 Hz), 1.66-1.79 (3H, m), 2.29 (3H, s), 2.63-2.71 (2H, m), 3.04 (1H, dd, J = 9.7, 2.4 Hz), 3.08 (1H, d, J = 14.6 Hz), 3.19 (1H, d, J = 13.9 Hz), 7.18 (1H, s), 8.20 (1H, s) |
| 4(2) | — | ESI+: 385.3, 387.3 |
| 4(3) | — | ESI+: 367.3 |
| 5 | — | ESI+: 361.3<br>$^1$H NMR (400 MHz, MeOH-d$_4$) δ ppm:<br>0.03-0.09 (2H, m), 0.42-0.48 (2H, m), 0.67-0.77 (1H, m), 1.01 (3H, d, J = 6.2 Hz), 1.06 (3H, d, J = 6.4 Hz), 1.29-1.38 (2H, m), 1.64-1.89 (5H, m), 2.58-2.72 (1H, m), 2.89 (2H, ddd, J = 16.9, 15.3, 8.4 Hz), 3.26-3.42 (3H, m), 3.57 (1H, d, J = 14.1 Hz), 3.61-3.68 (1H, m), 7.80 (1H, d, J = 6.0 Hz), 8.49 (1H, d, J = 6.0 Hz) |
| 6(1) | — | ESI+: 347.2 |
| 6(2) | — | ESI+: 347.1 |
| 7 | — | ESI+: 349.2 |
| 8 | — | ESI+: 323.3 |
| 9 | — | ESI+: 361.2 |

TABLE 13

| Ex | Syn | DATA |
|---|---|---|
| 10(1) | — | ESI+: 321.2 |
| 10(2) | — | ESI+: 321.2 |
| 11 | — | ESI+: 335.3 |
| 12 | — | ESI+: 387.3 |
| 13 | 1 | ESI+: 375.3 |
| 14 | 1 | ESI+: 361.2 |
| 15 | 1 | ESI+: 365.3 |
| 16 | 1 | ESI+: 361.3 |
| 17 | 1 | ESI+: 361.3 |
| 18 | 1 | ESI+: 361.3 |
| 19 | 1 | ESI+: 361.3 |
| 20 | 1 | ESI+: 349.3 |
| 21 | 1 | ESI+: 381.3 |
| 22 | 1 | ESI+: 393.3 |
| 23 | 1 | ESI+: 393.3 |
| 24 | 1 | ESI+: 379.3 |
| 25 | 1 | ESI+: 391.2 |
| 26 | 1 | ESI+: 377.3 |
| 27 | 1 | ESI+: 377.3 |
| 28 | 1 | ESI+: 361.3 |
| 29 | 1 | ESI+: 379.2 |
| 30 | 1 | ESI+: 367.2 |
| 31 | 1 | ESI+: 361.2 |
| 32 | 1 | ESI+: 403.3 |
| 33 | 1 | ESI+: 403.2 |
| 34 | 1 | ESI+: 367.1 |
| 35 | 1 | ESI+: 367.2 |
| 36 | 1 | ESI+: 381.2 |
| 37 | 3 | ESI+: 468.1 |
| 38 | 3 | ESI+: 349.2 |
| 39 | 3 | ESI+: 361.3 |

TABLE 14

| Ex | Syn | DATA |
|---|---|---|
| 40 | 3 | ESI+: 347.2<br>$^1$H NMR (400 MHz, MeOH-d$_4$) δ ppm:<br>−0.02-0.05 (4H, m), 0.35-0.47 (4H, m), 0.58-0.76 (2H, m), |

TABLE 14-continued

| Ex | Syn | DATA |
|---|---|---|
| | | 1.17-1.30 (3H, m), 1.40 (1H, dddd, J = 13.5, 11.1, 6.6, 4.7 Hz), 1.52-1.64 (1H, m), 1.71-1.81 (2H, m), 2.03 (1H, dddd, J = 14.4, 11.1, 6.3, 3.3 Hz), 2.63-2.70 (2H, m), 2.98 (1H, dd, J = 9.3, 3.1 Hz), 3.08 (1H, d, J = 13.9 Hz), 3.25 (1H, d, J = 14.0 Hz), 7.14 (1H, dd, J = 5.1, 1.5 Hz), 7.21-7.24 (1H, m), 8.33 (1H, d, J = 5.1 Hz) |
| 41 | 3 | ESI+: 365.3<br>$^1$H NMR (400 MHz, MeOH-$d_4$) δ ppm:<br>0.00-0.07 (2H, m), 0.39-0.45 (2H, m), 0.65-0.75 (1H, m), 1.26-1.36 (2H, m), 1.60-1.69 (2H, m), 2.05 (3H, s), 2.43-2.60 (2H, m), 2.66 (1H, dd, J = 17.0, 8.4 Hz), 2.77 (1H, dd, J = 16.1, 8.2 Hz), 3.07-3.21 (4H, m), 3.24 (2H, s), 7.24 (1H, d, J = 5.2 Hz), 8.26 (1H, d, J = 5.2 Hz) |
| 42 | 3 | ESI+: 393.4<br>$^1$H NMR (400 MHz, MeOH-$d_4$) δ ppm:<br>0.00-0.06 (2H, m), 0.39-0.45 (2H, m), 0.64-0.75 (1H, m), 0.94 (3H, t, J = 7.4 Hz), 1.23-1.37 (2H, m), 1.45-1.69 (4H, m), 2.36-2.57 (4H, m), 2.63 (1H, dd, J = 16.5, 8.2 Hz), 2.76 (1H, dd, J = 16.1, 7.9 Hz), 3.02 (1H, dd, J = 11.2, 2.4 Hz), 3.05-3.28 (5H, m), 7.15 (1H, d, J = 5.1 Hz), 8.23 (1H, d, J = 5.1 Hz) |
| 43 | 3 | ESI+: 393.4 |
| 44 | 3 | ESI+: 365.1<br>$^1$H NMR (400 MHz, DMSO-$d_6$) δ ppm:<br>0.00-0.05 (2H, m), 0.36-0.41 (2H, m), 0.63-0.74 (1H, m), 1.21-1.29 (2H, m), 1.49-1.58 (2H, m), 1.96 (3H, s), 2.29-2.44 (2H, m), 2.51-2.59 (2H, m), 2.85-2.95 (2H, m), 3.01-3.19 (4H, m), 7.12 (1H, d, J = 5.1 Hz), 8.22 (1H, d, J = 5.1 Hz) |
| 45 | 3 | ESI+: 379.2 |
| 46 | 3 | ESI+: 393.2 |
| 47 | 3 | ESI+: 363.3 |
| 48 | 3 | ESI+: 369.3 |
| 49 | 4 | ESI+: 363.3 |
| 50 | 4 | ESI+: 381.3 |
| 51 | 5 | ESI+: 349.2 |

TABLE 15

| Ex | Syn | DATA |
|---|---|---|
| 52 | 5 | ESI+: 361.3<br>$^1$H NMR (400 MHz, MeOH-$d_4$) δ ppm:<br>0.03-0.08 (2H, m), 0.42-0.48 (2H, m), 0.67-0.78 (1H, m), 1.01 (3H, d, J = 6.4 Hz) 1.06 (3H, d, J = 6.4 Hz), 1.30-1.38 (2H, m), 1.63-1.88 (5H, m), 2.61-2.74 (1H, m), 2.79 (1H, dd, J = 16.3, 8.4 Hz), 2.90 (1H, dd, J = 18.3, 8.4 Hz), 3.24-3.45 (3H, m), 3.61 (1H, d, J = 13.9 Hz) 3.63-3.68 (1H, m), 7.80 (1H, d, J = 6.0 Hz), 8.49 (1H, d, J = 6.0 Hz) |
| 53 | 5 | ESI+: 335.3 |
| 54 | 5 | ESI+: 347.3 |
| 55 | 5 | ESI+: 347.3 |
| 56 | 7 | ESI+: 363.3 |
| 57 | 8 | ESI+: 359.1 |
| 58 | 8 | ESI+: 333.1 |
| 59 | 8 | ESI+: 335.1 |
| 60 | 8 | ESI+: 359.1 |
| 61 | 8 | ESI+: 371.3 |
| 62 | 8 | ESI+: 307.3 |
| 63 | 8 | ESI+: 335.3 |
| 64 | 8 | ESI+: 357.3 |
| 65 | 8 | ESI+: 293.2 |
| 66 | 8 | ESI+: 321.2 |
| 67 | 8 | ESI+: 321.2 |
| 68 | 9 | ESI+: 337.2 |
| 69 | 9 | ESI+: 361.2 |
| 70 | 9 | ESI+: 335.2 |
| 71 | 9 | ESI+: 349.2 |
| 72 | 9 | ESI+: 379.4 |
| 73 | 9 | ESI+: 363.3 |
| 74 | 9 | ESI+: 337.2 |
| 75 | 9 | ESI+: 351.3 |
| 76 | 10 | ESI+: 419.4 |
| 77 | 10 | ESI+: 419.4 |
| 78 | 12 | ESI+: 337.1 |

TABLE 15-continued

| Ex | Syn | DATA |
|---|---|---|
| 79 | 12 | ESI+: 293.2 |
| 80 | 9 | ESI+: 413.3 |

TABLE 16

| PEx | Str |
|---|---|
| 1 | |
| 2 | |
| 3 | |
| 4 | |

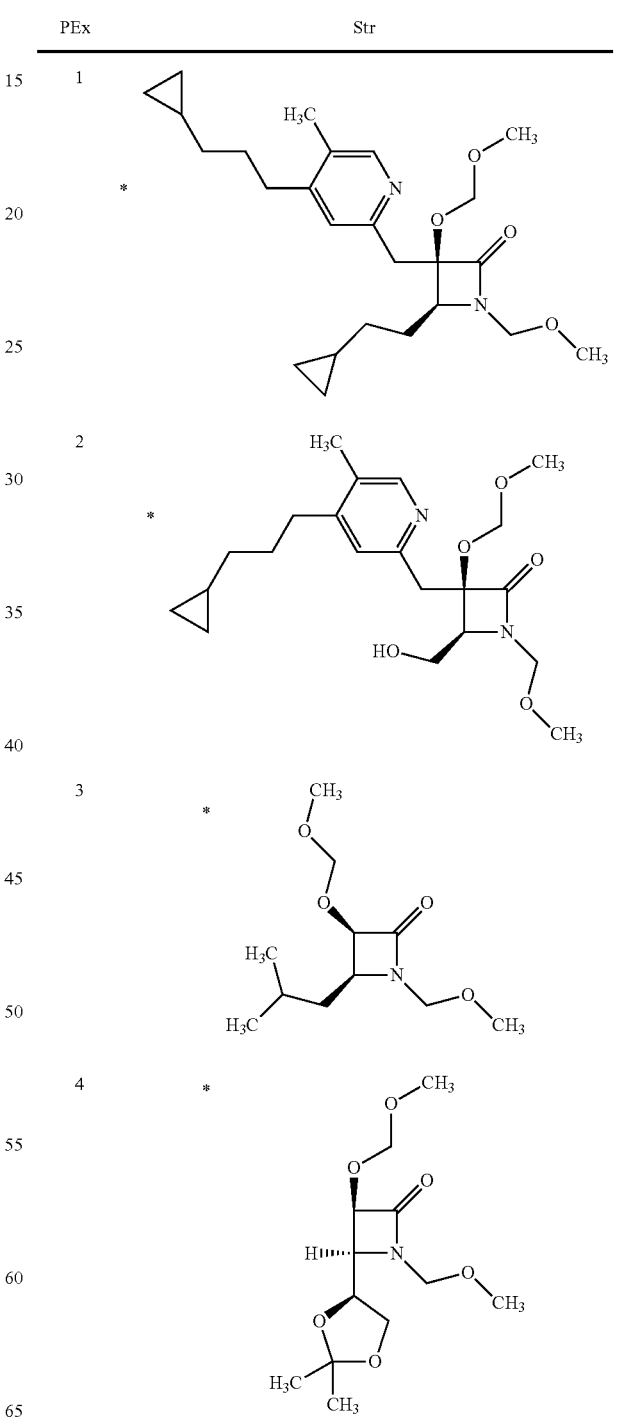

TABLE 16-continued
| PEx | Str |
|---|---|
| 5 | 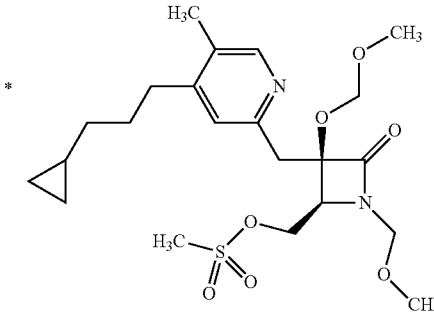 |
| 6 | 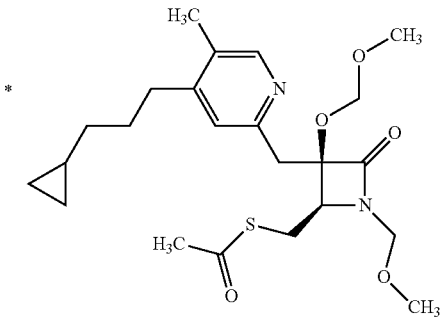 [SMILES: COCO[C@@]1(Cc2cc(CCCC3CC3)c(C)cn2)C(=O)N(COC)[C@H]1CSC(C)=O] |
| 7 | 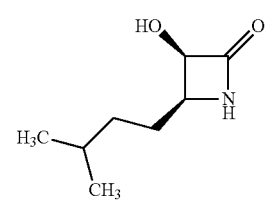 [SMILES: CC(C)CC[C@@H]1NC(=O)[C@@H]1OCc1ccccc1] |
| 8 | 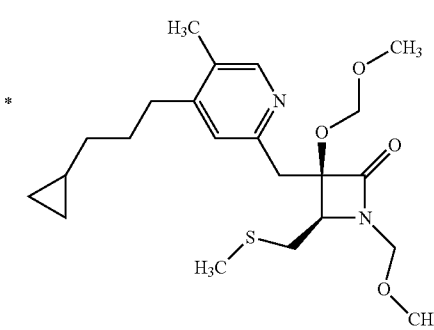 |
| 9 | 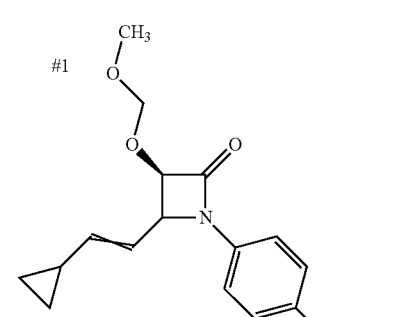 |
TABLE 16-continued
| PEx | Str |
|---|---|
| 10 | |
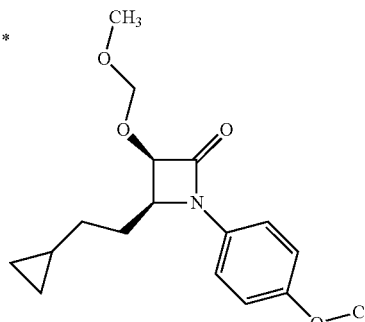
TABLE 17
| PEx | Str |
|---|---|
| 11 | |
| 12 | |
| 13 | |

TABLE 17-continued

| PEx | Str |
|---|---|
| 14 | (structure) |
| 15 | (structure) |
| 16 | (structure) |
| 17 | (structure) |
| 18 | (structure) |
| 19 | (structure) |
| 20 | (structure) |

TABLE 18

| PEx | Str |
|---|---|
| 21 | #1 (structure) |
| 22 | (structure) |
| 23 | (structure) |
| 24 | (structure) |
| 25 | (structure) |
| 26 | (structure) |

TABLE 18-continued

| PEx | Str |
|---|---|
| 27 | |
| 28 | |
| 29 | |
| 30 | |
| 31 | |
| 32 | |

TABLE 19

| PEx | Str |
|---|---|
| 33 | |
| 34 | |
| 35 | |
| 36(1) | |
| 36(2) | |
| 37 | |
| 38 | |
| 39 | |

TABLE 19-continued

| PEx | Str |
|---|---|
| 40 | |
| 41 | |
| 42 | |
| 43 | |

TABLE 20

| PEx | Str |
|---|---|
| 44 | |
| 45 | |

TABLE 20-continued

| PEx | Str |
|---|---|
| 46 | |
| 47 | |
| 48 | |
| 49 | |
| 50 | |
| 51 | |
| 52 | |

TABLE 20-continued

| PEx | Str |
|---|---|
| 53 | |
| 54 #1 | |
| 55 | |

TABLE 21

| PEx | Str |
|---|---|
| 56 | |
| 57(1) $-L | |
| 57(2) $-M | |
| 58 | |
| 59 | |
| 60 | |
| 61 | |
| 62 | |

TABLE 21-continued
| PEx | Str |
|---|---|
| 63 | 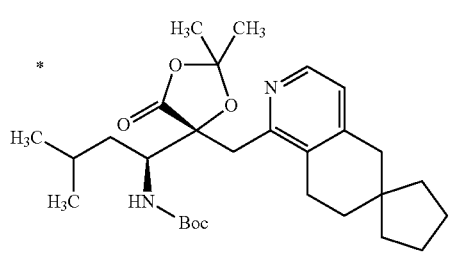 [SMILES: CC(C)C[C@H](NC(=O)OC(C)(C)C)[C@@]1(Cc2nccc3c2CCC2(CCCC2)C3)OC(C)(C)OC1=O] |
| 64 | 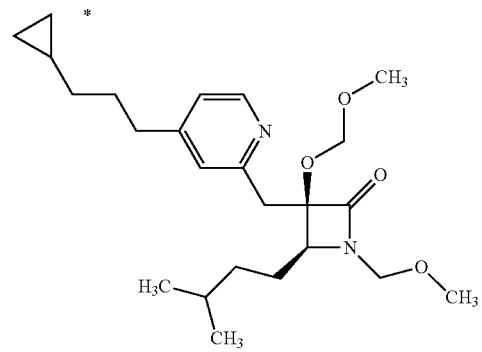 [SMILES: COCO[C@@]1(Cc2cc(CCCC3CC3)ccn2)C(=O)N(COC)[C@H]1CCC(C)C] |
TABLE 22
| PEx | Str |
|---|---|
| 65 | 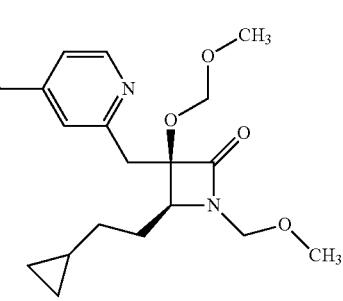 |
| 66 | * 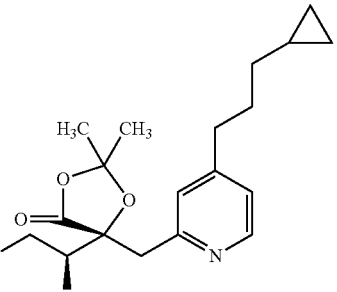 |
| 67 | * 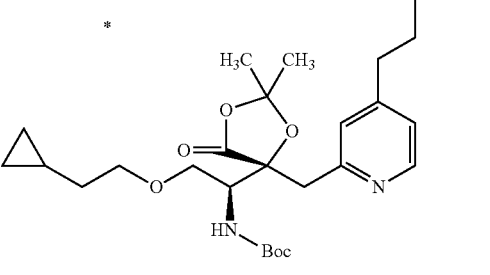 |
| 68 | 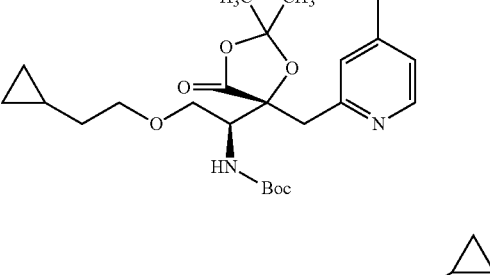 |
| 69 | 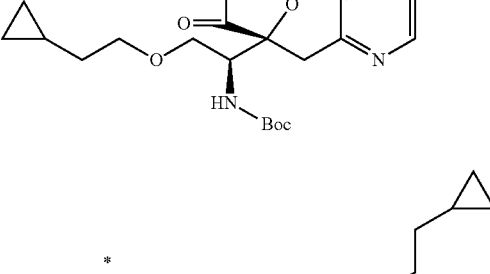 |
| 70 | 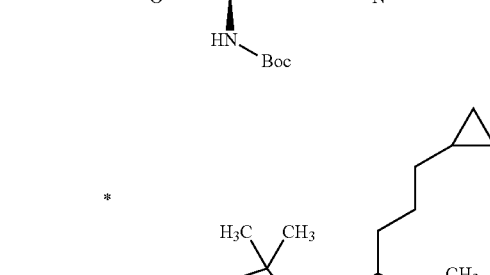 |
| 71 | 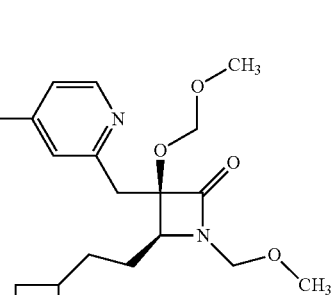 |

TABLE 22-continued
| PEx | Str |
|---|---|
| 72 | 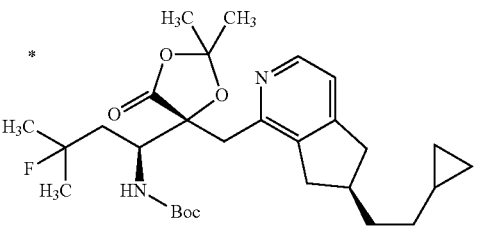 [SMILES: CC(C)(F)C[C@H](NC(=O)OC(C)(C)C)[C@@]1(Cc2nccc3c2C[C@H](CCC2CC2)C3)OC(C)(C)OC1=O] |
| 73 | 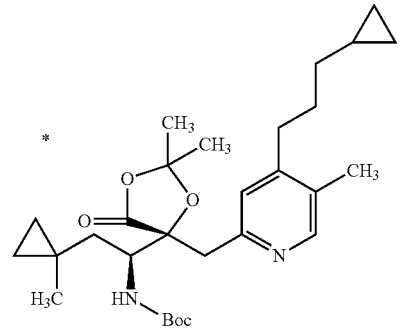 [SMILES: Cc1cnc(C[C@]2([C@H](CC3(C)CC3)NC(=O)OC(C)(C)C)OC(C)(C)OC2=O)cc1CCCC1CC1] |
| 74 | 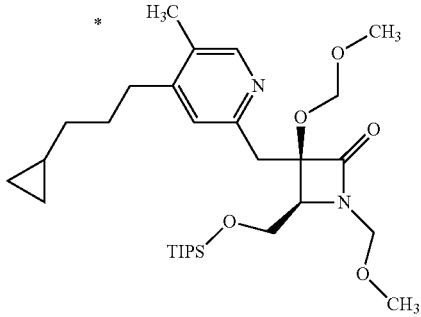 |
TABLE 23
| PEx | Str |
|---|---|
| 75 | 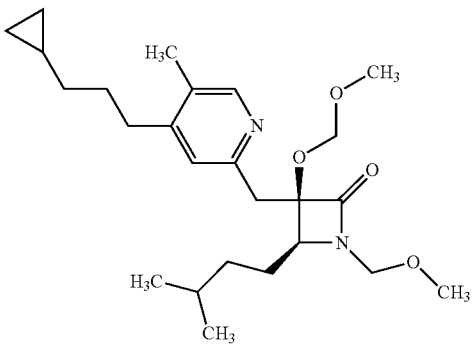 |
TABLE 23-continued
| PEx | Str |
|---|---|
| 76 | 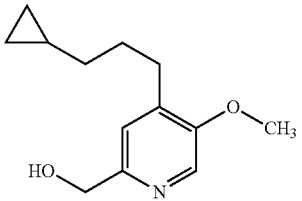 [SMILES: COc1cnc(CO)cc1CCCC1CC1] |
| 77 | 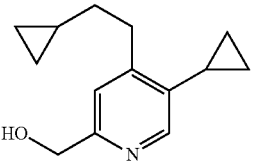 [SMILES: OCc1cc(CCC2CC2)c(C2CC2)cn1] |
| 78 | 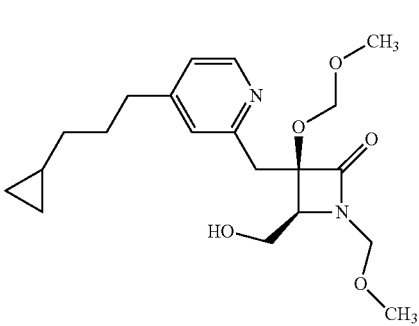 |
| 79 | 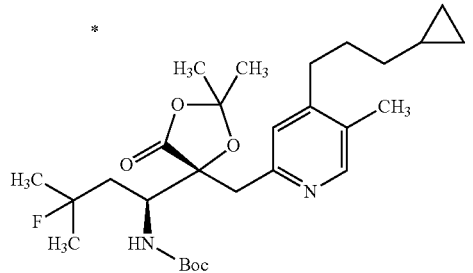 |
| 80 | 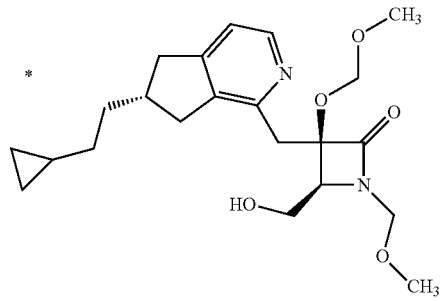 [SMILES: COCO[C@@]1(Cc2nccc3c2C[C@H](CCC2CC2)C3)C(=O)N(COC)[C@H]1CO] |

TABLE 23-continued
| PEx | Str |
|---|---|
| 81 | 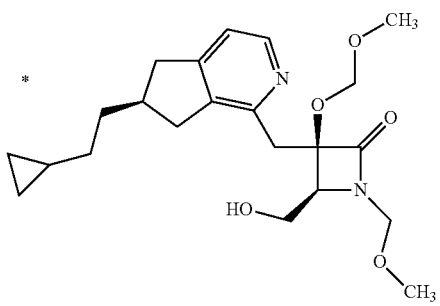 [SMILES: COCO[C@@]1(Cc2nccc3c2C[C@@H](CCC2CC2)C3)C(=O)N(COC)[C@H]1CO] |
| 82 | 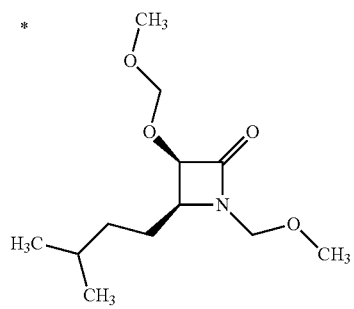 [SMILES: COCO[C@H]1C(=O)N(COC)[C@H]1CCC(C)C] |
| 83 | 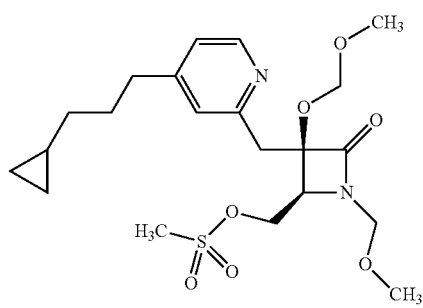 |
| 84 | 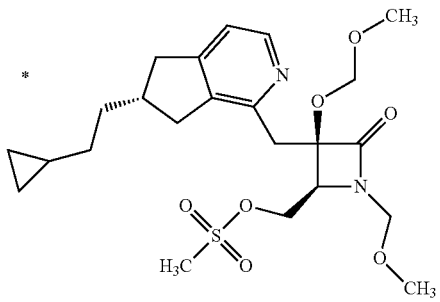 [SMILES: COCO[C@@]1(Cc2nccc3c2C[C@H](CCC2CC2)C3)C(=O)N(COC)[C@H]1COS(C)(=O)=O] |
TABLE 24
| PEx | Str |
|---|---|
| 85 | 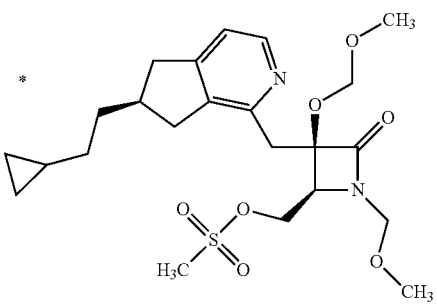 [SMILES: COCO[C@@]1(Cc2nccc3c2C[C@@H](CCC2CC2)C3)C(=O)N(COC)[C@H]1COS(C)(=O)=O] |
| 86 | 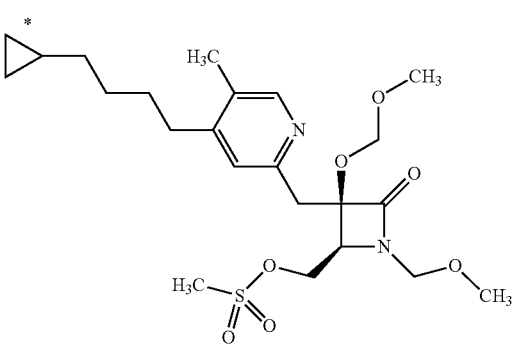 [SMILES: COCO[C@@]1(Cc2cc(CCCCC3CC3)c(C)cn2)C(=O)N(COC)[C@H]1COS(C)(=O)=O] |
| 87 | 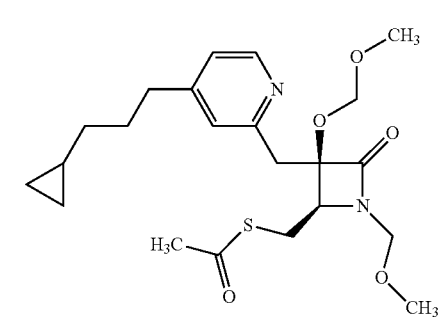 |
| 88 | 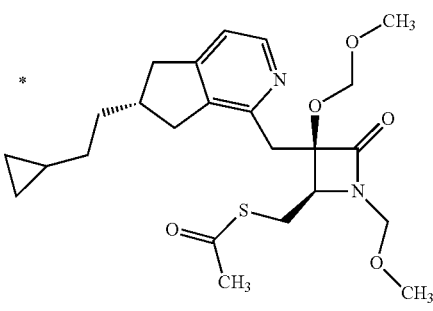 [SMILES: COCO[C@@]1(Cc2nccc3c2C[C@H](CCC2CC2)C3)C(=O)N(COC)[C@H]1CSC(C)=O] |

TABLE 24-continued
| PEx | Str |
|---|---|
| 89 | 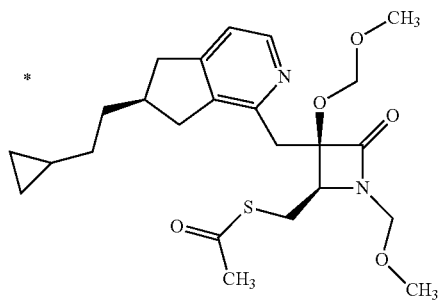 [SMILES: COCO[C@@]1(Cc2nccc3c2C[C@@H](CCC2CC2)C3)C(=O)N(COC)[C@H]1CSC(C)=O] |
| 90 | 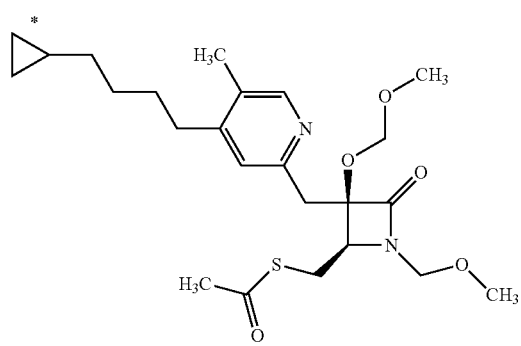 [SMILES: COCO[C@@]1(Cc2cc(CCCCC3CC3)c(C)cn2)C(=O)N(COC)[C@H]1CSC(C)=O] |
| 91 * | 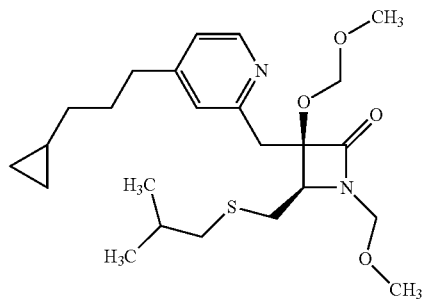 |
| 92 * | 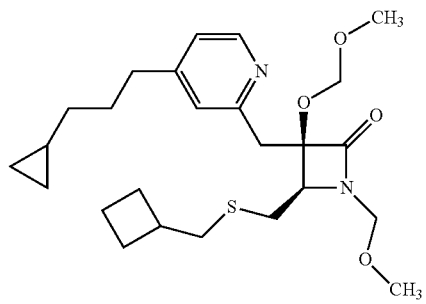 |
TABLE 24-continued
| PEx | Str |
|---|---|
| 93 * | 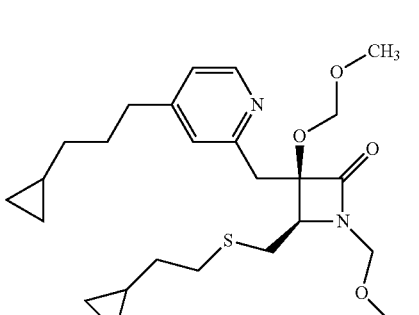 |
| 94 * | 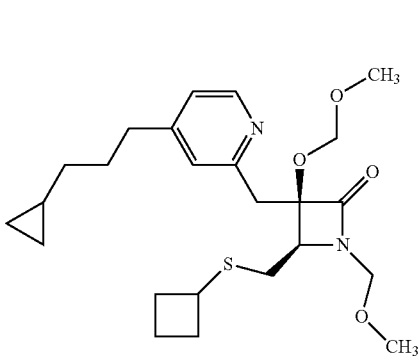 |
TABLE 25
| PEx | Str |
|---|---|
| 95 * | 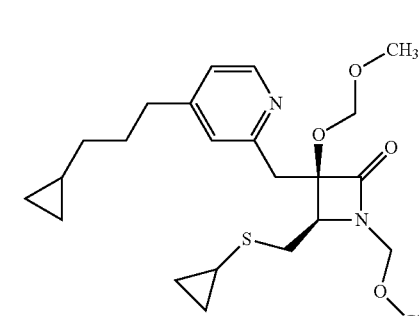 |
| 96 * | 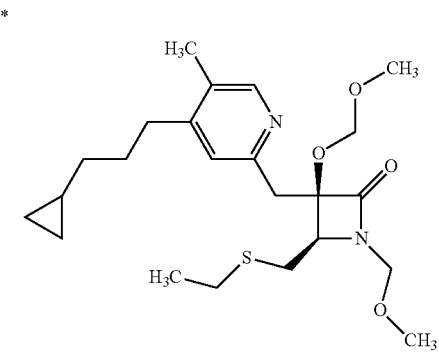 [SMILES: CCSC[C@@H]1N(COC)C(=O)[C@]1(Cc1cc(CCCC2CC2)c(C)cn1)OCOC] |

TABLE 25-continued

| PEx | Str |
|---|---|
| 97 | (structure) |
| 98 | (structure) |
| 99 | (structure) |
| 100 | (structure) |
| 101 | (structure) |
| 102 | (structure) |
| 103 | (structure) |
| 104 | (structure) |

TABLE 26

| PEx | Str |
|---|---|
| 105 | #1 (structure) |
| 106 | * (structure) |

TABLE 26-continued
| PEx | Str |
|---|---|
| 107 | 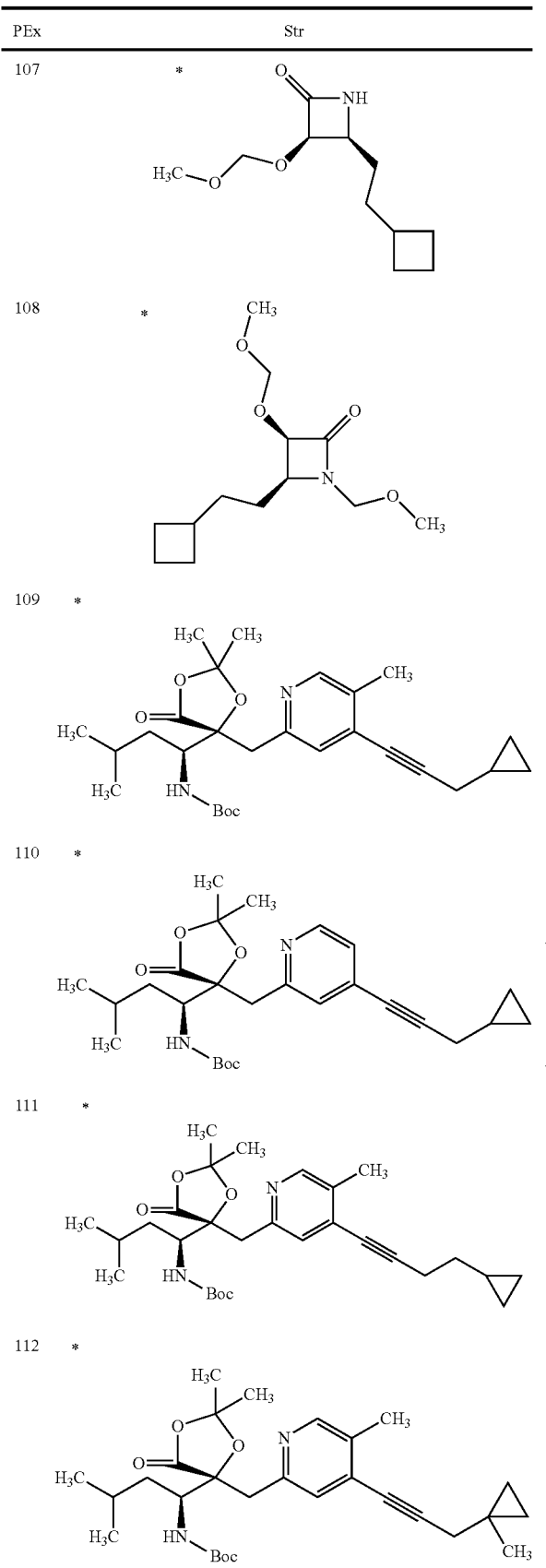 |
| 108 | |
| 109 | |
| 110 | |
| 111 | |
| 112 | |
TABLE 26-continued
| PEx | Str |
|---|---|
| 113 | 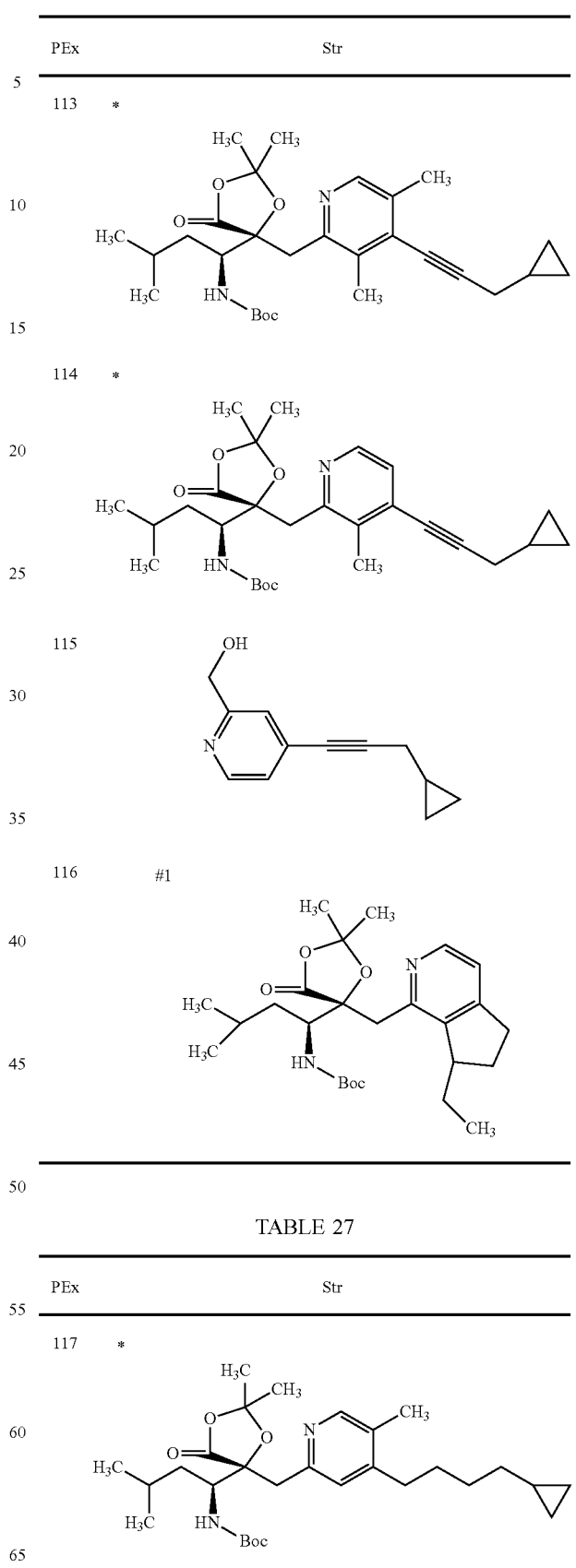 |
| 114 | |
| 115 | |
| 116 #1 | |
TABLE 27
| PEx | Str |
|---|---|
| 117 | |

TABLE 27-continued
| PEx | Str |
|---|---|
| 118 | 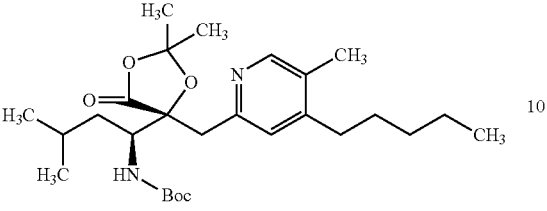 |
| 119 | 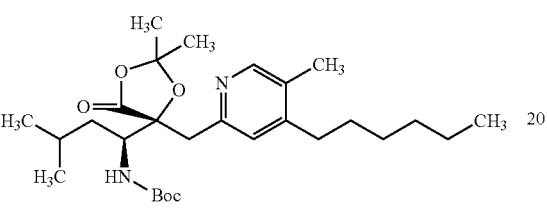 |
| 120 | 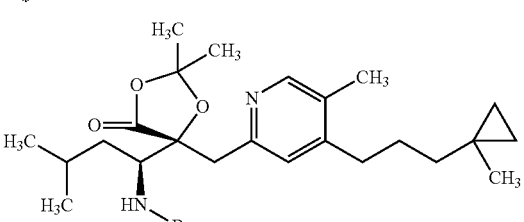 |
| 121 | 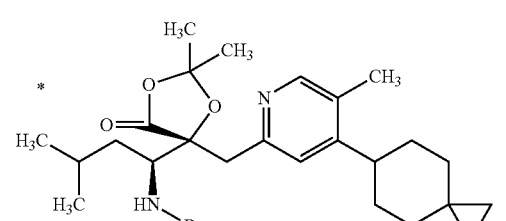 |
| 122 | 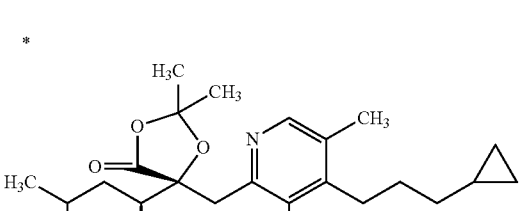 |
| 123 | 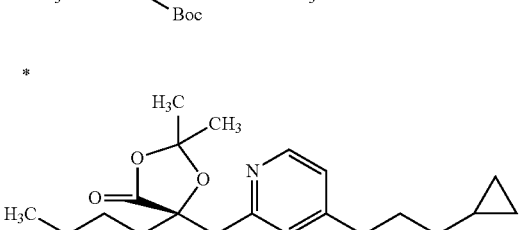 |
| 124 | 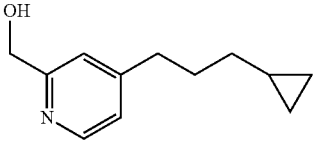 [SMILES: OCc1cc(CCCC2CC2)ccn1] |
| 125 | 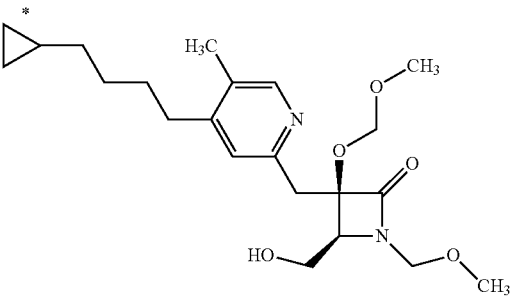 [SMILES: COCO[C@@]1(Cc2cc(CCCCC3CC3)c(C)cn2)C(=O)N(COC)[C@H]1CO] |
| 126 | 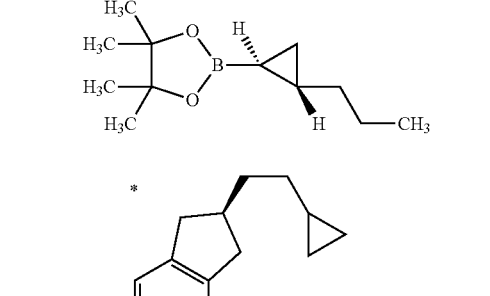 |
| 127 | 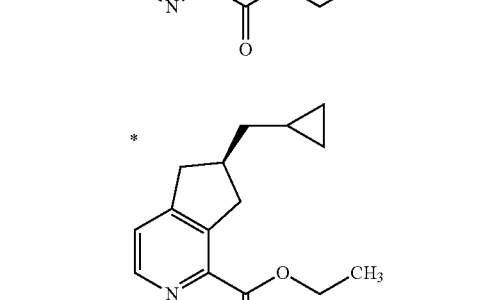 |
| 128 | 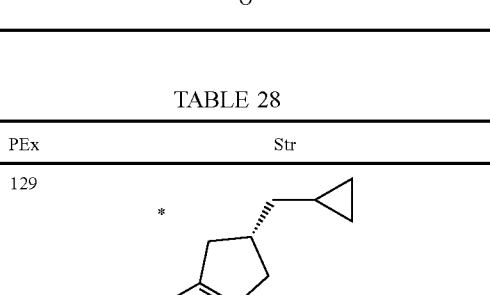 |
TABLE 28
| PEx | Str |
|---|---|
| 129 | 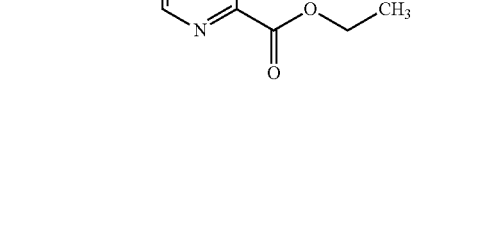 |

TABLE 28-continued
| PEx | Str |
|---|---|
| 130 | 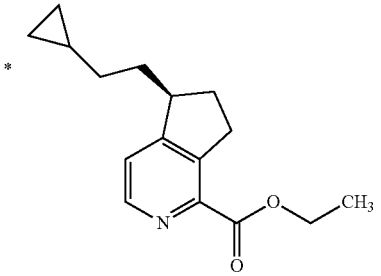 [SMILES: CCOC(=O)c1nccc2c1CC[C@@H]2CCC1CC1] |
| 131 | 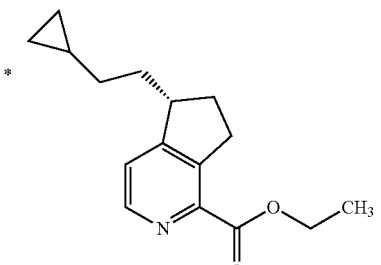 |
| 132 | 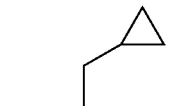 |
| 133 | 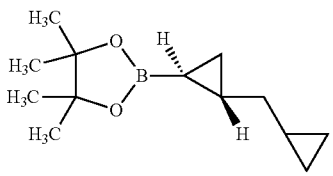 [SMILES: CC1(C)OB([C@H]2C[C@@H]2CC2CC2)OC1(C)C] |
| 134 | 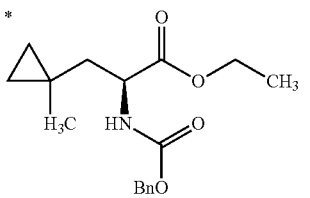 [SMILES: CCOC(=O)[C@H](CC1(C)CC1)NC(=O)OCc1ccccc1] |
| 135 | 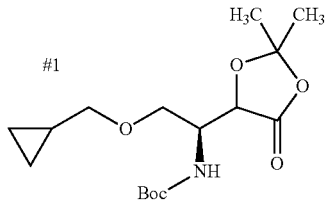 [SMILES: CC(C)(C)OC(=O)N[C@@H](COCC1CC1)C1OC(C)(C)OC1=O] |
TABLE 28-continued
| PEx | Str |
|---|---|
| 136 | 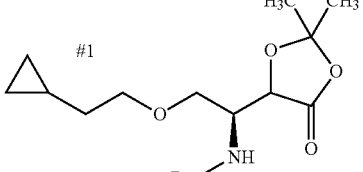 |
| 137 | 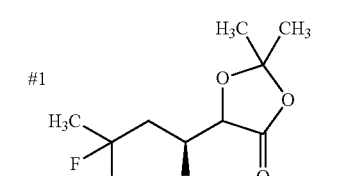 |
| 138 | 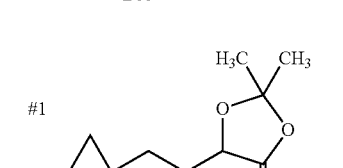 |
TABLE 29
| PEx | Str |
|---|---|
| 139 | 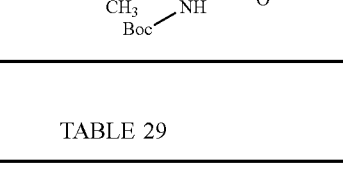 |
| 140 | 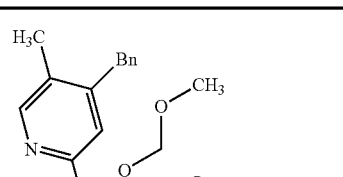 |

TABLE 29-continued
| PEx | Str |
|---|---|
| 141 | 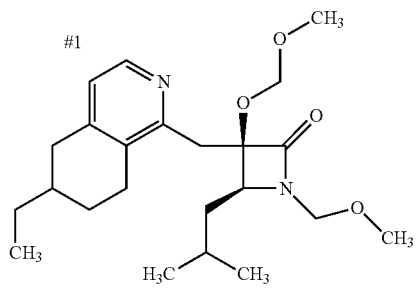 [SMILES: CCC1CCc2c(ccnc2C[C@]2(OCOC)C(=O)N(COC)[C@H]2CC(C)C)C1] #1 |
| 142 | 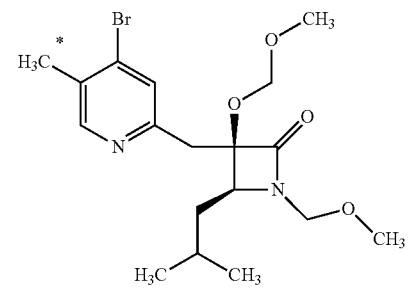 |
| 143 | 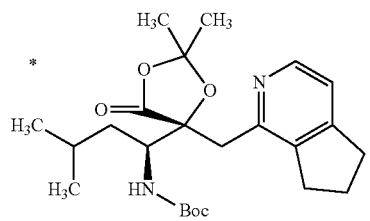 [SMILES: CC(C)C[C@H](NC(=O)OC(C)(C)C)[C@@]1(Cc2nccc3c2CCC3)OC(C)(C)OC1=O] |
| 144 | 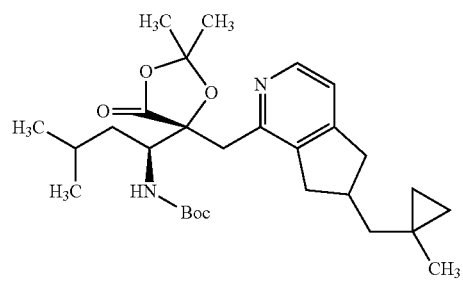 #1 |
| 145 | 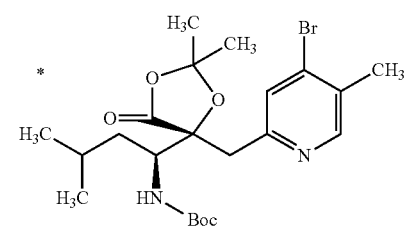 [SMILES: Cc1cnc(C[C@]2([C@H](CC(C)C)NC(=O)OC(C)(C)C)OC(C)(C)OC2=O)cc1Br] |
TABLE 29-continued
| PEx | Str |
|---|---|
| 146 | 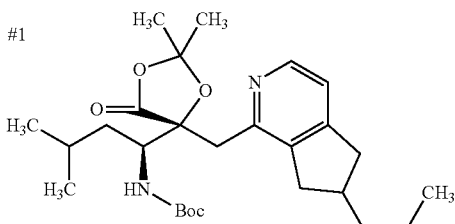 #1 |
| 147 | 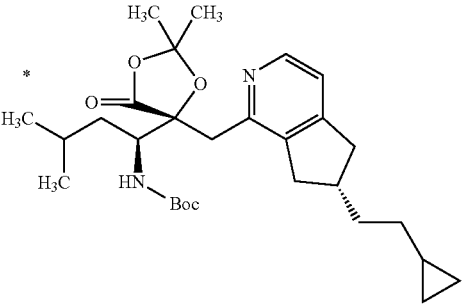 [SMILES: CC(C)C[C@H](NC(=O)OC(C)(C)C)[C@@]1(Cc2nccc3c2C[C@@H](CCC2CC2)C3)OC(C)(C)OC1=O] |
| 148 | 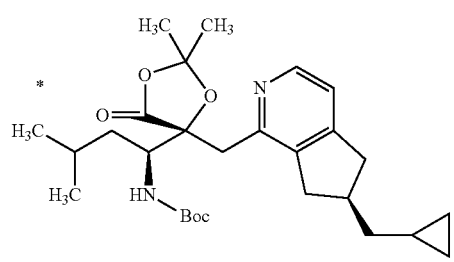 [SMILES: CC(C)C[C@H](NC(=O)OC(C)(C)C)[C@@]1(Cc2nccc3c2C[C@H](CC2CC2)C3)OC(C)(C)OC1=O] |
TABLE 30
| PEx | Str |
|---|---|
| 149 | 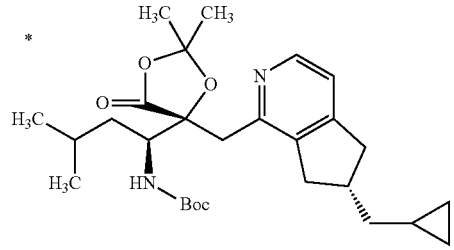 [SMILES: CC(C)C[C@H](NC(=O)OC(C)(C)C)[C@@]1(Cc2nccc3c2C[C@@H](CC2CC2)C3)OC(C)(C)OC1=O] |
| 150 | 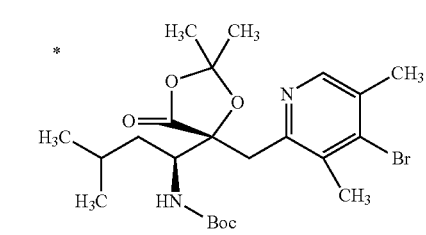 [SMILES: Cc1cnc(C[C@]2([C@H](CC(C)C)NC(=O)OC(C)(C)C)OC(C)(C)OC2=O)c(C)c1Br] |

TABLE 30-continued
| PEx | Str |
|---|---|
| 151 | 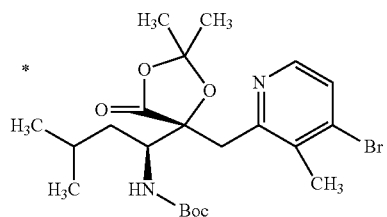 [SMILES: Cc1c(Br)ccnc1C[C@]1([C@H](CC(C)C)NC(=O)OC(C)(C)C)OC(C)(C)OC1=O] |
| 152 #1 | 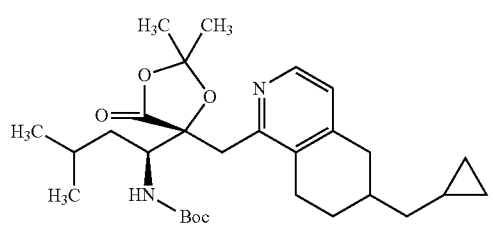 |
| 153 #1 | 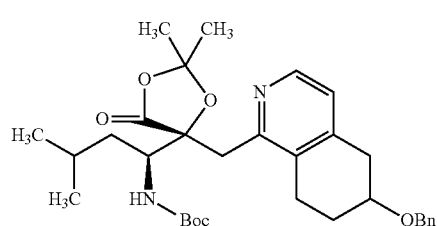 |
| 154 | 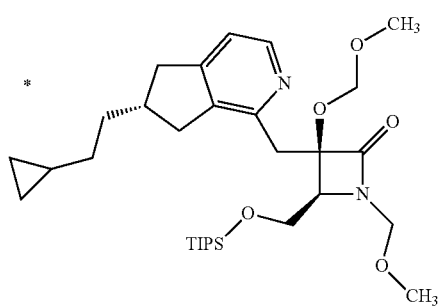 |
| 155 | 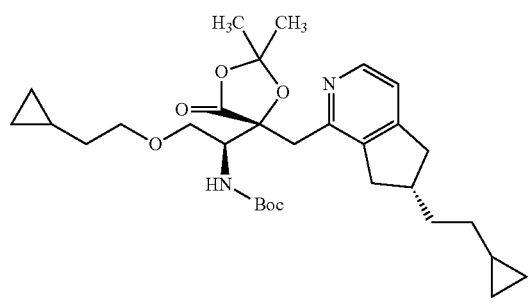 |
TABLE 30-continued
| PEx | Str |
|---|---|
| 156 | 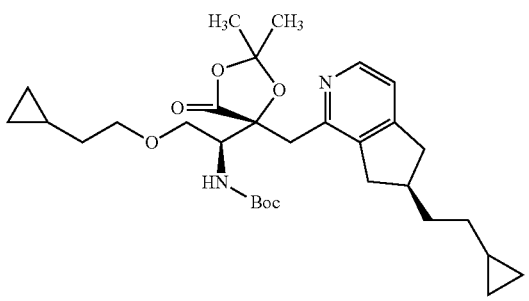 |
| 157 | 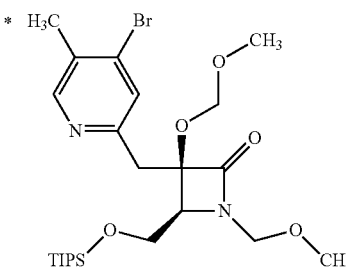 |
| 158 | 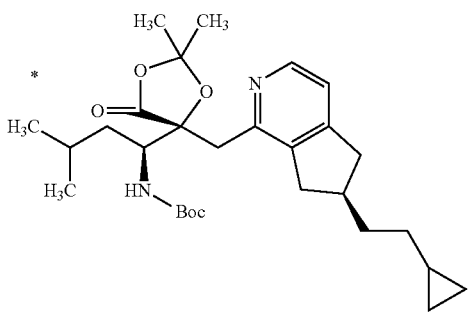 [SMILES: CC(C)C[C@H](NC(=O)OC(C)(C)C)[C@@]1(Cc2nccc3c2C[C@H](CCC2CC2)C3)OC(C)(C)OC1=O] |
TABLE 31
| PEx | Str |
|---|---|
| 159 | 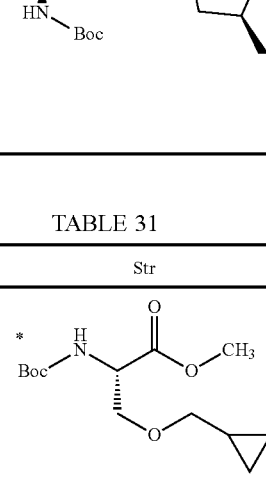 |
| 160 | 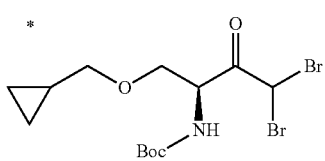 [SMILES: CC(C)(C)OC(=O)N[C@@H](COCC1CC1)C(=O)C(Br)Br] |
| 161 | 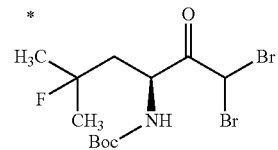 [SMILES: CC(C)(F)C[C@H](NC(=O)OC(C)(C)C)C(=O)C(Br)Br] |

TABLE 31-continued
| PEx | Str |
|---|---|
| 162 | 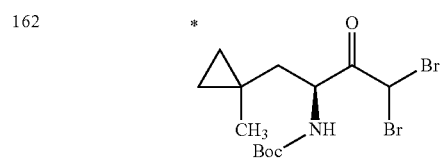 |
| 163 | 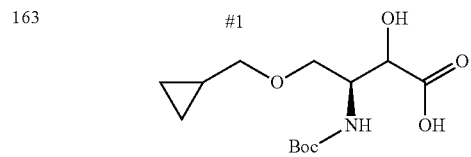 |
| 164 | 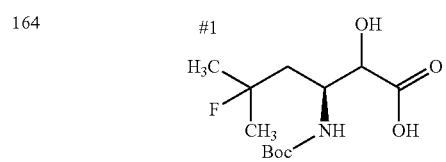 |
| 165 | 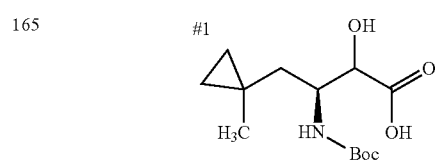 |
| 166 | 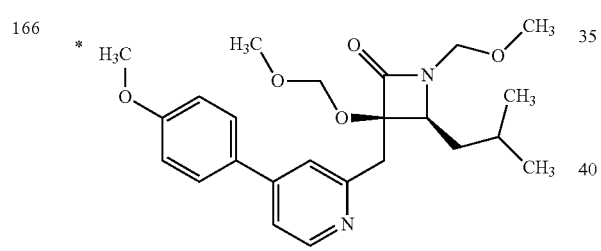 |
| 167 | 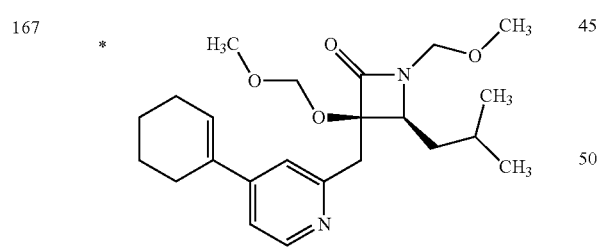 |
| 168 | 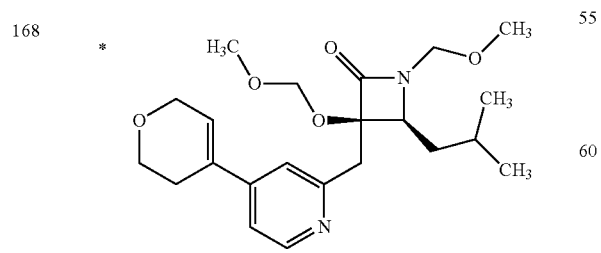 |
| 169 | 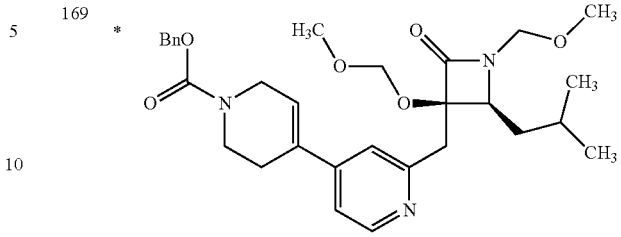 |
| 170 | 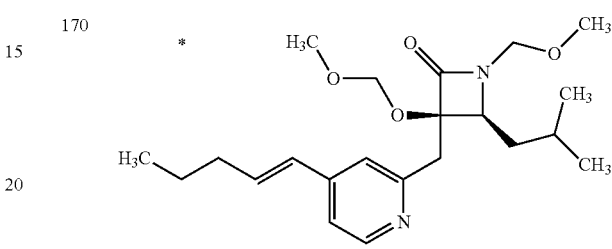 |
TABLE 32
| PEx | Str |
|---|---|
| 171 | 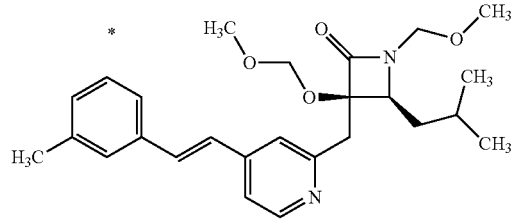 [SMILES: COCO[C@@]1(Cc2cc(/C=C/c3cccc(C)c3)ccn2)C(=O)N(COC)[C@H]1CC(C)C] |
| 172 | 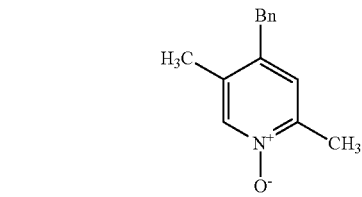 |
| 173 | 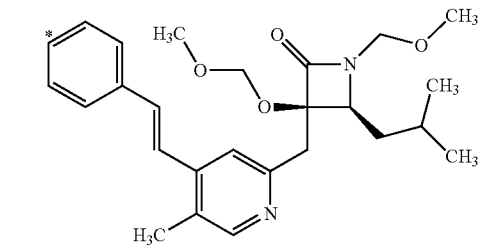 [SMILES: COCO[C@@]1(Cc2cc(/C=C/c3ccccc3)c(C)cn2)C(=O)N(COC)[C@H]1CC(C)C] |
| 174 | 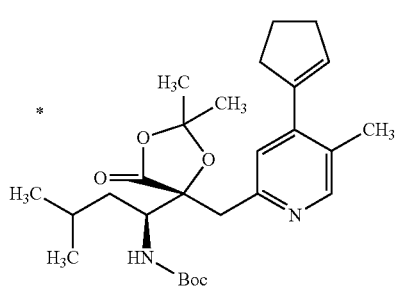 [SMILES: Cc1cnc(C[C@]2([C@H](CC(C)C)NC(=O)OC(C)(C)C)OC(C)(C)OC2=O)cc1C1=CCCC1] |

TABLE 32-continued
| PEx | Str |
|---|---|
| 175 | #2 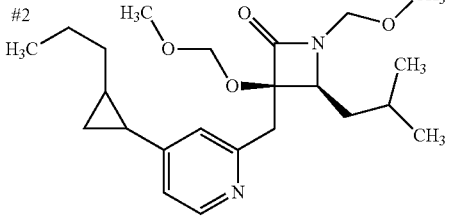 |
| 176 | 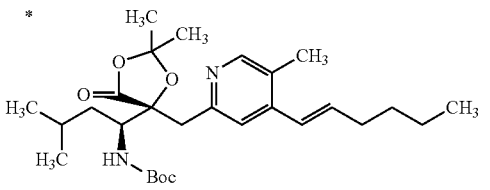 [SMILES: CCCC/C=C/c1cc(C[C@]2([C@H](CC(C)C)NC(=O)OC(C)(C)C)OC(C)(C)OC2=O)ncc1C] |
| 177 | 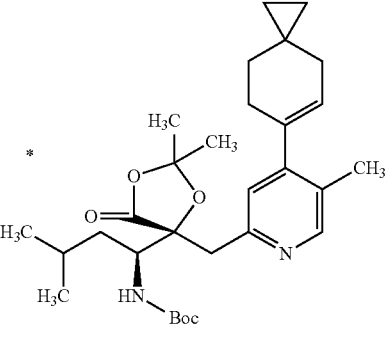 [SMILES: Cc1cnc(C[C@]2([C@H](CC(C)C)NC(=O)OC(C)(C)C)OC(C)(C)OC2=O)cc1C1=CCC2(CC1)CC2] |
| 178 | 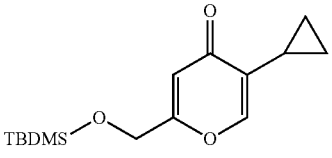 |
| 179 | #2 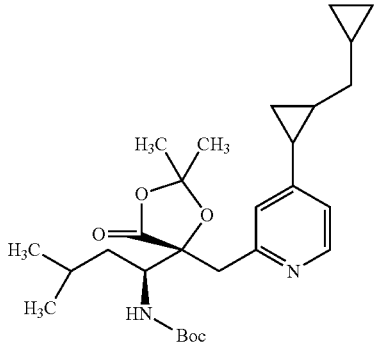 |
| 180 | 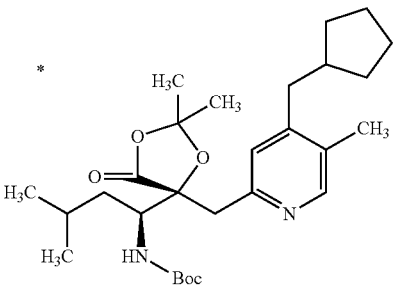 [SMILES: Cc1cnc(C[C@]2([C@H](CC(C)C)NC(=O)OC(C)(C)C)OC(C)(C)OC2=O)cc1CC1CCCC1] |
TABLE 33
| PEx | Str |
|---|---|
| 181 | |
| 182 | #1 |
| 183 | |
| 184 | |
| 185 | |

TABLE 33-continued
| PEx | Str |
|---|---|
| 186 | 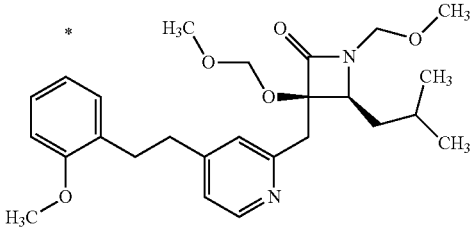 [SMILES: COCO[C@@]1(Cc2cc(CCc3ccccc3OC)ccn2)C(=O)N(COC)[C@H]1CC(C)C] |
| 187 | 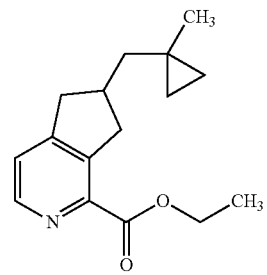 [SMILES: CCOC(=O)c1nccc2c1CC(CC1(C)CC1)C2] |
| 188 | 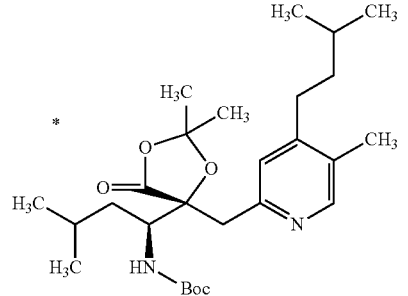 [SMILES: Cc1cnc(C[C@]2([C@H](CC(C)C)NC(=O)OC(C)(C)C)OC(C)(C)OC2=O)cc1CCC(C)C] |
| 189 | 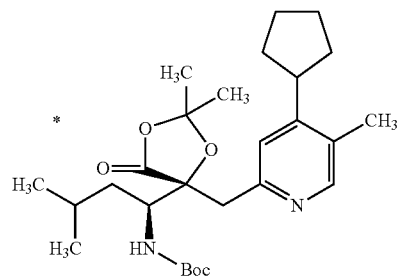 [SMILES: Cc1cnc(C[C@]2([C@H](CC(C)C)NC(=O)OC(C)(C)C)OC(C)(C)OC2=O)cc1C1CCCC1] |
| 190 | 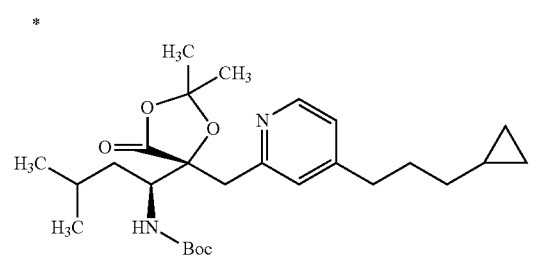 [SMILES: CC(C)C[C@H](NC(=O)OC(C)(C)C)[C@@]1(Cc2cc(CCCC3CC3)ccn2)OC(C)(C)OC1=O] |
| 191 | 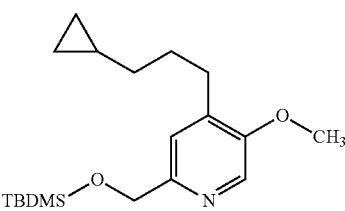 |
| 192 | 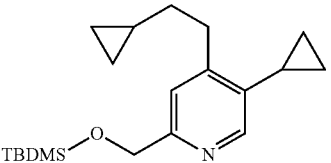 |
TABLE 34
| PEx | Str |
|---|---|
| 193 | 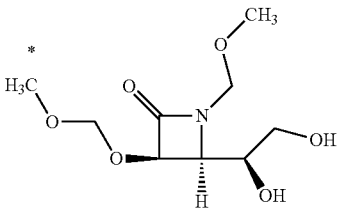 [SMILES: COCO[C@H]1C(=O)N(COC)[C@H]1[C@H](O)CO] |
| 194 | 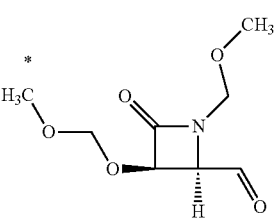 |
| 195 | 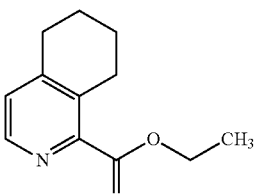 |
| 196 | 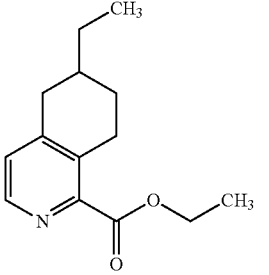 [SMILES: CCOC(=O)c1nccc2c1CCC(CC)C2] |
| 197 | 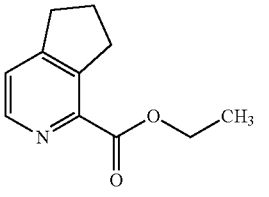 |

TABLE 34-continued

| PEx | Str |
|---|---|
| 198 | (ethyl 6-ethyl-6,7-dihydro-5H-cyclopenta[c]pyridine-1-carboxylate) |
| 199 | (ethyl 6-(2-methylallyl)-6,7-dihydro-5H-cyclopenta[c]pyridine-1-carboxylate) |
| 200 | * (ethyl (6S)-6-(but-3-en-1-yl)-6,7-dihydro-5H-cyclopenta[c]pyridine-1-carboxylate) |
| 201 | * (ethyl (6S)-6-allyl-6,7-dihydro-5H-cyclopenta[c]pyridine-1-carboxylate) |
| 202 | * (ethyl (6R)-6-allyl-6,7-dihydro-5H-cyclopenta[c]pyridine-1-carboxylate) |
| 203 | (ethyl 5-ethyl-6,7-dihydro-5H-cyclopenta[c]pyridine-1-carboxylate) |
| 204 | * (ethyl (5S)-5-allyl-6,7-dihydro-5H-cyclopenta[c]pyridine-1-carboxylate) |

TABLE 35

| PEx | Str |
|---|---|
| 205 | (ethyl 6-allyl-5,6,7,8-tetrahydroisoquinoline-1-carboxylate) |
| 206 | (ethyl 6-(benzyloxy)-5,6,7,8-tetrahydroisoquinoline-1-carboxylate) |
| 207 | (ethyl spiro[cyclopentane-1,6'-tetrahydroisoquinoline]-1'-carboxylate) |
| 208 | (ethyl spiro[cyclohexane-1,6'-tetrahydroisoquinoline]-1'-carboxylate) |

TABLE 35-continued
| PEx | Str |
|---|---|
| 209 | 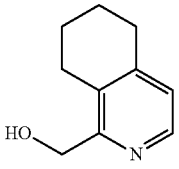 [SMILES: OCc1nccc2c1CCCC2] |
| 210 | 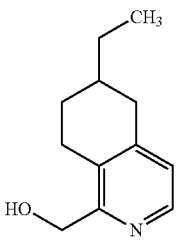 |
| 211 | 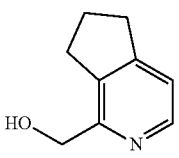 [SMILES: OCc1nccc2c1CCC2] |
| 212 | 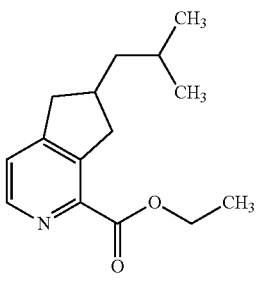 [SMILES: CCOC(=O)c1nccc2c1CC(CC(C)C)C2] |
| 213 | 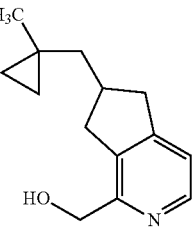 |
| 214 | 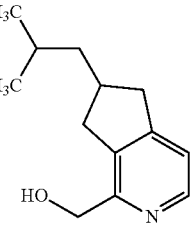 |
| 215 | 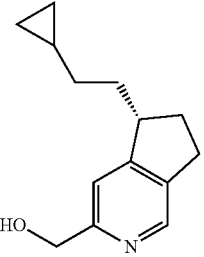 |
TABLE 35-continued
| PEx | Str |
|---|---|
| 216 | 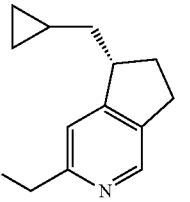 |
TABLE 36
| PEx | Str |
|---|---|
| 217 | 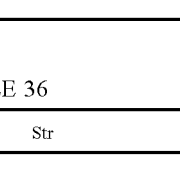 |
| 218 | 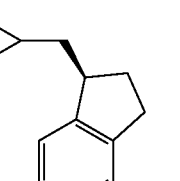 |
| 219 | 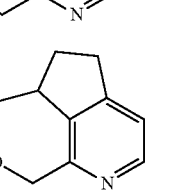 |
| 220 | 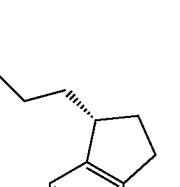 |
| 221 | 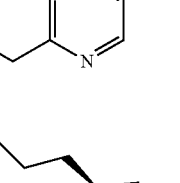 |

TABLE 36-continued

| PEx | Str |
|---|---|
| 222 | (structure: BnO-substituted tetrahydroisoquinoline with CH2OH) |
| 223 | (structure: spiro[cyclopentane-tetrahydroisoquinoline] with CH2OH) |
| 224 | (structure: spiro[cyclohexane-dihydrocyclopenta[c]pyridine] with CH2OH) |
| 225 | (structure: ethyl-substituted dihydrocyclopenta[c]pyridine with CH2OH) |
| 226 | * (structure: (R)-3-allylcyclopentanone) |
| 227 | * (structure: (S)-3-vinylcyclopentanone — with H2C=) |
| 228 | * (structure: ethyl 4-(2-cyclopropylethyl)-6,7-dihydro-5H-cyclopenta[c]pyridine-1-carboxylate N-oxide) |
| 229 | * (structure: ethyl 4-(2-cyclopropylethyl)-6-cyano-6,7-dihydro-5H-cyclopenta[c]pyridine-1-carboxylate) |
| 230 | * (structure: 4-(2-cyclopropylethyl)-6-(methoxycarbonyl)-6,7-dihydro-5H-cyclopenta[c]pyridine-1-carboxylic acid) |

TABLE 37

| PEx | Str |
|---|---|
| 231 | * (structure: methyl 4-(2-cyclopropylethyl)-6,7-dihydro-5H-cyclopenta[c]pyridine-2-carboxylate) |

TABLE 37-continued
| PEx | Str |
|---|---|
| 232 | 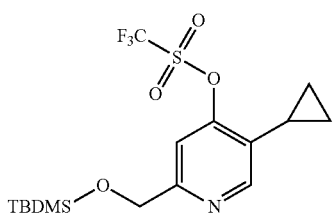 |
| 233 | 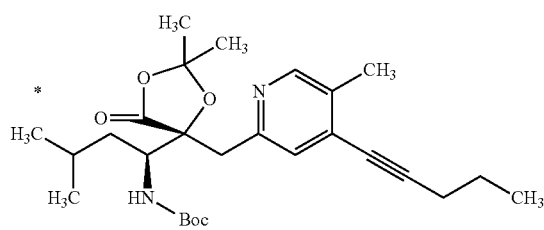 [SMILES: CCCC#Cc1cc(C[C@]2([C@H](CC(C)C)NC(=O)OC(C)(C)C)OC(C)(C)OC2=O)ncc1C] |
| 234 | 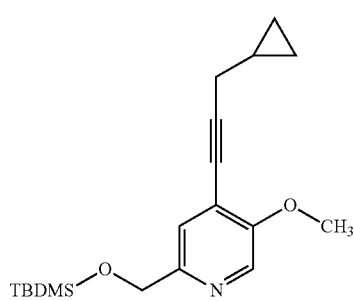 |
| 235 | 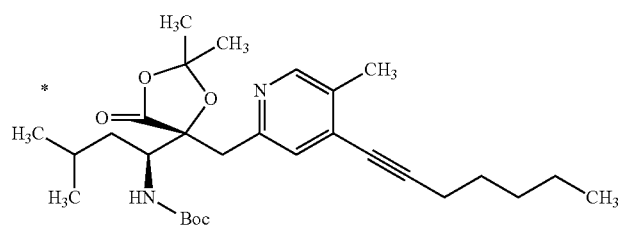 [SMILES: CCCCCC#Cc1cc(C[C@]2([C@H](CC(C)C)NC(=O)OC(C)(C)C)OC(C)(C)OC2=O)ncc1C] |
| 236 | 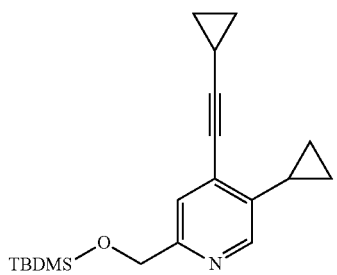 |
| 237 | 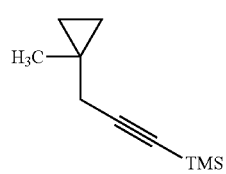 |

TABLE 37-continued

| PEx | Str |
|---|---|
| 238 | 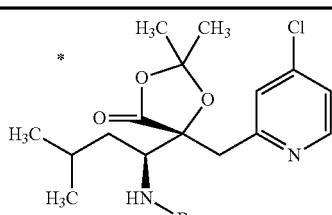 |

TABLE 38

| PEx | PSyn | DATA |
|---|---|---|
| 1 | — | ESI+: 431.3 |
| 2 | — | ESI+: 393.3 |
| 3 | — | ESI+: 254.2 [M + Na]+ |
| 4 | — | ESI+: 298.2 [M + Na]+ |
| 5 | — | ESI+: 471.2 |
| 6 | — | ESI+: 451.3 |
| 7 | — | ESI+: 158.0 |
| 8 | — | ESI+: 423.3 |
| 9 | — | ESI+: 304.1 |
| 10 | — | ESI+: 306.2 |
| 11 | — | ESI+: 200.1 |
| 12 | — | ESI+: 244.2 |
| 13 | — | ESI+: 320.3 |
| 14 | — | ESI+: 202.1 |
| 15 | — | ESI+: 489.3 |
| 16 | — | ESI+: 260.2 |
| 17 | — | ESI+: 324.2 [M + Na]+ |
| 18 | — | ESI+: 561.3 |
| 19 | — | ESI+: 288.1 |
| 20 | — | ESI+: 450.0, 451.9, 454.0 [M + Na]+ |
| 21 | — | ESI− 302.1 [M − H]− |
| 22 | — | ESI+: 363.2 |
| 23 | — | $^1$H NMR (400 MHz, DMSO-$d_6$) δ ppm: −0.25−−0.04 (3H, m), 0.01-0.12 (1H, m), 0.25-0.37 (2H, m), 0.57-0.68 (1H, m), 0.84 (3H, d, J = 6.6 Hz), 0.90 (1H, dd, J = 13.9, 6.4 Hz), 1.14 (1H, ddd, J = 13.1, 7.3, 5.4 Hz), 1.43-1.56 (1H, m) |
| 24 | — | ESI+: 429.1 |
| 25 | — | CI+: 207.9 M+ |
| 26 | — | CI+: 209.1 |
| 27 | — | ESI+: 338.2 |
| 28 | — | ESI+: 206.1 |
| 29 | — | ESI+: 298.2 |
| 30 | — | CI+: 266.1 |
| 31 | — | ESI+: 206.1 |
| 32 | — | ESI+: 384.3 [M + Na]+ |
| 33 | — | ESI+: 314.0 [M + Na]+ |

TABLE 39

| PEx | PSyn | DATA |
|---|---|---|
| 34 | — | ESI+: 294.1 [M + Na]+ |
| 35 | — | ESI+: 278.1 |
| 36(1) | — | ESI+: 246.2 |
| 36(2) | — | ESI+: 246.2 |
| 37 | — | ESI+: 218.2 |
| 38 | — | $^1$H NMR (400 MHz, CDCl$_3$) δ ppm: 0.55-0.60 (2H, m), 0.72-0.76 (2H, m), 1.19 (3H, s), 3.20 (2H, s) |
| 39 | — | CI+: 139.1 |
| 40 | — | CI+: 139.1 |
| 41 | — | ESI+: 197.1 |
| 42 | — | ESI+: 276.2 |
| 43 | — | ESI+: 248.1 |
| 44 | — | ESI+: 285.1 |
| 45 | — | ESI+: 290.2 |
| 46 | — | ESI+: 246.2 |
| 47 | — | ESI+: 270.1 |
| 48 | — | ESI+: 402.1 |
| 49 | — | ESI+: 473.4 |
| 50 | — | ESI+: 280.2 |
| 51 | — | ESI+: 214.1 |
| 52 | — | CI+: 167.1 |
| 53 | — | ESI+: 455.3 |
| 54 | — | ESI+: 559.3 |
| 55 | — | ESI+: 345.2 |
| 56 | — | ESI+: 357.2, 359.2 |
| 57(1) | — | ESI+: 391.4 |
| 57(2) | — | ESI+: 391.4 |
| 58 | — | ESI+: 403.2 |
| 59 | 1 | ESI+: 435.3 |
| 60 | 1 | ESI+: 431.3 |
| 61 | 1 | ESI+: 431.3 |
| 62 | 1 | ESI+: 501.4 |
| 63 | 1 | ESI+: 501.4 |
| 64 | 1 | ESI+: 419.4 |
| 65 | 1 | ESI+: 431.4 |
| 66 | 1 | ESI+: 535.3 |

TABLE 40

| PEx | PSyn | DATA |
|---|---|---|
| 67 | 1 | ESI+: 417.3 |
| 68 | 1 | ESI+: 517.4 |
| 69 | 1 | ESI+: 531.4 |
| 70 | 1 | ESI+: 517.4 |
| 71 | 1 | ESI+: 431.2 |
| 72 | 1 | ESI+: 519.5 |
| 73 | 1 | ESI+: 501.3 |
| 74 | 1 | ESI+: 549.5 |
| 75 | 1 | ESI+: 507.3 |
| 76 | 1 | ESI+: 433.4 |
| 77 | 2 | ESI+: 222.1 |
| 78 | 2 | ESI+: 218.2 |
| 79 | 2 | ESI+: 379.3 |
| 80 | 2 | ESI+: 405.4 |
| 81 | 2 | ESI+: 405.4 |
| 82 | 3 | ESI+: 246.1 |
| 83 | 5 | ESI+: 457.3 |
| 84 | 5 | ESI+: 483.3 |
| 85 | 5 | ESI+: 483.3 |
| 86 | 5 | ESI+: 485.2 |
| 87 | 6 | ESI+: 437.2 |
| 88 | 6 | ESI+: 463.3 |
| 89 | 6 | ESI+: 463.3 |
| 90 | 6 | ESI+: 465.2 |
| 91 | 8 | ESI+: 451.2 |
| 92 | 8 | ESI+: 463.3 |
| 93 | 8 | ESI+: 463.3 |
| 94 | 8 | ESI+: 449.2 |
| 95 | 8 | ESI+: 435.2 |
| 96 | 8 | ESI+: 437.3 |
| 97 | 8 | ESI+: 435.2 |
| 98 | 8 | ESI+: 463.3 |

TABLE 40-continued

| PEx | PSyn | DATA |
|---|---|---|
| 99 | 8 | ESI+: 463.3 |
| 100 | 8 | ESI+: 435.2 |
| 101 | 8 | ESI+: 449.2 |
| 102 | 8 | ESI+: 463.3 |

TABLE 41

| PEx | PSyn | DATA |
|---|---|---|
| 103 | 8 | ESI+: 437.3 |
| 104 | 8 | ESI+: 451.4 |
| 105 | 9 | ESI+: 318.2 |
| 106 | 11 | ESI+: 232.2 |
| 107 | 11 | ESI+: 214.1 |
| 108 | 12 | ESI+: 258.1 |
| 109 | 14 | ESI+: 485.3 |
| 110 | 14 | ESI+: 471.3 |
| 111 | 14 | ESI+: 499.5 |
| 112 | 14 | ESI+: 499.3 |
| 113 | 14 | ESI+: 499.4 |
| 114 | 14 | ESI+: 485.3 |
| 115 | 14 | ESI+: 188.1 |
| 116 | 1 | ESI+: 461.4 |
| 117 | 15 | ESI+: 503.6 |
| 118 | 15 | ESI+: 477.4 |
| 119 | 15 | ESI+: 491.4 |
| 120 | 15 | ESI+: 503.3 |
| 121 | 15 | ESI+: 515.3 |
| 122 | 15 | ESI+: 503.4 |
| 123 | 15 | ESI+: 489.4 |
| 124 | 15 | ESI+: 192.1 |
| 125 | 15 | ESI+: 407.4 |
| 126 | 16 | CI+: 211.2 |
| 127 | 16 | ESI+: 260.2 |
| 128 | 16 | ESI+: 246.2 |
| 129 | 16 | ESI+: 246.2 |
| 130 | 16 | ESI+: 260.2 |
| 131 | 16 | ESI+: 260.2 |
| 132 | 16 | ESI+: 260.2 |
| 133 | 16 | CI+: 223.2 |
| 134 | 16 | ESI+: 328.2 [M + Na]+ |
| 135 | 17 | ESI+: 330.1 |
| 136 | 17 | ESI+: 366.2 [M + Na]+ |
| 137 | 17 | ESI+: 342.1 [M + Na]+ |
| 138 | 17 | ESI+: 336.1 [M + Na]+ |

TABLE 42

| PEx | PSyn | DATA |
|---|---|---|
| 139 | 18 | ESI+: 427.3 |
| 140 | 18 | ESI+: 377.4 |
| 141 | 18 | ESI+: 405.4 |
| 142 | 18 | ESI+: 415.2, 417.2 |
| 143 | 18 | ESI+: 433.4 |
| 144 | 18 | ESI+: 501.3 |
| 145 | 18 | ESI+: 485.2, 487.1 |
| 146 | 18 | ESI+: 489.3 |
| 147 | 18 | ESI+: 501.4 |
| 148 | 18 | ESI+: 487.3 |
| 149 | 18 | ESI+: 487.4 |
| 150 | 18 | ESI+: 499.2, 501.2 |
| 151 | 18 | ESI+: 485.3, 487.2 |
| 152 | 18 | ESI+: 501.4 |
| 153 | 18 | ESI+: 553.4 |
| 154 | 18 | ESI+: 561.3 |
| 155 | 18 | ESI+: 543.4 |
| 156 | 18 | ESI+: 543.4 |
| 157 | 18 | ESI+: 545.2, 547.2 |
| 158 | 18 | ESI+: 501.5 |
| 159 | 19 | ESI+: 296.2 [M + Na]+ |
| 160 | 20 | ESI+: 436.0, 438.0, 440.0 [M + Na]+ |
| 161 | 20 | ESI+: 426.0, 428.0, 430.0 [M + Na]+ |

TABLE 42-continued

| PEx | PSyn | DATA |
|---|---|---|
| 162 | 20 | ESI+: 419.9, 421.9, 423.9 [M + Na]+ |
| 163 | 21 | ESI+: 290.1 |
| 164 | 21 | ESI+: 302.1 [M + Na]+ |
| 165 | 21 | ESI+: 296.2 [M + Na]+ |
| 166 | 22 | ESI+: 429.4 |
| 167 | 22 | ESI+: 403.4 |
| 168 | 22 | ESI+: 405.3 |
| 169 | 22 | ESI+: 538.4 |
| 170 | 22 | ESI+: 391.4 |
| 171 | 22 | ESI+: 439.2 |
| 172 | 22 | ESI+: 214.1 |
| 173 | 22 | ESI+: 439.4 |
| 174 | 22 | ESI+: 473.4 |

TABLE 43

| PEx | PSyn | DATA |
|---|---|---|
| 175 | 22 | ESI+: 405.3 |
| 176 | 22 | ESI+: 489.4 |
| 177 | 22 | ESI+: 513.5 |
| 178 | 22 | ESI+: 281.2 |
| 179 | 22 | ESI+: 487.4 |
| 180 | 24 | ESI+: 489.3 |
| 181 | 24 | ESI+: 519.4 |
| 182 | 24 | ESI+: 489.3 |
| 183 | 28 | ESI+: 407.3 |
| 184 | 28 | ESI+: 393.4 |
| 185 | 28 | ESI+: 441.3 |
| 186 | 28 | ESI+: 457.4 |
| 187 | 16 | ESI+: 260.2 |
| 188 | 28 | ESI+: 477.4 |
| 189 | 28 | ESI+: 475.3 |
| 190 | 28 | ESI+: 475.4 |
| 191 | 28 | ESI+: 336.2 |
| 192 | 28 | ESI+: 332.2 |
| 193 | 29 | ESI+: 236.0 |
| 194 | 30 | ESI+: 204.1 |
| 195 | 36 | ESI+: 206.1 |
| 196 | 36 | ESI+: 234.2 |
| 197 | 36 | ESI+: 192.1 |
| 198 | 36 | ESI+: 220.1 |
| 199 | 36 | ESI+: 246.2 |
| 200 | 36 | ESI+: 246.1 |
| 201 | 36 | ESI+: 232.1 |
| 202 | 36 | ESI+: 232.2 |
| 203 | 36 | ESI+: 220.1 |
| 204 | 36 | ESI+: 246.1 |
| 205 | 36 | ESI+: 246.2 |
| 206 | 36 | ESI+: 312.2 |
| 207 | 36 | ESI+: 260.1 |
| 208 | 36 | ESI+: 260.1 |
| 209 | 37 | ESI+: 164.1 |
| 210 | 37 | ESI+: 192.1 |

TABLE 44

| PEx | PSyn | DATA |
|---|---|---|
| 211 | 37 | ESI+: 150.1 |
| 212 | 28 | ESI+: 248.2 |
| 213 | 37 | ESI+: 218.2 |
| 214 | 37 | ESI+: 206.2 |
| 215 | 37 | ESI+: 218.2 |
| 216 | 37 | ESI+: 204.2 |
| 217 | 37 | ESI+: 204.1 |
| 218 | 37 | ESI+: 178.1 |
| 219 | 37 | ESI+: 218.1 |
| 220 | 37 | ESI+: 218.1 |
| 221 | 37 | ESI+: 218.1 |
| 222 | 37 | ESI+: 270.1 |
| 223 | 37 | ESI+: 218.2 |
| 224 | 37 | ESI+: 218.1 |

TABLE 44-continued

| PEx | PSyn | DATA |
|-----|------|------|
| 225 | 37 | ESI+: 178.2 |
| 226 | 39 | CI+: 125.1 |
| 227 | 40 | CI+: 125.0 |
| 228 | 42 | ESI+: 276.2 |
| 229 | 44 | ESI+: 285.2 |
| 230 | 45 | ESI+: 290.2 |
| 231 | 46 | ESI+: 246.1 |
| 232 | 48 | ESI+: 412.2 |
| 233 | 49 | ESI+: 473.4 |
| 234 | 49 | ESI+: 332.2 |
| 235 | 49 | ESI+: 501.4 |
| 236 | 49 | ESI+: 328.2 |
| 237 | 52 | $^1$H NMR (400 MHz, CDCl$_3$) δ ppm: 0.15 (9H, s), 0.25-0.30 (2H, m), 0.44-0.49 (2H, m), 1.12 (3H, s), 2.25 (2H, s) |
| 238 | 56 | ESI+: 427.3, 449.3 |

INDUSTRIAL APPLICABILITY

The compound represented by Formula (I) or a salt thereof has inhibitory activity against P-LAP, i.e. the AVP-degrading enzyme, and maintains and/or increases an endogenous AVP level to reduce urine production. Such a compound thus is expected to be used as an agent for treating nocturia, and is also expected to be used as an agent for treating any other voiding dysfunction or polyuria associated with a decreased AVP level, such as pollakiuria, urinary incontinence, and nocturnal enuresis.

The invention claimed is:

1. A compound of formula (I) or a salt thereof:

[Formula 1]

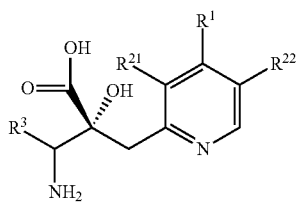

(I)

wherein

R$^1$ is C$_{1-10}$ alkyl optionally having 1 to 5 substituents selected from group G$^1$; C$_{2-10}$ alkenyl optionally having 1 to 5 substituents selected from group G$^1$; C$_{2-10}$ alkynyl optionally having 1 to 5 substituents selected from group G$^1$; -lower alkylene-X-(lower alkyl optionally having 1 to 5 substituents selected from group G$^1$); R$^4$; 5- or 6-membered heterocyclic group optionally having 1 to 5 substituents selected from group G$^3$; -lower alkylene-R$^4$; -lower alkenylene-R$^4$; -lower alkylene-X—R$^4$; or -lower alkylene-X-lower alkylene-R$^4$, or R$^1$ forms, together with R$^{21}$ or R$^{22}$ on the pyridine ring bonded thereto, a hydrocarbon ring fused with the pyridine ring, represented by any of the following formulas (i) to (iv):

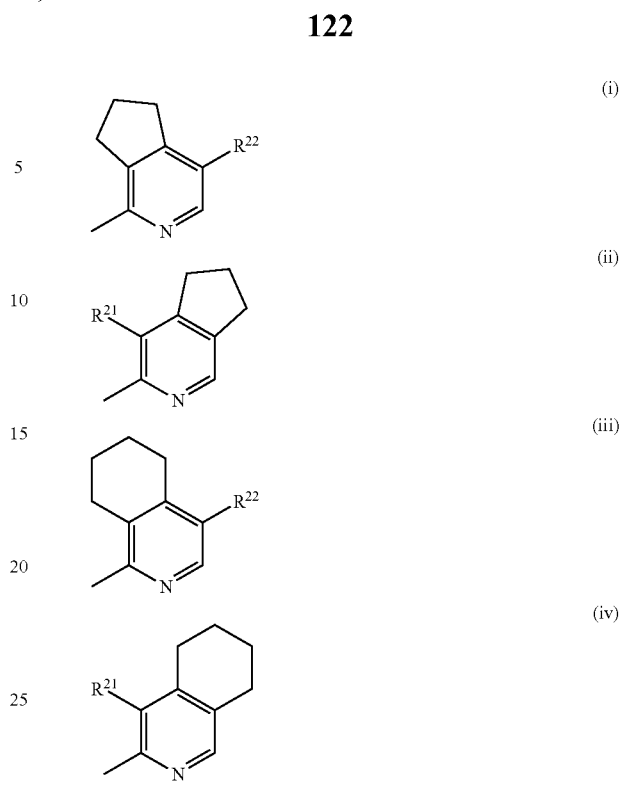

wherein the hydrocarbon ring optionally has 1 to 4 substituents selected from the group consisting of lower alkyl optionally having 1 to 5 substituents selected from group G$^1$, cycloalkyl optionally having 1 to 5 substituents selected from group G$^2$, -lower alkylene-R$^4$, and —O-lower alkylene-R$^4$, or the hydrocarbon ring optionally forms a spiro ring with C$_{3-8}$ cycloalkane, R$^{21}$ and R$^{22}$ are the same or different and each are H; lower alkyl optionally having 1 to 5 substituents selected from group G$^1$; —X-lower alkyl; —X-halogeno lower alkyl; cycloalkyl optionally having 1 to 5 substituents selected from group G$^2$; or -lower alkylene-(cycloalkyl optionally having 1 to 5 substituents selected from group G$^2$), R$^3$ is lower alkyl optionally having 1 to 5 substituents selected from group G$^1$; -lower alkylene-X-(lower alkyl optionally having 1 to 5 substituents selected from group G$^1$); -lower alkylene-X-(lower alkenyl optionally having 1 to 5 substituents selected from group G$^1$); -lower alkylene-(cycloalkyl optionally having 1 to 5 substituents selected from group G$^2$); -lower alkylene-X-(cycloalkyl optionally having 1 to 5 substituents selected from group G$^2$); or -lower alkylene-X-lower alkylene-(cycloalkyl optionally having 1 to 5 substituents selected from group G$^2$), each X is independently O or S, each R$^4$ is independently cycloalkyl optionally having 1 to 5 substituents selected from group G$^2$; cycloalkenyl optionally having 1 to 5 substituents selected from group G$^2$; or aryl optionally having 1 to 5 substituents selected from group G$^3$, group G$^1$ consists of halogen, OH, —O-lower alkyl, —S-lower alkyl, —O-halogeno lower alkyl, and CN, group G$^2$ consists of the groups of group G$^1$, lower alkyl optionally having 1 to 5 substituents selected from group G¹, and -lower alkylene-(cycloalkyl optionally substituted by 1 to 4 lower alkyl groups), and group G³ consists of the groups of group G¹, lower alkyl optionally having 1 to 5 substituents selected from group G¹, and benzyloxycarbonyl.

2. The compound according to claim 1 or a salt thereof, wherein $R^1$ is $C_{1-10}$ alkyl optionally having 1 to 5 substituents selected from group G¹; $C_{2-10}$ alkenyl optionally having 1 to 5 substituents selected from group G¹; $C_{2-10}$ alkynyl optionally having 1 to 5 substituents selected from group G¹; cycloalkyl optionally having 1 to 5 substituents selected from group G²; cycloalkenyl; aryl optionally having 1 to 5 substituents selected from group G³; 5- or 6-membered heterocyclic group optionally having 1 to 5 substituents selected from group G³; -lower alkylene-(cycloalkyl optionally having 1 to 5 substituents selected from group G²); -lower alkylene-(aryl optionally having 1 to 5 substituents selected from group G³); -lower alkenylene-aryl; -lower alkylene-O-cycloalkyl; or -lower alkylene-O-aryl, or $R^1$ forms, together with $R^{21}$ or $R^{22}$ on the pyridine ring bonded thereto, a hydrocarbon ring fused with the pyridine ring, represented by any of formulas (i) to (iv), wherein the hydrocarbon ring optionally has 1 to 4 substituents selected from the group consisting of lower alkyl, cycloalkyl, -lower alkylene-(cycloalkyl optionally having 1 to 5 substituents selected from group G²), —O-lower alkylene-(cycloalkyl optionally having 1 to 5 substituents selected from group G²), and -O-lower alkylene-(aryl optionally having 1 to 5 substituents selected from group G³), or the hydrocarbon ring optionally forms a spiro ring with $C_{3-6}$ cycloalkane, $R^{21}$ and $R^{22}$ are the same or different and each are H, lower alkyl optionally having 1 to 5 substituents selected from group G¹, —X-lower alkyl, or cycloalkyl optionally having 1 to 5 substituents selected from group G², and $R^3$ is lower alkyl optionally having 1 to 5 substituents selected from group G¹; -lower alkylene-S-(lower alkyl optionally having 1 to 5 substituents selected from group G¹); -lower alkylene-S-lower alkenyl; -lower alkylene-(cycloalkyl optionally having 1 to 5 substituents selected from group G²); -lower alkylene-S-(cycloalkyl optionally having 1 to 5 substituents selected from group G²); or -lower alkylene-X-lower alkylene-(cycloalkyl optionally having 1 to 5 substituents selected from group G²).

3. The compound according to claim 2 or a salt thereof, wherein $R^1$ is $C_{1-10}$ alkyl optionally having 1 to 5 substituents selected from the group consisting of halogen and OH; $C_{2-10}$ alkynyl; cycloalkyl optionally having 1 to 5 substituents selected from the group consisting of lower alkyl and -lower alkylene-cycloalkyl; cycloalkenyl; aryl optionally substituted by one (—O-lower alkyl); tetrahydropyridinyl optionally substituted by one benzyloxycarbonyl; dihydropyranyl; tetrahydropyranyl; -lower alkylene-(cycloalkyl optionally substituted by one lower alkyl); -lower alkylene-(aryl optionally having 1 to 5 substituents selected from the group consisting of lower alkyl and —O-lower alkyl); -lower alkenylene-aryl; -lower alkylene-O-cycloalkyl; or -lower alkylene-O -aryl, and $R^{21}$ and $R^{22}$ are the same or different and each are H, lower alkyl, —O-lower alkyl, or cycloalkyl, or $R^1$ forms, together with $R^{21}$ or $R^{22}$ on the pyridine ring bonded thereto, a hydrocarbon ring fused with the pyridine ring, represented by any of formulas (i) to (iii), wherein the hydrocarbon ring optionally has 1 to 4 substituents selected from the group consisting of lower alkyl, -lower alkylene-(cycloalkyl optionally substituted by lower alkyl), —O-lower alkylene-cycloalkyl, and —O-lower alkylene-aryl, or the hydrocarbon ring optionally forms a spiro ring with $C_{3-6}$ cycloalkane, and each of $R^{21}$ and $R^{22}$ is H, and $R^3$ is lower alkyl optionally substituted by 1 to 5 halogens; -lower alkylene-S-lower alkyl; -lower alkylene-S-lower alkenyl; -lower alkylene-($C_{3-8}$ cycloalkyl optionally substituted by one lower alkyl); -lower alkylene-S-$C_{3-8}$ cycloalkyl; or -lower alkylene-X-lower alkylene-$C_{3-8}$ cycloalkyl.

4. The compound according to claim 3 or a salt thereof, wherein $R^1$ is $C_{1-10}$ alkyl; cycloalkyl substituted by one (-lower alkylene-cycloalkyl); or -lower alkylene-cycloalkyl, $R^{21}$ is H, and $R^{22}$ is H or lower alkyl, or $R^1$ forms, together with $R^{21}$ or $R^{22}$ on the pyridine ring bonded thereto, a hydrocarbon ring fused with the pyridine ring, represented by any of formulas (i) and (ii), wherein the hydrocarbon ring is substituted by one (-lower alkylene-cycloalkyl), and $R^3$ is lower alkyl, -lower alkylene-S-lower alkyl, -lower alkylene-$C_{3-8}$ cycloalkyl, -lower alkylene-S-$C_{3-8}$ cycloalkyl, or -lower alkylene-O-lower alkylene-$C_{3-8}$ cycloalkyl.

5. The compound according to claim 4 or a salt thereof, wherein $R^1$ is -lower alkylene-cycloalkyl, $R^{21}$ is H, and $R^{22}$ is H or $C_{1-4}$ alkyl, or $R^1$ forms, together with $R^{21}$ on the pyridine ring bonded thereto, a hydrocarbon ring fused with the pyridine ring, represented by formula (i), wherein the hydrocarbon ring is substituted by one (-lower alkylene-cycloalkyl), and $R^3$ is lower alkyl, -lower alkylene-S-lower alkyl, or -lower alkylene-$C_{3-6}$ cycloalkyl.

6. The compound according to claim 5 or a salt thereof, wherein $R^1$ is 3-cyclopropylpropyl, $R^{21}$ is H, and $R^{22}$ is H or methyl, or $R^1$ forms, together with $R^{21}$ on the pyridine ring bonded thereto, a hydrocarbon ring fused with the pyridine ring, represented by the following formula (ia):

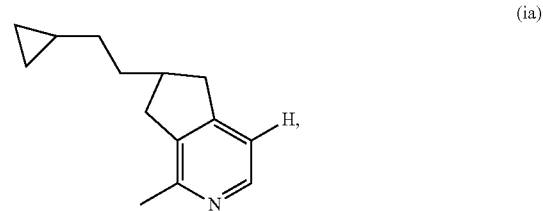

(ia)

and $R^3$ is isobutyl, methylthiomethyl, n-propylthiomethyl, or 2-cyclopropylethyl.

7. The compound according to claim 1 or a salt thereof, wherein $R^1$ is $C_{1-10}$ alkyl optionally having 1 to 5 substituents selected from group G¹; $C_{2-10}$ alkenyl optionally having 1 to 5 substituents selected from group G¹; $C_{2-10}$ alkynyl optionally having 1 to 5 substituents selected from group G¹; -lower alkylene-X-(lower alkyl optionally having 1 to 5 substituents selected from group G¹); $R^4$; 5- or 6-membered heterocyclic group optionally having 1 to 5 substituents selected from group G³; -lower alkylene-$R^4$; -lower alkenylene-$R^4$; -lower alkylene-X-$R^4$; or -lower alkylene-X-lower alkylene-$R^4$, and $R^{21}$ and $R^{22}$ are the same or different and each are H; lower alkyl optionally having 1 to 5 substituents selected from group G¹; —X-lower alkyl; —X-halogeno lower alkyl; cycloalkyl optionally having 1 to 5 substituents selected from group G²; or -lower alkylene-(cycloalkyl optionally having 1 to 5 substituents selected from group G²).

8. The compound according to claim 1 or a salt thereof, wherein R¹ forms, together with R²¹ or R²² on the pyridine ring bonded thereto, a hydrocarbon ring fused with the pyridine ring, represented by any of formulas (i) to (iv), wherein the hydrocarbon ring optionally has 1 to 4 substituents selected from the group consisting of lower alkyl optionally having 1 to 5 substituents selected from group G¹, cycloalkyl optionally having 1 to 5 substituents selected from group G², -lower alkylene-R⁴, and —O-lower alkylene-R⁴, or the hydrocarbon ring optionally forms a spiro ring with $C_{3-8}$ cycloalkane, and each of R²¹ and R²² is H; lower alkyl optionally having 1 to 5 substituents selected from group G¹; —X-lower alkyl; —X-halogeno lower alkyl; cycloalkyl optionally having 1 to 5 substituents selected from group G²; or -lower alkylene-(cycloalkyl optionally having 1 to 5 substituents selected from group G²).

9. The compound or a salt thereof according to claim 1, wherein the compound is selected from the group consisting of (2R,3R)-3-amino-2-{[4-(3-cyclopropylpropyl)-5-methylpyridin-2-yl]methyl}-2-hydroxy-4-(methylsulfanyl)butanoic acid, (2R,3S)-3-amino-5-cyclopropyl-2-{[4-(3-cyclopropylpropyl)-5-methylpyridin-2-yl]methyl}-2-hydroxypentanoic acid, (2R,3S)-3-amino-2-{[4-(3-cyclopropylpropyl)-5-methylpyridin-2-yl]methyl}-2-hydroxy-5-methylhexanoic acid, (2R,3S)-3-amino-2-{8 (6S)-6-(2-cyclopropylethyl)-6,7-dihydro-5H-cyclopenta[c]pyridin-1-yl]methyl}-2-hydroxy-5-methylhexanoic acid, (2R,3S)-3-amino-5-cyclopropyl-2-{[4-3-cyclopropylpropyl)pyridin-2-yl]methyl}-2-hydroxypentanoic acid, (2R,3R)-3-amino-2-{[R6R)-6-(2-cyclopropylethyl)-6,7-dihydro-5H-cyclopenta[c]pyridin-1-yl]methyl}-2-hydroxy-4-(methylsulfanyl)butanoic acid, (2R,3R)-3-amino-2-{[R6R)-6-(2-cyclopropylethyl)-6,7-dihydro-5H-cyclopenta[c]pyridin-1-yl]methyl}-2-hydroxy-4-(propylsulfanyl)butanoic acid, (2R,3R)-3-amino-2-{[(6S)-6-(2-cyclopropylethyl)-6,7-dihydro-5H-cyclopenta[c]pyridin-1-yl]methyl}-2-hydroxy-4-(methylsulfanyl)butanoic acid, and (2R,3S)-3-amino-2-{[(6R)-6-(2-cyclopropylethyl)-6,7-dihydro-5H-cyclopenta[c]pyridin-1-yl]methyl}-2-hydroxy-5-methylhexanoic acid.

10. A pharmaceutical composition comprising a compound or a salt thereof according to claim 1 and an excipient.

11. A method of treating nocturia, comprising administering an effective amount of a compound or a salt thereof according to claim 1 to a subject in need thereof.

* * * * *